(12) United States Patent
Araldi et al.

(10) Patent No.: US 7,419,999 B2
(45) Date of Patent: Sep. 2, 2008

(54) GAMMA LACTAMS AS PROSTAGLANDIN AGONISTS AND USE THEREOF

(75) Inventors: Gian Luca Araldi, Plymouth, MA (US); Adulla P. Reddy, Walpole, MA (US); Zhong Zhao, Wayland, MA (US); Sean D. McKenna, Duxbury, MA (US); Bagna Bao, Sharon, MA (US)

(73) Assignee: Applied Research Systems ARS Holding N.V., Curacao (NL)

( * ) Notice: Subject to any disclaimer, the term of this patent is extended or adjusted under 35 U.S.C. 154(b) by 24 days.

(21) Appl. No.: 10/517,626

(22) PCT Filed: Jun. 9, 2003

(86) PCT No.: PCT/US03/18202

§ 371 (c)(1),
(2), (4) Date: Jul. 28, 2005

(87) PCT Pub. No.: WO03/103604

PCT Pub. Date: Dec. 18, 2003

(65) Prior Publication Data

US 2005/0288357 A1    Dec. 29, 2005

Related U.S. Application Data

(60) Provisional application No. 60/451,804, filed on Mar. 3, 2003, provisional application No. 60/387,340, filed on Jun. 10, 2002.

(51) Int. Cl.
*A61K 31/4015* (2006.01)
*A61K 31/5377* (2006.01)
*C07D 207/27* (2006.01)
*C07D 413/06* (2006.01)

(52) U.S. Cl. .................... 514/424; 514/235.5; 548/551; 544/141

(58) Field of Classification Search ................. 548/551; 514/424, 235.5; 544/141
See application file for complete search history.

(56) References Cited

U.S. PATENT DOCUMENTS

| 3,873,566 | A | 3/1975 | Scribner |
| 4,003,911 | A | 1/1977 | Scribner |
| 4,033,989 | A | 7/1977 | Bundy |
| 4,090,019 | A | 5/1978 | Williams et al. |
| 4,211,876 | A | 7/1980 | Scribner |
| 5,605,814 | A | 2/1997 | Abramovitz et al. |
| 5,759,789 | A | 6/1998 | Abramovitz et al. |
| 6,211,197 | B1 | 4/2001 | Belley et al. |
| 6,288,120 | B1 | 9/2001 | Cameron et al. |
| 2002/0065308 | A1 | 5/2002 | Cameron et al. |

FOREIGN PATENT DOCUMENTS

| EP | 0 752 421 A1 | 1/1997 |
| EP | 1 110 949 A1 | 6/2001 |
| EP | 1 481 976 A1 | 12/2004 |
| WO | WO 96/03380 A1 | 2/1996 |
| WO | WO 96/06822 A1 | 3/1996 |
| WO | WO 97/00863 A1 | 1/1997 |
| WO | WO 97/00864 A1 | 1/1997 |
| WO | WO 02/24647 A1 | 3/2002 |
| WO | WO 03/007941 A1 | 1/2003 |
| WO | WO 03/008377 A1 | 1/2003 |
| WO | WO 03/009872 A1 | 5/2004 |

OTHER PUBLICATIONS

Ebenezar et al. Expert Opin. Ther. Patents 2007, 17(9), 1131-1145.*
Abramovitz, et al. "The utilization of recombinant prostanoid receptors to determine the affinities and selectivities of prostaglandins and related analogs." Biochim Biophys Acta. 2000 Jan. 17;1483(2):285-93.
Bennett, et al. "Synthesis and biological activity of a series of 1-aryl-3-pyrazolidinones." J Med Chem. May 1976;19(5):715-7.
Boie, et al. "Molecular cloning and characterization of the four rat prostaglandin $E_2$ prostanoid receptor subtypes." Eur J Pharmacol. Dec. 11, 1997;340(2-3):227-41.
Coleman, et al. "Prostanoids and their receptors. Comprehensive Medicinal Chemistry." 1990 3:643-714.
Coleman, et al. "International Union of Pharmacology classification of prostanoid receptors: properties, distribution, and structure of the receptors and their subtypes." Pharmacol Rev. Jun. 1994;46(2):205-29.
Corey, et al. "A stable and easily prepared catalyst for the enantioselective reduction of ketones. Applications to Multistep Systheses." J. Am. Chem. Soc. 1987. 109:7925-26.
Fleisch, et al. "LY171883, 1-< 2-hydroxy-3-propyl-4-< 4-(1H-tetrazol-5-yl) butoxy > phenyl > ethanone, an orally active leukotriene D4 antagonist." J Pharmacol Exp Ther. Apr. 1985;233(1):148-57.
Gardiner, PJ. "Characterization of prostanoid relaxant/inhibitory receptors (psi) using a highly selective agonist, TR4979." Br J Pharmacol. Jan. 1986;87(1):45-56.
Hundertmark, et al. "$Pd(PhCN)_2Cl_2/P(t-Bu)_3$: a versatile catalyst for Sonogashira reactions of aryl bromides at room temperature." Org Lett. Jun. 15, 2000;2(12):1729-31.
Ichikawa, et al. "Molecular aspects of the structures and functions of the prostaglandin E receptors." J Lipid Mediat Cell Signal. Sep. 1996;14(1-3):83-7.

(Continued)

*Primary Examiner*—Joseph McKane
*Assistant Examiner*—Jason M Nolan
(74) *Attorney, Agent, or Firm*—Lahive & Cockfield, LLP; Giulio A. DeConti, Jr.; Cynthia M. Soroos

(57) ABSTRACT

1,2-substituted 5-pyrrolidinone compounds are provided, and methods of treatment and pharmaceutical composition that utilize or comprise one or more such compounds. Compounds of the invention are useful for a variety of therapies, including treating or preventing preterm labor, dysmenorrhea, asthma, hypertension, infertility or fertility disorder, undesired blood clotting, preeclampsia or eclampsia, an eosinophil disorder, sexual dysfunction, osteoporosis and other destructive bone disease or disorder, renal dysfunction, an immune deficiency disorder, dry eye, ichthyosis, elevated intraocular pressure, sleep disorder, or gastric ulcer, inflammatory disorders and other diseases and disorders associated with the prostaglandin family of compounds.

42 Claims, 3 Drawing Sheets

OTHER PUBLICATIONS

Langlois, et al. "Intramolecular Mitsunobu reaction in the region- and stereoselective synthesis of cis-4,5-disubstituted piperidin-2-ones." Tetrahedron Letters. 2000 41:8285-8288.

Macdonald, et al. "Syntheses of trans-5-oxo-hexahydro-pyrrolo[3,2-b]pyrroles and trans-5-oxo-hexahydro-furo[3,2-b]pyrroles (pyrrolidine trans-lactams and trans-lactones): new pharmacophores for elastase inhibition." J Med Chem. Oct. 8, 1998;41(21):3919-22.

Mikolajczyk, et al. "Synthesi8s of (±)-Rosaprostol." J. Org. Chem. 1998. 63:8894-8897.

Minami, et al. "Characterization of EP-receptor subtypes involved in allodynia and hyperalgesia induced by intrathecal administration of prostaglandin E2 to mice." Br J Pharmacol. Jul. 1994;112(3):735-40.

Nair, et al. "Folate analogues. 31. Synthesis of the reduced derivatives of 11-deazahomofolic acid, 10-methyl-11-deazahomofolic acid, and their evaluation as inhibitors of glycinamide ribonucleotide formyltransferase." J Med Chem. Jun. 1989;32(6):1277-83.

Okuma, et al. "An Efficient Synthesis of (R)-(+)-Recifeiolide and Related Macrolides by Using Enantiomerically Pure (R)- (-)-5-Methyl-2,2,2-triphenyl-1,2$A^5$-oxaphospholane." Tetrahedron. 1998. 54:4243-50.

Tani, et al. "Synthesis of a Highly Selective EP2-Receptor Agonist." Synlett. 2002, pp. 239-242.

Thivierge, et al. "Prostaglandin E2 induces resistance to human immunodeficiency virus-1 infection in monocyte-derived macrophages: downregulation of CCR5 expression by cyclic adenosine monophosphate." Blood. Jul. 1, 1998;92(1):40-5.

Ushikubi, et al. "Roles of prostanoids revealed from studies using mice lacking specific prostanoid receptors." Jpn J Pharmacol. Aug. 2000;83(4):279-85.

Wilkinson, et al. "Diethylanilineborane: A Practical, safe, and consistent-quality borane source for the large-scale enantioselective reduction of a ketone intermediate in the synthesis of (R,R)-Formoterol." Organic Process Research & Development. 2002 6:146-8.

* cited by examiner

GAMMA LACTAMS AS PROSTAGLANDIN AGONISTS AND USE THEREOF

RELATED APPLICATIONS

This application claims priority to PCT/US03/18202, filed on Jun. 9, 2003, which claims priority to US Provisional Application 60/451,804 filed on Mar. 3, 2003, and US Provisional Application 60/387,340 filed on Jun. 10, 2002, which are incorporated herein by reference.

BACKGROUND OF THE INVENTION

1. Field of the Invention

This invention provides substituted 1,2-substituted 5-pyrrolidinone compounds, methods of treatment and pharmaceutical compositions that utilize or comprise one or more such compounds. Compounds of the invention are useful for a variety of therapies, including preterm labor, ovulation induction, cervical ripening, dysmenorrhea, asthma, hypertension, infertility or fertility disorder, undesired blood clotting, preeclampsia or eclampsia, an eosinophil disorder, sexual dysfunction, including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory disorders and other diseases and disorders associated with the prostaglandin and receptors thereof. The invention further provides methods and pharmaceutical compositions comprising prostaglandin EP4 receptor agonists for the treatment of infertility disorders. More specifically, the present invention relates to such methods and pharmaceutical compositions for inducing ovulation, particularly ovulation triggering.

2. Background

Prostaglandins (PGs) which belong to the prostanoids family are known to have diverse biological activities such as contraction and relaxation of smooth muscle, inhibition and enhancement of neurotransmitter release, inhibition of lipolysis, inhibition of gastric secretion, inhibition of inflammatory mediator release (Coleman et al. *Prostanoids and their Receptors. In Comprehensive Medicinal Chemistry*, vol. 3, Ed J. C. Emmett, 643-714, Pergamon Press, Oxford, UK, 1990) that are mediated by different receptor subtypes (Coleman et al. *Pharmacological Reviews* 1994 46 (2), 205-229). Four subtypes of the prostaglandin EP receptor have been identified: EP1, EP2, EP3, and EP4. See also U.S. Pat. Nos. 5,605,814 and 5,759,789.

Knock-out mice lacking each type and sub-type of the EP receptor showed different roles for these receptors (Ushikubi at al. 2000, *Jpn. J. Pharmacol.* 83, 279-285) in various mechanisms such as ovulation, blood pressure control, closure of ductus arteriosus and bone resorption. Additional roles of EP receptors have been reported such as smooth muscle relaxation in cat trachea for EP2, vasodilatation for EP4 (Gardinier, *Br. J. Pharmac.* 1986, 87, 45-56; Coleman et al. 1994 *Pharmacological Reviews* 46 (2), 205-229) and anti-inflammatory activity for EP4 (Takayama et al. 2002, *The Journal of Biological Chemistry*, 277, 46, 44147-44154). Renal Prostaglandin E2 (PGE2) is crucial of normal renal function by dilating the glomerular microcirculation and vasa recta, supplying the renal medulla and modulating salt and water transport in the distal tubule.

Prostaglandin E2 (PGE2) is a natural ligand for all sub-types of the EP receptor. Consequently, selective effects on one of the sub-types of the EP receptor is impossible to achieve with the endogenous prostaglandins.

Certain prostanoid receptors and modulators of those receptors have been largely reported (*Eicosanoids: From Biotechnology to Therapeutic Applications* (Plenum Press, New York); *Journal of Lipid Mediators and Cell Signalling* 14: 83-87 (1996); *The British Journal of Pharmacology*, 112: 735-740 (1994); WO 96/06822; WO 97/00863; WO 97/00864; WO 96/03380; EP 752421; U.S. Pat. Nos. 6,211, 197, 4,211,876; 3,873,566; and Bennett et al. *J. Med. Chem.*, 19(5): 715-717 (1976).

Certain prostaglandin ligands and analogs have been reported to provide biological activity associated with prostaglandins (U.S. Pat. Nos. 6,288,120; 6,211,197; 4,090,019; 4,033,989; 4,003,911). E-type prostaglandin reported to be mediated through interaction with the prostaglandin E receptor(s). Certain compounds also have been reported as EP4 agonists (WO 02/24647, EP 1110949A1, WO03/009872 and WO 03/007941).

It would be desirable to have new compounds and methods for treatment of diseases and disorders associated with the prostaglandin family of compounds.

SUMMARY OF THE INVENTION

We have now found substituted 1,2-substituted 5-pyrrolidinone compounds that are useful for a variety of therapies, including alleviating, preventing and/or treating preterm labor, ovulation induction, cervical ripening, dysmenorrhea, asthma, hypertension, infertility or fertility disorder, undesired blood clotting, preeclampsia or eclampsia, an eosinophil disorder, sexual dysfunction, including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory disorders and other diseases and disorders associated with the prostaglandin family of compounds and receptors thereof.

The invention particularly provides methods of inducing ovulation, particularly ovulation triggering, in a mammal comprising administering an EP4 receptor agonist, an isomer thereof, a pro-drug of said agonist or isomer, or a pharmaceutically acceptable salt of said agonist, isomer or pro-drug.

Compounds of the invention include those of the following Formula I:

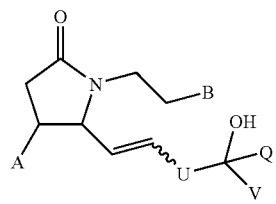

I wherein A is hydrogen or hydroxy;

B is selected from the group comprising or consisting of optionally substituted carbocyclic aryl, optionally substituted heteroalicyclic having from 3 to 8 ring atoms and at least one N, O or S ring atom and a heteroaromatic group having a single ring with 5 or 6 ring atoms and at least one N, O or S ring atom;

U is $(CH_2)_p$ wherein p is selected from 0, 1 and 2;

V and Q are each independently selected from the group comprising or consisting of hydrogen, optionally substituted alkyl preferably having 1 to about 12 carbon atoms, optionally substituted alkenyl preferably having 2 to about 12 carbon atoms, optionally substituted alkynyl preferably having from 2 to about 12 carbon atoms, optionally substituted $C_1$-$C_6$ heteroalkyl, optionally substituted $C_3$-$C_6$ cycloalkyl $C_1$-$C_6$ alkyl, optionally substituted $C_3$-$C_6$ heterocycloalkyl $C_1$-$C_6$ alkyl, optionally substituted aryl $C_1$-$C_6$ alkyl and —$CR^1R^2$—W, wherein $R^1$ and $R^2$ are independently selected from H and optionally substituted $C_1$-$C_6$ alkyl, preferably H; or $R^1$ and $R^2$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted aryl $C_1$-$C_6$ alkyl; with at least one of V and Q being other than hydrogen; and pharmaceutically acceptable salts thereof.

In Formula I, preferably substituent B is a substituted carbocyclic aryl, heteroalicyclic, or heteroaromatic group, e.g. such a ring group substituted by a carboxylate (e.g. —COOR where R is hydrogen or $C_1$-$C_6$ alkyl), amide (e.g. —CONHR where R is H is $C_1$-$C_6$ alkyl), and the like.

Preferred compounds of Formula I include those compounds where substituent A is hydrogen and/or substituent B is an optionally substituted thiophene, optionally substituted furan or optionally substituted carbocyclic aryl group particularly optionally substituted phenyl, such as compounds of the following Formula II:

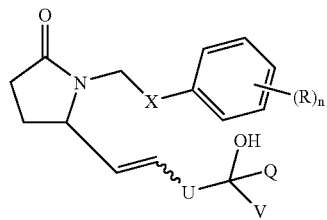

II wherein in Formula II: U, V and Q are the same as defined in Formula I above;

X is selected from oxygen, sulfur, sulfinyl (SO), sulfonyl ($SO_2$) and carbon, preferably is methylene (—$CH_2$—);

R is C(=O)Z where Z is selected from the group comprising or consisting of hydrogen, hydroxy, alkoxy such as —O-alkyl preferably —O—$C_1$-$C_4$ alkyl (i.e. to provide $C_1$-$C_4$ ester, including methyl, ethyl, propyl or butyl esters) and optionally substituted alkyl preferably $C_1$-$C_6$ alkyl; or R is amino or alkylamine such as —$NR^1R^2$ where $R^1$ and $R^2$ are independently hydrogen or optionally substituted alkyl preferably $C_1$-$C_6$ alkyl having 1 to 6;

n is an integer selected from 0, 1, 2, 3, 4 (where available phenyl ring positions are all hydrogen-substituted) and 5, and preferably n is selected from 0, 1 and 2; and pharmaceutically acceptable salts thereof.

Preferred compounds of Formulae I and II above include those having a para-substituted phenyl moiety as a component of the substituent of the pyrrolidinone ring nitrogen, such as compounds of following Formula III:

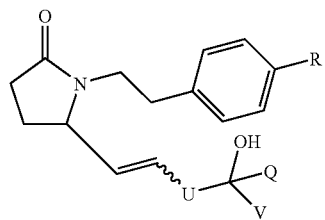

III wherein in Formula III: U, Q and V are the same as defined in Formula I; and R is the same as defined in Formula II; and pharmaceutically acceptable salts thereof.

Also preferred are compounds of the above formulae wherein one of substituents Q and V is hydrogen and the other is a non-hydrogen group, such as compounds of the following Formula IV:

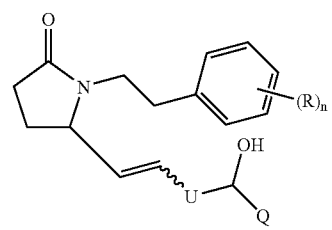

IV wherein in Formula IV:
U is the same as defined in Formula I;
R and n are the same as defined in Formula II; and
Q is selected from the group comprising or consisting of optionally substituted alkyl preferably having 1 to about 12 carbon atoms, optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, optionally substituted arylalkyl and —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted arylalkyl; and pharmaceutically acceptable salts thereof.

Also preferred are compounds of the above formulae where U is absent (p=0), to thereby provide an allylic alcohol, such as compounds of the following Formula V:

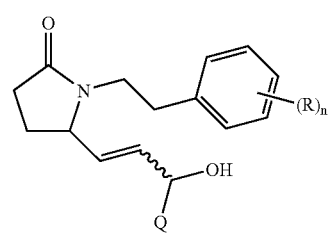

V wherein Formula V:
R and n are the same as defined in Formula II; and
Q is selected from the group comprising or consisting of optionally substituted (straight or branched) alkyl preferably having 1 to about 12 carbon atoms, more preferably from 1 to 9 carbon atoms (e.g. a pentyl, hexyl, heptyl or nonyl moiety), optionally substituted alkenyl preferably having 2 to about 12 carbon atoms, optionally substituted alkynyl preferably having from 2 to about 12 carbon atoms, $C_1$-$C_6$ heteroalkyl, $C_3$-$C_6$ cycloalkyl $C_1$-$C_6$ alkyl, $C_3$-$C_6$ heterocycloalkyl $C_1$-$C_6$ alkyl, optionally substituted arylalkyl, e.g. an optionally substituted benzyl or a phenethyl and —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl $C_1$-$C_6$ alkyl, optionally substituted aryl, optionally substituted heteroaryl and optionally substituted aryl $C_1$-$C_6$ alkyl; and pharmaceutically acceptable salts thereof.

A group of preferred compounds of the invention includes compounds of formula V wherein R is C(=O)OH and is a "para" substituent; n is 1; and pharmaceutically acceptable salts thereof.

Another more preferred group of compounds of the invention includes compounds of formula V wherein R is C(=O)OH and is a "para" substituent;

n is 1;

Q is selected from the group comprising or consisting of optionally substituted $C_1$-$C_6$ alkyl, optionally substituted $C_2$-$C_6$ alkenyl and —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ cycloalkyl, optionally substituted $C_3$-$C_6$ cycloalkyl $C_1$-$C_6$ alkyl, optionally substituted aryl and optionally substituted aryl $C_1$-$C_6$ alkyl; and pharmaceutically acceptable salts thereof.

Another more preferred group of compounds of the invention includes compounds of formula V, wherein R is C(=O)OH is in a "para" position whereby n is 1;

Q is —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl;

W is selected from the group comprising or consisting of hydrogen, optionally substituted $C_1$-$C_6$ alkyl, optionally substituted $C_3$-$C_6$ cycloalkyl $C_1$-$C_6$ alkyl and optionally substituted aryl; and pharmaceutically acceptable salts thereof.

According to one embodiment, the compounds of the invention exhibit binding activity in a standard prostaglandin EP2 receptor binding assay. Exemplary assay is set out in Example 81, which follows.

According to one embodiment, compounds of the present invention also can exhibit selective binding to the EP4 receptor.

As discussed above, substituted 1,2-substituted 5-pyrrolidinone compounds of the invention are useful for treatment of diseases and disorders associated with the prostaglandin family of compounds. Therapeutic methods of the invention in general comprise administering an effective amount of one or more 1,2-substituted 5-pyrrolidinone compounds as disclosed herein to a mammal in need thereof.

1,2-substituted 5-pyrrolidinone compounds of the invention are particularly useful for treatment of a mammal suffering from or susceptible to (prophylactic therapy) pre-term labor, dysmenorrhea, asthma and other conditions treated by bronchodilation, inflammation, hypertension, undesired blood-clotting and other undesired platelet activities, pre-eclampsia and/or eclampsia, and eosinphil-related disorders. 1,2-substituted 5-pyrrolidinone compounds of the invention also are useful to treat a mammal suffering from or suspected of suffering from infertility, particularly a female suffering from infertility. 1,2-substituted 5-pyrrolidinone compounds of the invention may be particularly beneficial for treatment of female mammals suffering from an ovulatory disorder. Additionally, 1,2-substituted 5-pyrrolidinone compounds of the invention can be administered to females undergoing reproductive treatments such as in-vitro fertilization or implant procedures, e.g. to stimulate follicular development and maturation. 1,2-substituted 5-pyrrolidinone compounds of the invention also are useful to treat sexual dysfunction, including erectile dysfunction.

Preferred 1,2-substituted 5-pyrrolidinone compounds of the invention also will be useful for treatment of undesired bone loss (e.g. osteoporosis, particularly in women) or otherwise promoting bone formation and treatment of other bone diseases such as Paget's disease, healing or replacement of bone grafts, and the like.

Compounds of the invention also are useful for treatment of a subject suffering from or susceptible to renal dysfunction, including a mammal suffering from or susceptible to acute or chronic renal failure.

Compounds of the invention also are useful for treatment of a subject suffering from or susceptible to an immune disorder including an immune deficiency disease or disorder, including such a disorder associated with a viral infection particularly a retroviral infection such as an HIV infection. Particularly benefited by such therapies will be a human suffering from or susceptible to AIDS (Thivierge et al. *Blood*, 1998, 92 (1), 40-45).

Compounds of the invention will be further useful to reduce elevated intra-ocular pressure of a subject, e.g. through relaxation of pre-contracted isolated ciliary muscle. In particular, a mammal such as a human suffering from or susceptible to glaucoma or other disorder associated with elevated intra-ocular pressure. Compounds of the invention also will be useful for treatment of a mammal, particularly a human, that is suffering from or susceptible to dry eye.

Compounds of the invention also will be useful for promoting sleep in a subject, e.g. to treat a mammal particularly a human suffering from or susceptible to a sleep disorder such as may be associated with advanced age, such as a human of 65 years or older.

Compounds of the invention also will be useful to treat a mammal suffering from or susceptible to a sexual dysfunction, particularly a human male suffering from erectile dysfunction.

Compounds of the invention also will be useful to treat a amman suddering from or susceptible to an inflammatory disease or disorder including vascular inflammation, inflammatory pain and hyperalgesia.

Compounds of the invention will be further useful to treat a mammal suffering from or susceptible to ulcers, particularly gastric ulcers. Such therapies may be conducted in conjunction with a patient being treated with an anti-inflammatory agent, which can promote gastric ulcers.

Compounds of the invention also may be administered to a mammal particularly a human that is suffering from or susceptible to a skin disorder, particularly dry skin (ichthyosis) or skin rash.

In a further aspect, the invention provides a use of a 1,2-substituted 5-pyrrolidinone compound, including a particularly of any one of Formulae I through V for the treatment or prevention (including prophylactic treatment) of a disease or condition as disclosed herein, including pre-term labor, ovulation induction, cervical ripening, dysmenorrhea, asthma, hypertension, infertility or fertility disorder, undesired blood clotting, pre-eclampsia or eclampsia, an eosinophil disorder, sexual dysfunction including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory diseases or disorders and other diseases and disorders associated with the prostaglandin and receptors thereof.

In a yet further aspect, the invention provides a use of a 1,2-substituted 5-pyrrolidinone compound, particularly a compound of any one of Formulae I through V for the preparation of a medicament for the treatment or prevention (including prophylactic treatment) of a disease or condition as disclosed herein, including pre-term labor, ovulation induction, cervical ripening, dysmenorrhea, asthma, hypertension, infertility or fertility disorder, undesired blood clotting, pre-eclampsia or eclampsia, an eosinophil disorder, sexual dysfunction, including erectile dysfunction, osteoporosis and other destructive bone disease or disorder, renal dysfunction (acute and chronic), immune deficiency disorder or disease, dry eye, skin disorders such as ichthyosis, elevated intra-ocular pressure such as associated with glaucoma, sleep disorders, ulcers, inflammatory diseases or disorders and other diseases and disorders associated with the prostaglandin and receptors thereof Preferred methods of the invention including identifying and/or selecting a subject (e.g. mammal, particularly human) that is susceptible to or suffering from a condition disclosed herein, and thereafter administering to the identified and selected subject one or more compounds of the invention, particularly a subject that is identified and selected as being susceptible to or suffering from infertility, particularly anovulatory disorders, pre-term labor, asthma, hypertension, sexual dysfunction, including erectile dysfunction, osteoporosis and other destructive bone disease or disorder, inflammation, renal dysfunction (acute and chronic), immune deficiency disorder or disease, dry eye, skin disorders such as ichthyosis, elevated intra-ocular pressure such as associated with glaucoma, sleep disorders, ulcers, or other diseases and disorders associated with prostaglandin.

The invention also provides pharmaceutical compositions that comprise one or more 1,2-substituted 5-pyrrolidinone compounds together with a suitable carrier for the compound(s).

In a further aspect, the invention provides methods and pharmaceutical compositions comprising administering a prostaglandin EP4 receptor agonist for the treatment of infertility, including ovulatory disorders. More specifically, the present invention relates to such methods and pharmaceutical compositions for inducing ovulation, including ovulation triggering: more specifically, for triggering ovulation in a patient under a treatment for ovulation induction or under ART (Assisted Reproductive Technology) therapies.

In a yet further aspect, the invention provides methods and pharmaceutical compositions comprising administering a prostaglandin EP4 receptor agonist for the treatment of infertility disorders wherein the EP4 agonist is selected among compounds of following formula VI:

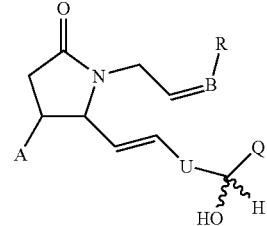

VI wherein A is H or OH, preferably H;

B is selected from the group comprising or consisting of optionally substituted $C_1$-$C_6$ alkyl, preferably $C_3$ or $C_4$ alkyl, optionally substituted aryl $C_1$-$C_6$ alkyl, optionally substituted aryl $C_1$-$C_6$ heteroalkyl, preferably aryl $C_1$-$C_6$ alkoxy, optionally substituted heteroaryl $C_1$-$C_6$ alkoxy, optionally substituted aryl, optionally substituted heteroaryl, optionally substituted $C_3$-$C_6$ cycloalkyl and optionally substituted $C_3$-$C_6$ heterocycloalkyl, provided that when B is optionally substituted aryl, optionally substituted heteroaryl, optionally substituted $C_3$-$C_6$ cycloalkyl and optionally substituted $C_3$-$C_6$ heterocycloalkyl, the undefined bond linking B is a single bond;

The dotted line indicates an optional double bond;

R is C(=O)Z wherein Z is selected from the group comprising or consisting of hydrogen, hydroxy, alkoxy such as —O-alkyl preferably —O—$C_1$-$C_4$ alkyl (i.e. to provide $C_1$-$C_4$ ester, including methyl, ethyl, propyl or butyl esters), optionally substituted alkyl, preferably $C_1$-$C_6$ alkyl and optionally substituted aryl;

or Z is selected from the group comprising or consisting of amino or alkylamine such as —$NR^1R^2$ wherein $R^1$ and $R^2$ are independently selected from hydrogen and optionally substituted alkyl, preferably $C_1$-$C_6$ alkyl, —$NHSO_2R^3$ and —NHC(O)$R^3$ wherein $R^3$ is selected among optionally substituted $C_1$-$C_6$ alkyl and optionally substituted aryl;

or R is optionally substituted heteroaryl, preferably including at least one N atom, including tetrazolyl;

U is $(CH_2)_p$ wherein p is an integer selected from 0, 1 and 2, preferably 0 or 1;

Q is —$CR^4R^5$—W, wherein $R^4$ and $R^5$ are independently selected from H, halogen and optionally substituted $C_1$-$C_6$ alkyl; or $R^4$ and $R^5$ can form an optionally substituted $C_3$-$C_6$ cycloalkyl with the carbon they are attached to, preferably an optionally substituted $C_3$, $C_4$ or $C_5$ cycloalkyl;

W is selected from the group comprising or consisting of hydrogen, optionally substituted $C_1$-$C_6$ alkyl, optionally substituted $C_3$-$C_6$ cycloalkyl, optionally substituted $C_3$-$C_6$ heterocycloalkyl, optionally substituted $C_3$-$C_6$ cycloalkyl $C_1$-$C_6$ alkyl, optionally substituted $C_3$-$C_6$ heterocycloalkyl $C_1$-$C_6$ alkyl, optionally substituted aryl, optionally substituted heteroaryl, optionally substituted aryl $C_1$-$C_6$ alkyl and optionally substituted heteroaryl $C_1$-$C_6$ alkyl; and pharmaceutically acceptable salts thereof.

Preferred said EP4 agonists are selected in an EP4 binding assay. An example of such an assay is defined in Example 83 which follows.

Other aspects of the invention are disclosed infra.

DETAILED DESCRIPTION OF THE INVENTION

Figure 1:
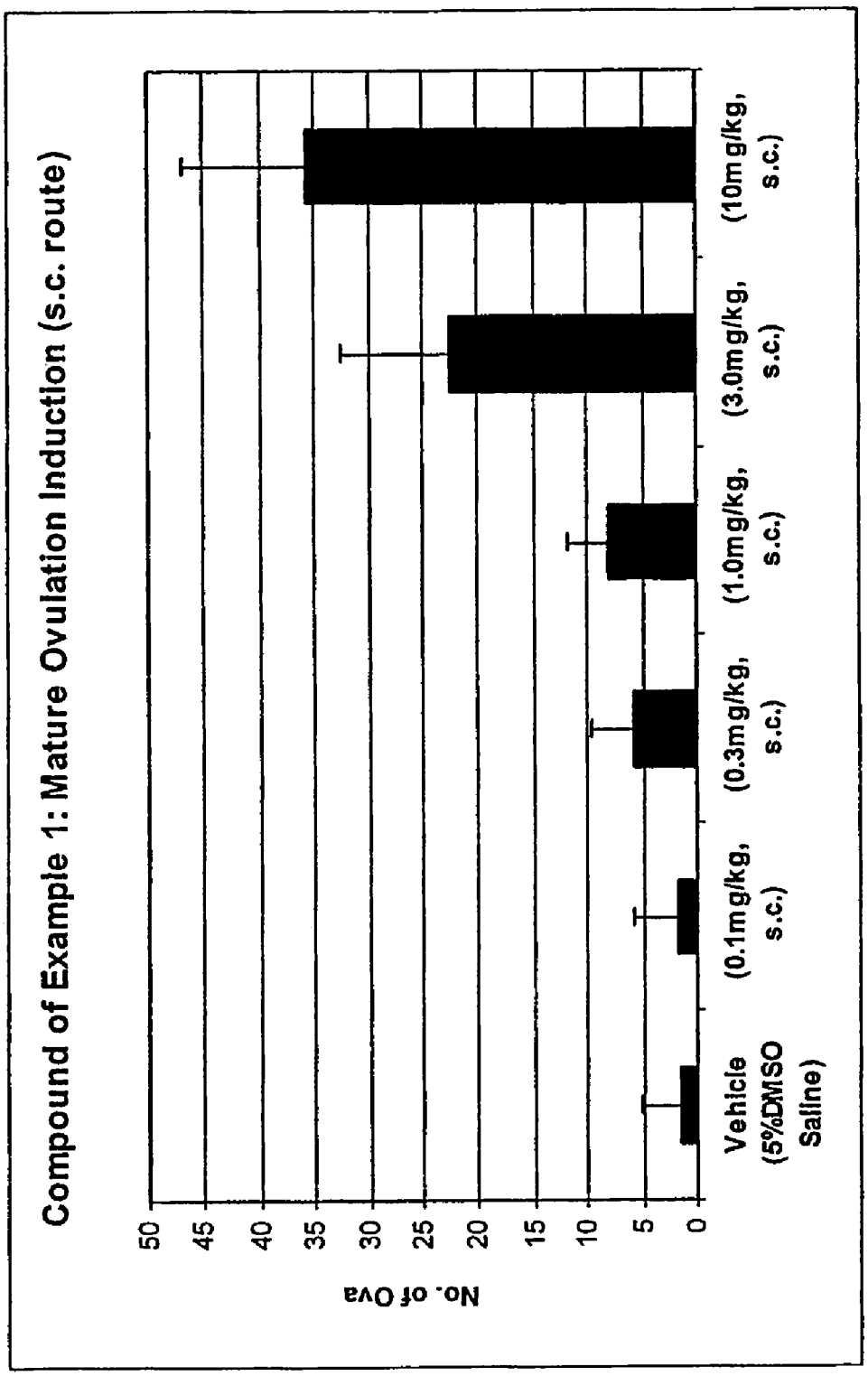
FIG. 1 reports the number of ova released after s.c. injection of compound of Example 1 in mature 10-week CD-1 mice, 48 hours after an injection of 5IU PMSG (i.p.). The number of ova released is shown for different doses of injection of compound of Example 1.

We have now discovered that 1,2-substituted 5-pyrrolidinone compounds of the above Formulae I, II, III, IV and V are useful for treatment of a variety of disorders, particularly diseases and disorders associated with prostaglandins, such as by inhibiting prostanoid-induced smooth muscle contraction.

Suitable alkyl substituent groups of compounds of the invention (which includes compounds of Formulae I, II, III, IV and V as those formulae are defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic as well as branched and straight groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 8 carbon atoms, and still more preferably 1, 2, 3, 4, 5 or 6 carbon atoms. Preferred alkylamino groups include those groups having one or more primary, secondary and/or tertiary amine groups, and from 1 to about 8 carbon atoms, still more preferably 1, 2, 3, 4, 5, or 6 carbon atoms.

Suitable heteroalicyclic groups of compounds of the invention particularly as substituent B as Formula I, contain one or more N, O or S atoms and include, e.g., tetrahydrofuranyl, thienyl, piperidinyl, morpholino and pyrrolidinyl groups.

Suitable heteroaromatic groups of compounds of the invention particularly as substituent B as Formula I are 5-membered or 6-membered single ring moieties having at least N, O or S rings atoms. Particular examples of heteroaromatic groups include optionally substituted pyridyl, pyrrolyl, furyl (furanyl), thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl. Optionally substituted thienyl, optionally substituted furanyl, optionally substituted pyrazinyl and optionally substituted pyridyl are particularly preferred heteroaromatic B substituents.

Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including phenyl, 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,4-substituted phenyl, and 2,5-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused carbocyclic aryl groups. Typical aralkyl groups contain 1 to 3 separate or fused rings and from 6 to about 18 carbon ring atoms. Preferred aralkyl groups include benzyl and naphthylmethyl (—$CH_2$-naphthyl), and other carbocyclic aralkyl groups, as discussed above.

As discussed above, various substituents of the above formulae, such as R, $R^1$, $R^2$, B, V, Q, and Z may be optionally substituted. A "substituted" R, $R^1$, $R^2$, B, V, Q, and Z group or other substituent may be substituted by other than hydrogen at one or more available positions, typically 1 to 3 or 4 positions, by one or more suitable groups such as those disclosed herein. Suitable groups that may be present on a "substituted" R, $R^1$, $R^2$, B, V, Q, and Z group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups including those having one or more oxygen linkages and from 1 to about 12 carbon atoms, or 1, 2, 3, 4, 5 or 6 carbon atoms; aryloxy such as phenoxy; alkylamino groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a preferred group; or aralkoxy having 1 to 3 separate or fused rings and from 6 to about 18 carbon ring atoms, such as O-benzyl. Also comprised by the term optionally substituted shall be situations where at one position of a moiety R, $R^1$, $R^2$, B, V, Q, Z two alkyl substituents undergo ring closure to provide for a cycloalkyl, e.g. a cyclopropyl, moiety.

A particularly preferred embodiment of the invention is the group of pyrrolidine derivatives according to formula V wherein R is —C(O)OH being in a "para" position whereby n is 1.

Another particularly preferred embodiment of the invention includes compounds of formula V, wherein R is —C(O)OH being in a "para" position whereby n is 1;

Q is selected from the group comprising or consisting of optionally substituted $C_1$-$C_6$ alkyl, preferably butyl, pentyl, hexyl, methyl butyl, methyl propyl, di-methyl propyl, di-methyl pentyl or trifluoropropyl, optionally substituted $C_2$-$C_6$ alkenyl, preferably butenyl, optionally substituted $C_2$-$C_6$ alkynyl and —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl, preferably cyclopropyl or cyclobutyl;

W is selected from the group comprising or consisting of hydrogen, optionally substituted $C_1$-$C_6$ alkyl, preferably propyl, butyl, pentyl, methyl-1-ethyl, methyl propyl, tert-butyl or tri-fluoro ethyl, optionally substituted $C_3$-$C_6$ cycloalkyl $C_1$-$C_6$ alkyl, preferably, methyl cyclopropyl, ethyl cyclopropyl, optionally substituted $C_3$-$C_6$ cycloalkyl, preferably cyclopropyl, cyclopentyl or cyclohexyl, optionally substituted aryl, preferably optionally substituted phenyl including phenyl, methyl phenyl, halogeno phenyl and chloro phenyl and optionally substituted aryl $C_1$-$C_6$ alkyl, preferably ethyl phenyl; and pharmaceutically acceptable salts thereof.

Another more preferred group of compounds of the invention includes compounds of formula V wherein R is —C(O)OH being in a "para" position whereby n is 1;

Q is —$CR^1R^2$—W, wherein $R^1$ and $R^2$ are independently selected from H and optionally substituted $C_1$-$C_6$ alkyl, preferably H or methyl; or $R^1$ and $R^2$ can form an optionally substituted $C_3$-$C_6$ cycloalkyl with the carbon they are attached to, preferably an optionally substituted $C_3$ or $C_4$ cycloalkyl, preferably cyclopropyl or cyclobutyl;

W is selected from the group comprising or consisting of hydrogen, optionally substituted $C_1$-$C_6$ alkyl, preferably propyl, butyl, pentyl, optionally substituted $C_3$-$C_6$ cycloalkyl $C_1$-$C_6$ alkyl, preferably methyl cyclopropyl or ethyl cyclopropyl and optionally substituted aryl, preferably optionally substituted phenyl including phenyl and methyl phenyl; and pharmaceutically acceptable salts thereof.

Specifically preferred pyrrolidinones of the invention include the following depicted compounds and pharmaceutically acceptable salts of these compounds:

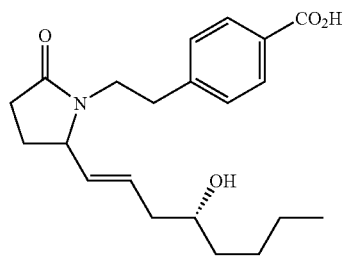

4-(2-{(2R)-2-[(1E,4S)-4-hydroxyoct-1-enyl]-5-oxopyrrolidin-1-yl}ethyl)benzoic acid;

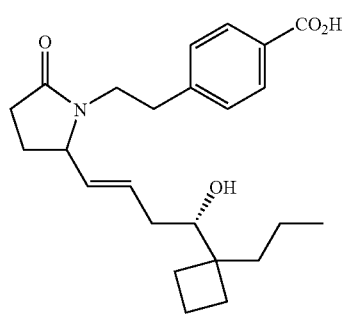

4-(2-{(2R)-2-[(1E,4R)-4-hydroxy-4-(1-propylcyclobutyl)but-1-enyl]-5-oxopyrrolidin-1-yl}ethyl)benzoic acid;

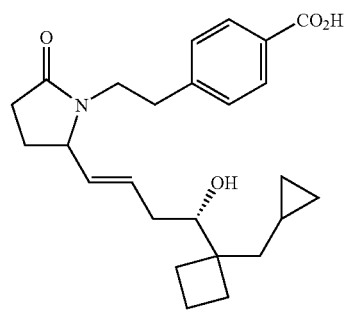

4-[2-((2R)-2-{(1E,4R)-4-[1-(cyclopropylmethyl)cyclobutyl]-4-hydroxybut-1-enyl}-5-oxopyrrolidin-1-yl)ethyl]benzoic acid;

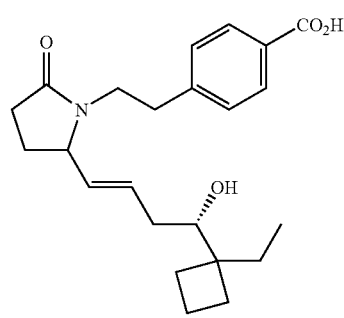

4-(2-{(2R)-2-[(1E,4R)-4-(1-ethylcyclobutyl)-4-hydroxybut-1-enyl]-5-oxopyrrolidin-1-yl}ethyl)benzoic acid;

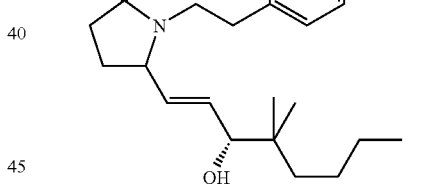

4-(2-{(2R)-2-[(1E,3S)-3-hydroxy-4,4-dimethyloct-1-enyl]-5-oxopyrrolidin-1-yl}ethyl)benzoic acid;

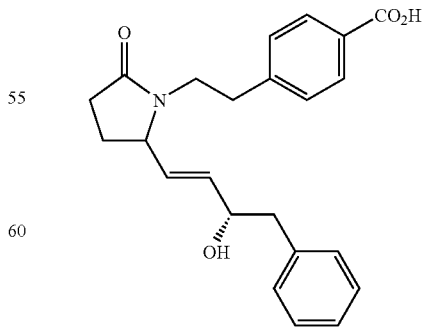

4-(2-{(2R)-2-[(1E,3R)-3-hydroxy-4-phenylbut-1-enyl]-5-oxopyrrolidin-1-yl}ethyl)benzoic acid;

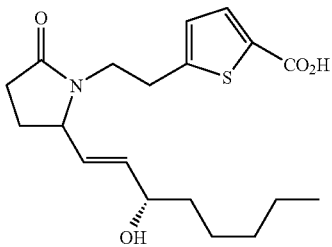

5-(2-{(2R)-2-[(1E,3R)-3-hydroxyoct-1-enyl]-5-oxopyrrolidin-1-yl}ethyl)thiophene-2-carboxylic acid;

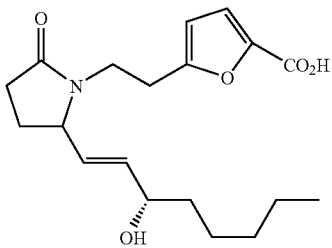

5-(2-{(2R)-2-[(1E,3R)-3-hydroxyoct-1-enyl]-5-oxopyrrolidin-1-yl}ethyl)-2furoic acid;

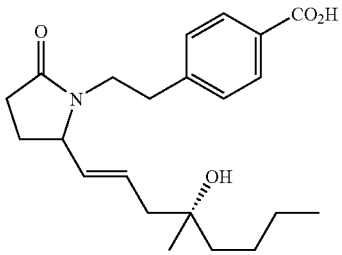

4-(2-{(2S)-2-[(1E,4S)-4-hydroxy-4-methyloct-1-enyl]-5-oxopyrrolidin-1-yl}ethyl)benzoic acid;

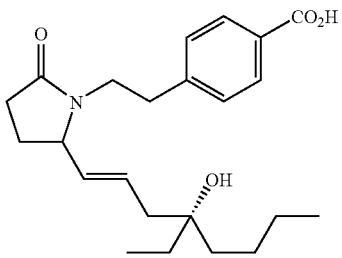

4-(2-{(2S)-2-[(1E,4S)-4-hydroxy-4-ethyloct-1-enyl]-5-oxopyrrolidin-1-yl}ethyl)benzoic acid;
4-(2-{(2R)-2-[(1E,3S)-3-hydroxyoct-1-en-7-ynyl]-5-oxopyrrolidin-1-yl}ethyl)benzoic acid;
4-(2-{(2R)-2-[(1E,3S)-3-hydroxyoct-1-enyl]-5-oxopyrrolidin-1-yl}ethyl)benzamide;
4-(2-{(2R)-2-[(1E,3R)-3-hydroxy-4-phenoxybut-1-enyl]-5-oxopyrrolidin-1-yl}ethyl)benzoic acid;
4-(2-{(2R)-2-[(1E,3R)-4-(allyloxy)-3-hydroxybut-1-enyl]-5-oxopyrrolidin -1-yl}ethyl)benzoic acid;
4(2-{(2R)-2-[(1E,3R,7S)-3,7-dihydroxyoct-1-enyl]-5-oxopyrrolidin-1-yl}ethyl)benzoic acid;
4-(2-{(2R)-2-[(1E,3S,7S)-3,7-dihydroxyoct-1-enyl]-5-oxopyrrolidin-1-yl}ethyl)benzoic acid;
4-(2-{(2R)-2-[(1E,3R,7R)-3,7-dihydroxyoct-1-enyl]-5-oxopyrrolidin-1-yl}ethyl)benzoic acid;
4-(2-{(2R)-2-[(1E)-3-hydroxy-5-morpholin-4-ylpent-1-enyl]-5-oxopyrrolidin-1-yl}ethyl)benzoic acid;
4-(2-{(2R)-2-[(1E,3S)-3-hydroxyhepta-1,6-dienyl]-5-oxopyrrolidin-1-yl}ethyl)benzoic acid;
4-(2-{(2R)-2-[(1E,3S)-4-cyclopropyl-3-hydroxybut-1-enyl]-5-oxopyrrolidin-1-yl}ethyl)benzoic acid;
4-(2-{(2R)-2-[(1E,3R)-4-cyclopentyl-3-hydroxybut-1-enyl]-5-oxopyrrolidin-1-yl}ethyl)benzoic acid;
4-(2-{(2R)-2-[(1E,3S)-4-cyclopentyl-3-hydroxybut-1-enyl]-5-oxopyrrolidin-1-yl}ethyl)benzoic acid;
4-(2-{(2R)-2-[(1E,3R)-4-cyclopropyl-3-hydroxybut-1-enyl]-5-oxopyrrolidin-1-yl}ethyl)benzoic acid
4-(2-{(2R)-2-[(1E,3S)-3-hydroxy-6-methylhept-1-enyl]-5-oxopyrrolidin-1-yl}ethyl)benzoic acid;
4-(2-{(2R)-2-[(1E,3S)-3-hydroxy-5-methylhex-1-enyl]-5-oxopyrrolidin-1-yl}ethyl)benzoic acid;
4-(2-{(2R)-2-[(1E,3S)-3-hydroxy-5,5-dimethylhex-1-enyl]-5-oxopyrrolidin-1-yl}ethyl)benzoic acid;
4-(2-{(2R)-2-[(1E,3S)-6-cyclopropyl-3-hydroxyhex-1-enyl]-5-oxopyrrolidin-1-yl}ethyl)benzoic acid;
4-(2-{(2R)-2-[(1E,3R)-3-hydroxy-5-methoxypent-1-enyl]-5-oxopyrrolidin-1-yl}ethyl)benzoic acid;
4-(2-{(2R)-2-[(1E,3S)-3-hydroxy-5-methoxypent-1-enyl]-5-oxopyrrolidin-1-yl}ethyl)benzoic acid;
4-(2-{(5R)-2-oxo-5-[(1E,3S)-6,6,6-trifluoro-3-hydroxyhex-1-enyl]pyrrolidin-1-yl}ethyl)benzoic acid
4-(2-{(2R)-2-[(1E,3S)-4-cyclohexyl-3-hydroxybut-1-enyl]-5-oxopyrrolidin-1-yl}ethyl)benzoic acid;
4-(2-{(2R)-2-[(1E,3S)-3-hydroxypent-1-enyl]-5-oxopyrrolidin-1-yl}ethyl)benzoic acid;
4-(2-{(2R)-2-[(1E,3S)-3-hydroxyhex-1-enyl]-5-oxopyrrolidin-1-yl}ethyl)benzoic acid;
4-(2-{(2R)-2-[(1E,3S)-3-hydroxy-6-methoxyhex-1-enyl]-5-oxopyrrolidin-1-yl}ethyl)benzoic acid;
4-(2-{(2R)-2-[(1E,3S,7R)-3,7-dihydroxyoct-1-enyl]-5-oxopyrrolidin-1-yl}ethyl)benzoic acid;
4-(2-{(2R)-2-[(1E,3R)-4-(4-chlorophenyl)-3-hydroxy-4-methylpent-1-enyl]-5-oxopyrrolidin-1-yl}ethyl)benzoic acid;
4-[2-((2R)-2-{(1E,3S)-3-[1-(cyclopropylmethyl)cyclobutyl]-3-hydroxyprop-1-enyl}-5-oxopyrrolidin-1-yl)ethyl]benzoic acid;
4-[2-((2R)-2-{(1E,3R)-3-[1-(cyclopropylmethyl)cyclobutyl]-3-hydroxyprop-1-enyl}-5-oxopyrrolidin-1-yl)ethyl]benzoic acid;
4-(2-{(2S)-2-[(3S)-3-(1-butylcyclobutyl)-3-hydroxypropyl]-5-oxopyrrolidin-1-yl}ethyl)benzoic acid;
4-(2-{(2S)-2-[(3R)-3-(1-butylcyclobutyl)-3-hydroxypropyl]-5-oxopyrrolidin-1-yl}ethyl)benzoic acid;
4-(2-{(2R)-2-[(1E,3R)-3-hydroxy-3-(1-phenylcyclopentyl)prop-1-enyl]-5-oxopyrrolidin-1-yl}ethyl)benzoic acid;
4-(2-{(2R)-2-[(1E,3S)-3-hydroxy-3-(1-phenylcyclopentyl)prop-1-enyl]-5-oxopyrrolidin-1-yl}ethyl)benzoic acid;
4-[2-((2R)-2-{(1E,3R)-3-[1-(4-chlorophenyl)cyclopropyl]-3-hydroxyprop-1-enyl}-5-oxopyrrolidin-1-yl)ethyl]benzoic acid;
4-[2-((2R)-2-{(1E,3S)-3-[1-(4-chlorophenyl)cyclobutyl]-3-hydroxyprop-1-enyl}-5-oxopyrrolidin-1-yl)ethyl]benzoic acid;

4-[2-((2R)-2-{(1E,3R)-3-[1-(4-chlorophenyl)cyclobutyl]-3-hydroxyprop-1-enyl}-5-oxopyrrolidin-1-yl)ethyl]benzoic acid;
4-[2-((2R)-2-{(1E,3S)-3-[1-(4-chlorophenyl)cyclopropyl]-3-hydroxyprop-1-enyl}-5-oxopyrrolidin-1-yl)ethyl]benzoic acid;
4-[2-((2R)-2-{(1E,3S)-3-hydroxy-3-[1-(4-methylphenyl)cyclopentyl]prop-1-enyl}-5-oxopyrrolidin-1-yl)ethyl]benzoic acid;
4-[2-((2R)-2-{(1E,3R)-3-hydroxy-3-[1-(4-methylphenyl)cyclopentyl]prop-1-enyl}-5-oxopyrrolidin-1-yl)ethyl]benzoic acid;
4-(2-{(2R)-2-[(1E,3S)-4-(4-chlorophenyl)-3-hydroxy-4-methylpent-1-enyl]-5-oxopyrrolidin-1-yl}ethyl)benzoic acid;
4-[2-((2R)-2-{(1E,3S)-3-[1-(4-fluorophenyl)cyclopentyl]-3-hydroxyprop-1-enyl}-5-oxopyrrolidin-1-yl)ethyl]benzoic acid;
4-[2-((2R)-2-{(1E,3R)-3-[1-(4-fluorophenyl)cyclopentyl]-3-hydroxyprop-1-enyl}-5-oxopyrrolidin-1-yl)ethyl]benzoic acid;
4-[2-((2R)-2-{(1E,3R)-3-[1-(2-fluorophenyl)cyclopentyl]-3-hydroxyprop-1-enyl}-5-oxopyrrolidin-1-yl)ethyl]benzoic acid;
4-[2-((2R)-2-{(1E,3S)-3-[1-(2-fluorophenyl)cyclopentyl]-3-hydroxyprop-1-enyl}-5-oxopyrrolidin-1-yl)ethyl]benzoic acid;
4-[2-((2R)-2-{(1E,3S)-3-[1-(4-chlorophenyl)cyclopentyl]-3-hydroxyprop-1-enyl}-5-oxopyrrolidin-1-yl)ethyl]benzoic acid;
4-[2-((2R)-2-{(1E,3R)-3-[1-(4-chlorophenyl)cyclopentyl]-3-hydroxyprop-1-enyl}-5-oxopyrrolidin-1-yl)ethyl]benzoic acid;
4-(2-{(2R)-2-[(1E,3S)-3-hydroxy-4-(3-methylphenyl)but-1-enyl]-5-oxopyrrolidin-1-yl}ethyl)benzoic acid;
4-(2-{(2R)-2-[(1E,3S)-3-hydroxy-5-phenylpent-1-enyl]-5-oxopyrrolidin-1-yl}ethyl)benzoic acid;
4-(2-{(2R)-2-[(1E,3S)-3-hydroxyhept-1-enyl]-5-oxopyrrolidin-1-yl}ethyl)benzoic acid;
4-(2-{(2R)-2-[(1E,3S)-4-(3-chlorophenyl)-3-hydroxybut-1-enyl]-5-oxopyrrolidin-1-yl}ethyl)benzoic acid;
4-(2-{(2R)-2-[(1E,3S)-3-hydroxy-4-phenylbut-1-enyl]-5-oxopyrrolidin-1-yl}ethyl)benzoic acid;
4-(2-{(2S)-2-[(3R)-3-hydroxy-4-methyl-4-phenylpentyl]-5-oxopyrrolidin-1-yl}ethyl)benzoic acid;
4-(2-{(2R)-2-[(1E,3S)-3-hydroxy-4-methyl-4-phenylpent-1-enyl]-5-oxopyrrolidin-1-yl}ethyl)benzoic acid;
4-(2-{(2R)-2-[(1E,3R)-3-hydroxy-4-methyl-4-phenylpent-1-enyl]-5-oxopyrrolidin-1-yl}ethyl)benzoic acid;
4-(2-{(2S)-2-[(3S)-3-hydroxynonyl]-5-oxopyrrolidin-1-yl}ethyl)benzoic acid;
4-[2-((2R)-2-{(1E,3S)-3-[1-(3-fluorophenyl)cyclopentyl]-3-hydroxyprop-1-enyl}-5-oxopyrrolidin-1-yl)ethyl]benzoic acid;
4-[2-((2R)-2-{(1E,3R)-3-[1-(3-fluorophenyl)cyclopentyl]-3-hydroxyprop-1-enyl}-5-oxopyrrolidin-1-yl)ethyl]benzoic acid;
4-(2-{(2R)-2-[(1E,3S)-3-hydroxynon-1-enyl]-5-oxopyrrolidin-1-yl}ethyl)benzoic acid;
4-[2-((2R)-2-{(1E,3S)-3-hydroxy-3-[1-(2-phenylethyl)cyclobutyl]prop-1-enyl}-5-oxopyrrolidin-1-yl)ethyl]benzoic acid;
4-[2-((2R)-2-{(1E,3R)-3-hydroxy-3-[1-(2-phenylethyl)cyclobutyl]prop-1-enyl}-5-oxopyrrolidin-1-yl)ethyl]benzoic acid;
4-(2-{(2R)-2-[(1E,3S)-3-hydroxy-3-(1-propylcyclobutyl)prop-1-enyl]-5-oxopyrrolidin-1-yl}ethyl)benzoic acid;
4-(2-{(2R)-2-[(1E,3R)-3-hydroxy-3-(1-propylcyclobutyl)prop-1-enyl]-5-oxopyrrolidin-1-yl}ethyl)benzoic acid;
4-(2-{(2R)-2-[(1E,3R)-3-(1-benzylcyclobutyl)-3-hydroxyprop-1-enyl]-5-oxopyrrolidin-1-yl}ethyl)benzoic acid;
4-(2-{(2R)-2-[(1E)-3-hydroxy-3-methyloct-1-enyl]-5-oxopyrrolidin-1-yl}ethyl)benzoic acid;
4-(2-{(2R)-2-[(1E)-4-hydroxyoct-1-enyl]-5-oxopyrrolidin-1-yl}ethyl)benzoic acid;
4-(2-{(2R)-2-[(1E,3S)-3-(1-butylcyclobutyl)-3-hydroxyprop-1-enyl]-5-oxopyrrolidin-1-yl}ethyl)benzoic acid;
4-(2-{(2R)-2-[(1E,3R)-3-(1-butylcyclobutyl)-3-hydroxyprop-1-enyl]-5-oxopyrrolidin-1-yl}ethyl)benzoic acid;
4-(2-{(2R)-2-[(1E,3S)-3-hydroxy-4,4-dimethyloct-1-enyl]-5-oxopyrrolidin-1-yl}ethyl)benzoic acid;
4-(2-{(2R)-2-[(1E,3R)-3-hydroxy-4,4-dimethyloct-1-enyl]-5-oxopyrrolidin-1-yl}ethyl)benzoic acid;
4-(2-{(2R)-2-[(1E,3S)-3-hydroxy-3-(1-phenylcyclopropyl)prop-1-enyl]-5-oxopyrrolidin-1-yl}ethyl)benzoic acid;
4-(2-{(2R)-2-[(1E,3R)-3-hydroxy-3-(1-phenylcyclopropyl)prop-1-enyl]-5-oxopyrrolidin-1-yl}ethyl)benzoic acid;
4-(2-{(2R)-2-[(1E,3S)-3-hydroxy-7-methyloct-1-enyl]-5-oxopyrrolidin-1-yl}ethyl)benzoic acid;
4-(2-{(2R)-2-[(1E,3S)-5-cyclopentyl-3-hydroxypent-1-enyl]-5-oxopyrrolidin-1-yl}ethyl)benzoic acid; or a pharmaceutically acceptable salt of any of said compounds.

As discussed above, preferred compounds of the invention exhibit activity in a prostaglandin EP2 receptor binding assay as described, for example in the protocol of Example 81, which follows. Generally preferred compounds of the invention have a Ki (µM) of about 100 or less, more preferably about 50 or less, still more preferably a Ki (µM) of about 10 or 20 or less, even more preferably a Ki (µM) of about 5 or less in such a prostaglandin assay as exemplified by Example 81 which follows.

1,2-substituted 5-pyrrolidinone compounds of the invention can be readily prepared. Suitable synthetic procedures are exemplified in the following Scheme 1. It should be appreciated that the compounds shown in the following Scheme is exemplary only, and a variety of other compounds can be employed in a similar manner as described below.

In another aspect of the invention, are provided methods and pharmaceutical compositions comprising administering a prostaglandin EP4 receptor agonist for the treatment of infertility, including ovulatory disorders. More specifically, the present invention relates to such methods and pharmaceutical compositions for inducing ovulation, particularly ovulation triggering; more specifically, the present invention relates to such methods and pharmaceutical compositions for triggering ovulation in patients under ovulation induction or ART treatments.

The term "EP4 receptor agonist" refers to a compound, including its isomers, pro-drugs and pharmaceutically acceptable salts, which bind to the prostaglandin EP4 sub-type receptor. A prostaglandin EP4 sub-type agonist can be identified by several conventional assays, including a prostaglandin EP4 binding assay and a cyclic AMP assay on cells over-expressing EP4 receptor. Other appropriate conventional assays may be used by the skilled person in the art for selecting EP4 agonists.

Preferred prostaglandin EP4 receptor agonists exhibit activity in a prostaglandin EP4 receptor binding assay, an example thereof is defined in the protocol as defined in Example 83, which follows.

A particularly preferred group of EP4 receptor agonists of the invention have a Ki (nM) of about 20 or less, more preferably about 10 or less, still more preferably a Ki (nM) of about 5 or 2 or less, even more preferably a Ki (nM) of about 1 or less, further more preferred, a Ki (nM) of about 0.1 or less in a prostaglandin EP4 receptor binding assay as exemplified by Example 83 which follows.

Other preferred prostaglandin EP4 receptor agonists exhibit activity in a cAMP assay on cell lines over-expressing EP4 receptor, an example thereof is defined in the protocol as defined in Example 84, which follows.

Another particularly preferred group of EP4 receptor agonists of the invention have a $EC_{50}$ (nM) of about 30 or less, more preferably about 20 or less, still more preferably a $EC_{50}$ (nM) of about 10 or 5 or less, even more preferably a $EC_{50}$ (nM) of about 1 or 0.1 less in such a cAMP/EP4 receptor as exemplified by Example 84 which follows.

In a further embodiment of the invention, the selective EP4 receptor agonists used for triggering ovulation can be selected from EP4 agonists described in the art that have the preferred EP4 activities mentioned above in EP4 assays. For example, EP4 selective agonists can be selected from EP4 agonists described in WO 03/035064, preferably 4-[2-(2-{3-hydroxy-4-[3-(trifluoromethyl)phenyl]butyl}-5-oxopyrazolidin-1-yl)ethyl]benzoic acid and 4-(2-{2-[4-(3-iodophenyl)-3-hydroxybutyl]-5-oxopyrazolidin-1-yl}ethyl)benzoic acid.

In one embodiment of the invention, the said method for inducing ovulation is a method wherein said EP4 agonist is selected among compounds of Formula VI, wherein the substituents A, B, D, R, U, Q, W, $R^1$, $R^2$, $R^3$, $R^4$ and $R^5$ are the same as defined in Formula VI above.

In one preferred embodiment of the invention, the said method for triggering ovulation for ovulation induction or ART is a method wherein said EP4 agonist is selected among compounds of formula VI, wherein A is H; B is optionally substituted $C_1$-$C_6$ alkyl, preferably butyl; D is a double bond; R is C(=O)Z wherein Z is selected from hydrogen, hydroxy, alkoxy such as —O-alkyl preferably —O—$C_1$-$C_4$ alkyl (i.e. to provide $C_1$-$C_4$ ester, including methyl, ethyl, propyl or butyl esters) and optionally substituted alkyl, preferably $C_1$-$C_6$ alkyl; or Z is selected from amino or alkylamine such as —$NR^1R^2$ where $R^1$ and $R^2$ are independently hydrogen or optionally substituted alkyl, preferably $C_1$-$C_6$ alkyl, —$NHSO_2R^3$ and —NHC(O)$R^3$ wherein $R^3$ is selected among optionally substituted $C_1$-$C_6$ alkyl and optionally substituted aryl; U is $(CH_2)_p$ wherein p is 0; Q is —$CR^4R^5$—W, wherein $R^4$ and $R^5$ are independently selected from H, halogen and optionally substituted $C_1$-$C_6$ alkyl; W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the said method for triggering ovulation for ovulation induction or ART is a method wherein said EP4 agonist is selected among compounds of formula VI, wherein A is H; B is optionally substituted $C_1$-$C_6$ alkyl, preferably $C_3$ or $C_4$ alkyl; D is single or cis double bond; R is C(=O)Z wherein Z is selected from hydrogen, hydroxy, alkoxy such as —O-alkyl, preferably —O—$C_1$-$C_4$ alkyl (i.e. to provide $C_1$-$C_4$ ester, including methyl, ethyl, propyl or butyl esters); or R is optionally substituted heteroaryl, preferably including at least one N atom, including tetrazolyl; U is $(CH_2)_p$ wherein p is 0; Q is —$CH_2$—W, wherein W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the said method triggering ovulation for ovulation induction or ART is a method wherein said EP4 agonist is selected among compounds of formula VI, wherein A is H; B is selected from optionally substituted aryl $C_1$-$C_6$ alkoxy, preferably aryloxy, most preferably phenyloxy, optionally substituted —$CH_2$-aryl and optionally substituted —$CH_2$-heteroaryl; D is a single bond; R is C(=O)Z wherein Z is selected hydrogen, hydroxy and alkoxy such as —O-alkyl, preferably —O—$C_1$-$C_4$ alkyl (i.e. to provide $C_1$-$C_4$ ester, including methyl, ethyl, propyl or butyl esters); or R is optionally substituted heteroaryl, preferably including at least one N atom, including tetrazolyl; U is $(CH_2)_p$ wherein p is 0; Q is —$CH_2$—W, wherein W is selected from optionally substituted $C_3$-$C_6$ cycloalkyl, optionally substituted $C_3$-$C_6$ heterocycloalkyl, optionally substituted aryl and optionally substituted heteroaryl; and pharmaceutically acceptable salts thereof.

In another preferred embodiment of the invention, the said method for triggering ovulation for ovulation induction or ART is a method wherein said EP4 agonist is selected among compounds of formula VI, wherein A is H; B is optionally substituted aryl, preferably phenyl; D is a single bond; R is C(=O)Z wherein Z is hydroxy; U is $(CH_2)_p$ wherein p is 0; Q is —$CR^4R^5$—W, wherein $R^4$ and $R^5$ are independently selected from H and optionally substituted $C_1$-$C_6$ alkyl, preferably H or methyl; or $R^4$ and $R^5$ can form an optionally substituted $C_3$-$C_6$ cycloalkyl with the carbon they are attached to, preferably an optionally substituted $C_3$ or $C_4$ cycloalkyl; W is selected from optionally substituted $C_1$-$C_6$ alkyl, preferably methyl propyl, butyl, pentyl, optionally substituted $C_3$-$C_6$ cycloalkyl $C_1$-$C_6$ alkyl, preferably methyl cyclopropyl, ethyl cyclopropyl, optionally substituted $C_3$-$C_6$ cycloalkyl, preferably cyclopropyl, cyclopentyl, optionally substituted aryl, preferably optionally substituted phenyl; and pharmaceutically acceptable salts thereof.

Specifically preferred EP4 agonists of the invention for triggering ovulation for ovulation induction or ART, include the following depicted compounds and pharmaceutically acceptable salts of these compounds:

4-(2-{(2R)-2-[(1E,3S)-3-hydroxy-4-phenylbut-1-enyl]-5-oxopyrrolidin-1-yl}ethyl)benzoic acid;

4-(2-{(2R)-2-[(1E,3S)-4-(3-chlorophenyl)-3-hydroxybut-1-enyl]-5-oxopyrrolidin-1-yl}ethyl)benzoic acid;

4-(2-{(2R)-2-[(1E,3R)-3-hydroxy-3-(1-phenylcyclopropyl)prop-1-enyl]-5-oxopyrrolidin-1-yl}ethyl)benzoic acid;

4-(2-{(2R)-2-[(1E,3S)-6-cyclopropyl-3-hydroxyhex-1-enyl]-5-oxopyrrolidin-1-yl}ethyl)benzoic acid;

4-(2-{(2R)-2-[(1E,3S)-3-hydroxyhepta-1,6-dienyl]-5-oxopyrrolidin-1-yl}ethyl)benzoic acid;

4-(2-{(2R)-2-[(1E,3S)-3-(1-butylcyclobutyl)-3-hydroxyprop-1-enyl]-5-oxopyrrolidin-1-yl}ethyl)benzoic acid;

4-(2-{(2R)-2-[(1E,3S)-3-hydroxy-6-methylhept-1-enyl]-5-oxopyrrolidin-1-yl}ethyl)benzoic acid;

4-[2-((2R)-2-{(1E,3R)-3-[1-(cyclopropylmethyl)cyclobutyl]-3-hydroxyprop-1-enyl}-5-oxopyrrolidin-1-yl)ethyl] benzoic acid;

4-(2-{(2R)-2-[(1E,3S)-3-hydroxyoct-1-enyl]-5-oxopyrrolidin-1-yl}ethyl)benzoic acid;

4-(2-{(2R)-2-[(1E,3R)-3-(1-butylcyclobutyl)-3-hydroxyprop-1-enyl]-5-oxopyrrolidin-1-yl}ethyl)benzoic acid;

4-(2-{(2R)-2-[(1E,3R)-3-hydroxy-4,4-dimethyloct-1-enyl]-5-oxopyrrolidin-1-yl}ethyl)benzoic acid;

4-(2-{(2R)-2-[(1E,3S)-3-hydroxynon-1-enyl]-5-oxopyrrolidin-1-yl}ethyl)benzoic acid;

4-(2-{(2S)-2-[(3R)-3-hydroxy-4-(3-methylphenyl)butyl]-5-oxopyrrolidin 1-yl}ethyl)benzoic acid;

4-(2-{(2S)-2-[(3R)-3-hydroxy-5-phenylpentyl]-5-oxopyrrolidin-1-yl}ethyl)benzoic acid;

or a pharmaceutically acceptable salt of any of said compounds

The term "$C_1$-$C_6$-alkyl" refers to monovalent branched or unbranched alkyl groups having 1 to 6 carbon atoms. This term is exemplified by groups such as methyl, ethyl, n-propyl, isopropyl, n-butyl, isobutyl, tert-butyl, n-hexyl and the like. By analogy, the term "$C_1$-$C_4$-alkyl" refers to monovalent branched or unbranched alkyl groups having 1 to 4 carbon atoms. This term is exemplified by groups such as methyl, ethyl, n-propyl, isopropyl, n-butyl, isobutyl, tert-butyl and the like.

The term "$C_1$-$C_6$-heteroalkyl", refers $C_1$-$C_6$-alkyl according to the definition above, in which at least one carbon atom is replaced by heteroatoms chosen from the group consisting of O, S, NR, R being defined as hydrogen or methyl. Preferred $C_1$-$C_6$-heteroalkyl include methoxy methyl, methoxyethyl, methoxybutyl, and the like.

The term "$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

The term "$C_2$-$C_6$-alkynyl" refers to alkynyl groups preferably having from 2 to 6 carbon atoms and having at least 1-2 sites of alkynyl unsaturation, preferred alkynyl groups include ethynyl, (—C≡CH), propargyl (—$CH_2$C≡CH), and the like.

The terms "$C_2$-$C_6$-heteroalkenyl" and "$C_2$-$C_6$-heteroalkynyl" refers respectively to $C_2$-$C_6$-alkenyl and $C_2$-$C_6$-alkynyl, in which at least one carbon atom is replaced by heteroatoms chosen from the group consisting of O, S, NR, R being defined as hydrogen or methyl. Examples of $C_2$-$C_6$-heteroalkenyl include methoxy propenyl, methoxy butenyl, and the like. Examples of $C_2$-$C_6$-heteroalkynyl include methoxy propynyl, methoxy butynyl, and the like.

The term "$C_3$-$C_6$-cycloalkyl" refers to saturated carbocyclic rings having 3 to 6 carbon atoms. Examples include cyclopropyl, cyclobutyl, cyclopentyl, cyclohexyl, cyclohexenyl and the like.

The term "$C_3$-$C_8$ heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

The term "$C_3$-$C_6$ Cycloalkyl $C_1$-$C_6$-alkyl" refers to $C_1$-$C_6$-alkyl groups, as defined above, having saturated carbocyclic rings having 3 to 6 carbon atoms as substituent. Examples include ethyl cyclobutyl, cyclopropylmethyl cyclobutyl and the like.

The term "Aryl" refers to aromatic carbocyclic groups of from 6 to 14 carbon atoms having a single ring (e.g. phenyl) or multiple condensed rings (e.g. naphthyl). Examples include phenyl, naphthyl, phenanthrenyl and the like.

The term "Aryl $C_1$-$C_6$-alkyl" refers to $C_1$-$C_6$-alkyl groups having an aryl substituent, including benzyl, phenethyl and the like.

The term "Enantiomeric excess" (ee) refers to the percent excess of the enantiomer over the racemate in a mixture of a pure enantiomer (R or S) and a racemate (RS) as defined below.

$$ee=100\%\times(|R-S|)/(R+S)=|\%\,R-\%\,S|$$

where R represents the number of moles of R enantiomer in the sample and S represents the number of moles of S enantiomer in the sample, and |R−S| represents the Absolute Value of the difference of R and S. Compounds of the invention can be obtained in an "Enantiomeric excess" by a synthesis comprising an enantioselective step or can be isolated by for example, crystallization or chiral HPLC.

A particularly preferred embodiment includes compounds of the invention in an enantiomeric excess of the S enantiomer, of at least at or about 50, 70, 80 or 90%, with degree of preference increasing with the increasing ee of the S enantiomer.

In the absence of an enantiomeric synthesis, racemic products are usually obtained that do however also have the inventive set out activity as EP2 and/or EP4 agonists.

The term "pro-drug" refers to compounds that are drug precursors which, following administration, release the drug in vivo via some chemical or physiological process.

The term "EP4 agonist" refers to a compound, including its isomers, pro-drugs and pharmaceutically acceptable salts, which bind to prostaglandin E4 subtype receptor. Such property can be readily determined by those skilled in the art (for example, see Boie, Y. et al Eur. J. Pharmacol. 1997, 340, 227-241 or Abramovitz M. et al Biochim at Biophysica Acta 2000, 1483, 285-293). A variety of such compounds are described and referenced herein. However, other prostaglandin EP4 agonists will be known to those skilled in the art. Exemplary EP4 agonists are disclosed as follows.

The term "selective binding to the EP4 receptor" refers to compounds that are selective is in comparison to the other prostaglandin receptors, particularly EP1 and/or EP3, optionally EP2. Selectivity in this connection means that the affinity of the compounds of the invention for the EP4 receptor is at least more than 5 times higher than the affinity for EP1 receptor and/or EP3 receptor, optionally EP2 receptor, especially more than 10 times and in particular more than 100 or 1000 times the affinity for other prostaglandin receptors like EP1 or EP3 and at least more than 5 times, especially more than 10 times the affinity for the EP2 receptor.

The term "fertility condition(s)" also refers to a condition, particularly infertility, of a female mammal, especially a female patient. This condition includes conditions where ovulation triggering is needed. Examples of female patients in such a condition are female undergoing a treatment for ovulation induction or an Assisted Reproductive Technology (ART) therapies.

The term "ovulation induction" (OI), refers to the stimulation of release of an oocyte (occasionally two or three oocytes) into the fallopian tubes of a female patient, for in vivo fertilisation. OI is used in anovulatory patients [for example, WHO group I patients (hypogonadotrophic hypogonadism) and WHO group II anovulation (hypothalamic-pituitary dysfunction resulting in arrested or attenuated gonadal function), including patients suffering from polycystic ovarian syndrome (PCOS)]. It is usually desired to stimulate the release of a single oocyte, in order to avoid the risks associated with multiple pregnancies. In a typical ovulation induction regimen, the patient is administered FSH, an analogue of FSH or a molecule stimulating endogenous FSH production to stimulate follicular growth for several days until at least one follicle is observed (by ultrasound) with a mean diameter of approximately 17 mm or greater. At this stage, an ovulation trigger (hCG) is given to stimulate rupture of the follicle and release of an oocyte into the fallopian tube ("ovulation triggering"). The molecules of the invention can replace or supplement the ovulation triggering dose of hCG in an OI regimen.

The term "Assisted Reproduction Technology" includes for example, in vitro fertilisation (IVF), and intracytoplasmic sperm injection (ICSI). Oocytes are harvested from mature follicles immediately before rupture, and graded before being fertilised in vitro by combination with sperm.

The resulting embryos are graded for quality, and usually 2 to 3 are selected for placement in the uterus (remaining embryos can be cryopreserved for future attempts). Because of the many factors involved in establishing an ongoing pregnancy, many patients must have oocytes placed in the uterus multiple times before success is achieved. Because of this, in contrast to OI regimens, for ART it is desired to harvest multiple oocytes, in order to maximise the chances of successful pregnancy. The controlled development of multiple preovulatory follicles by administration of exogenous agents capable of inducing follicular growth (such as FSH) is called controlled ovarian hyperstimulation (COH). When there are at least 3 follicles with a mean diameter greater than 16 mm, ovulation is triggered (hCG bolus). Oocytes are usually recovered from pre-ovulatory follicles, by aspiration. The molecules of the invention can replace or supplement the ovulation triggering dose of hCG in an ART regimen.

The invention will be described below by means of the following Examples, which should not be construed as in any way limiting the present invention. The Examples will refer to the Figures specified here below.

Abbreviations

The following abbreviations are hereinafter used in the accompanying examples: min (minute), hr (hour), i.p. (intra-peritoneal), i.v. (intra-venous), mg (milligram), mmol (millimole), mM (millimolar), mM (nanomolar), eq (equivalents), mL (milliliter), µl (microliters), ACN (acetonitrile), BP (mean arterial pressure), BSA (Bovine Serum Albumin), cAMP (Cyclic adenosine monophosphate), DCM (dichloromethane), DMSO (dimethylsulfoxide), EtOAc (ethyl acetate), FBS (Foetal Bovine Serum), GP (Guinea Pig), hCG (human Chorionic Gonadotropin), HR (heart rate), IT (intratracheal), LPS (lipopolysaccharides), MES (2-[N-morpholino]ethanesulfonic acid), MgSO$_4$ (magnesium sulfate), NP3S(N-methyl-pyrrolidinone), PBS (Phosphate buffered saline), PEG (Polyethylene Glycol), PGE1 (Prostaglandin E1), PGE2 (Prostagalndin E2), PMSG (pregnant mare serum gonadotrophin), p.o. (per os, oral administration), PVT (polyvinyltoluene), PSS (physiologic salt solution), RT (room temperature), SPA (Scintillation proximity Assay), TFA (trifluoroacetic acid), THF (tetrahydrofuran), TNF (Tumour Necrosis factor).

Synthesis of Compounds of the Invention

Compounds of the invention can be readily prepared from readily available starting materials using the following general methods and procedures.

Suitable synthetic procedures are exemplified in the following illustrative Scheme 1. It should be appreciated that the compounds shown in the following Scheme are exemplary only, and a variety of other compounds can be employed in a similar manner as described below.

For instance, compounds having non-hydrogen substituents at 4 and 5 ring positions can be provided using a starting reagent having such substitution. It will also be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used. Such conditions can be determined by the person skilled in the art, using routine optimisation procedures.

General protocol:

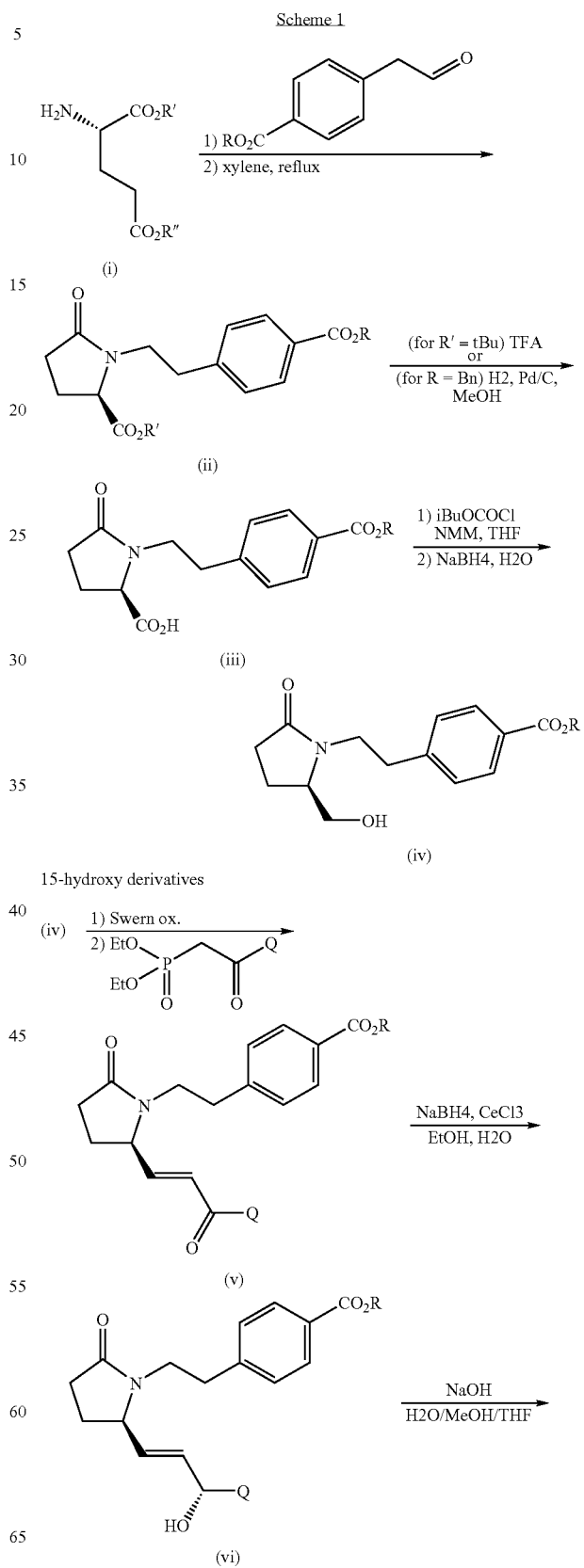

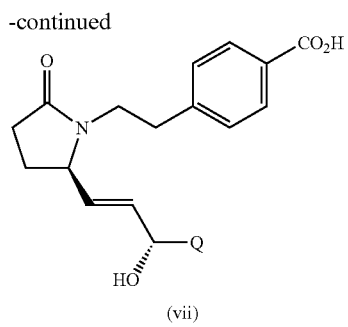

16-hydroxy derivatives

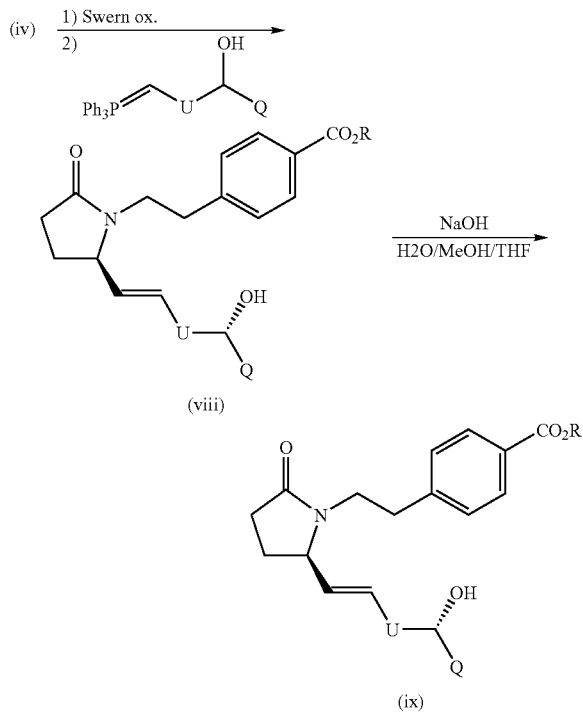

Referring to Scheme 1 above, synthesis of the 15-hydroxy and 16-hydroxy γ-lactam derivatives can be suitably obtained as outlined above using common intermediate (iv). That intermediate (iv) can be synthesized starting from the commercially available Glu derivative (i). The amino groups can be suitably alkylated e.g. by reductive alkylation reaction using the appropriate aldehyde (e.g. a carboxyphenylacetaldehyde, like 4-carbomethoxyphenylacetaldehyde) and NaCNBH$_3$ or other suitable reducing agent. The crude residue is then suitably refluxed in a suitable solvent such as xylene to afford the desired γ-lactam derivative (ii). Selective deprotection of the ester group directly attached to the γ-lactam ring can be obtained by acid treatment (when H-D-Glu(O$^t$Bu)-O$^t$Bu is used) or catalytic hydrogenation (when H-D-Glu(OBn)-OBn is used). Reduction of the acid (iii) to the corresponding alcohol (iv) can be accomplished by reduction e.g. with NaBH$_4$ of the correspondent acyl tert-butyl carbonate intermediate.

Synthesis of the 15-hydroxy derivatives of general formula (vii) can be suitably accomplished as follows. Alcohol intermediate (iv) is suitably oxidized e.g. via Swern reaction to provide the desired aldehyde. That aldehyde then can react with a suitable Wittig reagent particularly an appropriate diethyl 2-oxoalkylphosphonate (for synthesis of the phosphonate intermediate see *J. Org. Chem.* 1998, 63, 8894) to afford the alkene (v). The ketone group then can be reduced e.g. using NaBH$_4$ and CeCl$_3$ to afford the desired alcohol (vi). as a mixture of diastereoisomers. Reduction can proceed in high yields. Chiral reduction of the enone intermediate can be accomplished in good yield and good diastereoselectivity by using (R)-2-methyl-CBS-oxazaborolidine reagent and BH$_3$ complexed with THF (J. Am. Chem. Soc. 1987, 109, 7925-7926) or other hydride reducing agent like N,N-diethylaniline borane (Org. Proc. Res. Dev. 2002, 6, 146-148) using THF or other suitable solvents. Saponification of the ester group e.g. using NaOH in MeOH/water/THF can provide desired product (vii).

γ-Lactam derivatives having the hydroxyl group in position 16 (ix) can be suitably obtained by oxidation of the alcohol (iv) followed by Wittig reaction using the desired (3-hydroxyalkyl)(triphenyl)phosphonium salt (for synthesis of the phosphorane intermediate see *Tetrahedron* 1998, 54, 4243 or *Chem. Lett.* 1991, 113). Saponification of the ester group e.g. using NaOH in MeOH/water/THF can provide the desired product (ix).

Synthesis of 4-hydroxy-pyrrolidin-2-one derivatives (A=OH) could be accomplished by following the procedure described below in Scheme 2.

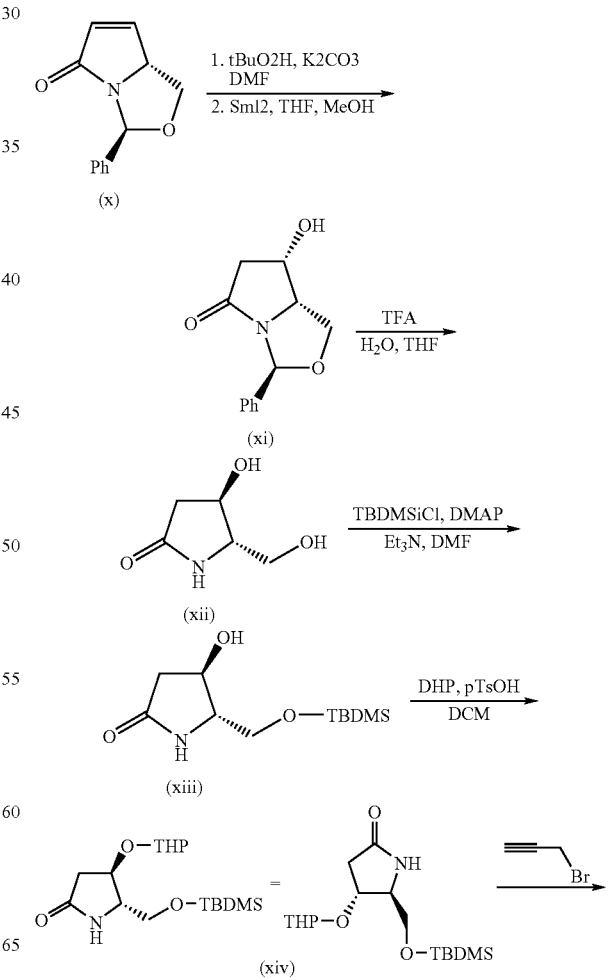

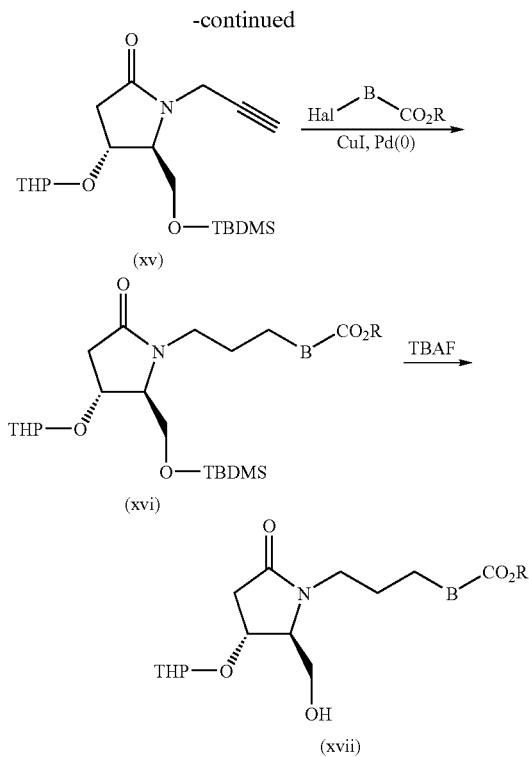

Diastereospecific epoxidation of the rigid bicyclic α,β-unsaturated lactam (x) (Tetrahedrom Letters 1991, 32, 1379-1380) in DMF with tert-butylhydroperoxide in the presence of K$_2$CO$_3$ provide the epoxide intermediate. The 7-hydroxy-3-phenyltetrahydro-5H-pyrrolo[1,2-c][1,3]oxazol-5-one (xi) was obtained by regiospecific opening of the epoxide ring with SmI$_2$ at lower temperature (Tetrahedron letters 2000, 41, 8285-8288). This alcohol derivative is deprotected to the diol (xii) under suitable acidic conditions (e.g. TFA in THF). Suitable protection of the primary alcohol is obtained by using TBDMSiCl, DMAP or other suitable catalyst, Et$_3$N, in DMF or other suitable solvents. Protection of the secondary alcohol can be obtained by reaction of the pyrrolidinone derivative (xiii) with DHP, p-TsOH or other suitable acid catalysts. The pyrrolidinone derivative (xiv) could then be alkylated using propargyl bromide in the presence of a suitable base like K$_2$CO$_3$ and using as solvent acetone or other suitable solvents. Catalytic addition suitable halo-aryl esters can be accomplished using CuI and Pd (0) (Org. Lett. 2000, 2, 1729). Selective deprotection of the primary alcohol to afford intermediate (xvii) can be accomplished by using tetrabutyl ammonium fluoride or other suitable acid or nucleophilic reagents.

Synthesis of the 15-hydroxy derivatives of general formula (xx) can be suitably accomplished as described in Scheme 3 below.

Alcohol intermediate (xvii) is suitably oxidized e.g. via Swern reaction to provide the desired aldehyde. That aldehyde then can react with a suitable Wittig reagent particularly an appropriate diethyl 2-oxoalkylphosphonate (for synthesis of the phosphonate intermediate see *J. Org. Chem.* 1998, 63, 8894) to afford the alkene (xviii). The ketone group then can be reduced e.g. using NaBH$_4$ and CeCl$_3$ to afford the desired alcohol (xix) as a mixture of diastereoisomers. Reduction can proceed in high yields. Chiral reduction of the enone intermediate can be accomplished in good yield and good diastereoselectivity by using (R)-2-methyl-CBS-oxazaborolidine reagent and BH$_3$ complexed with THF (J. Am. Chem. Soc. 1987, 109, 7925-7926) or other hydride reducing agent like N,N-diethylaniline borane (Org. Proc. Res. Dev. 2002, 6, 146-148) using THF or other suitable solvents. Acidic treatment (e.g. HCl in MeOH) followed by saponification of the ester group e.g. using NaOH in MeOH/water/THF can provide desired product (xx).

γ-Lactam derivatives having the hydroxyl group in position 16 (xxi) can be suitably obtained as described in Scheme 4a below by oxidation of the alcohol (xvii) followed by Wittig reaction using the desired (3-hydroxyalkyl)(triphenyl)phosphonium salt (for synthesis of the phosphorane intermediate see *Tetrahedron* 1998, 54, 4243 or *Chem. Lett.* 1991, 113).

Scheme 3

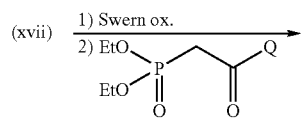

Scheme 4a

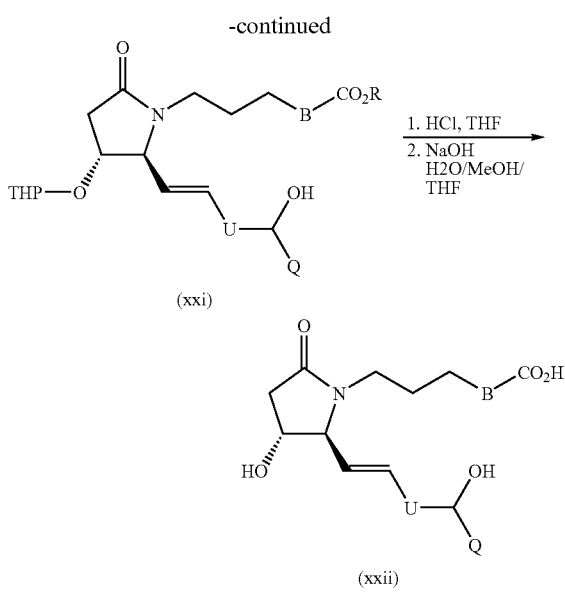

Acidic treatment (e.g. HCl in MeOH) followed by saponification of the ester group e.g. using NaOH in MeOH/water/TBF can provide desired product (xxii).

Synthesis of the 16-hydroxyl pyrrolidinone derivatives (U=CH$_2$) can also be accomplished using the Julia olfination reaction as described in Scheme 4b below.

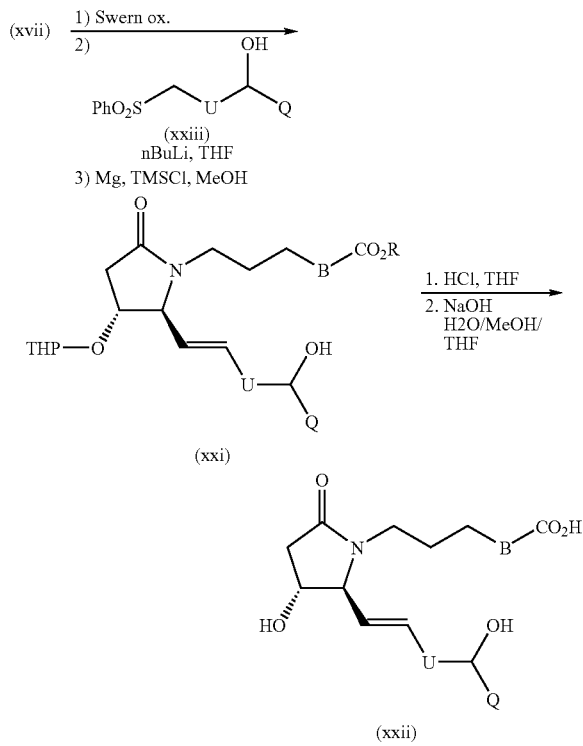

Julia olefination of the aldehyde derived from oxidation of the alcohol intermediate (xvii) with the desired phenyl sulfone derivatives (xxiii) (for synthesis of the sulfone intermediate see Synlett 2002, 1, 239-242) gave the olefine intermediate (xxi). Acidic treatment (e.g. HCl in MeOH) followed by saponification of the ester group e.g. using NaOH in MeOH/water/THF can provide desired product (xxii).

Additional preferred syntheses of compounds of the invention are detailed in the examples which follow.

As indicated above, the present invention includes methods for treating or preventing prostaglandin mediated or associated diseases or disorders.

Preferred therapeutic methods of the invention include inhibiting undesired smooth muscle contraction, including undesired prostanoid-induced smooth muscle contraction. Methods of the invention include treatment of a patient suffering from or susceptible to dysmenorrhea, premature labor, asthma and other conditions that can be relieved by bronchodilation, inflammation, hypertension, undesired blood-clotting (e.g. to reduce or prevent thromboses) and other undesired platelet activities, preeclampsia and/or eclampsia and eosinophil-related disorders (eosinophil disorders).

Treatment and/or prevention of undesired blood clotting may include treatment and prophylaxis of venous thrombosis and pulmonary embolism, arterial thrombosis e.g. myocardial ischemia, myocardial infarction, unstable angina, stroke associated with thrombosis, and peripheral arterial thrombosis. Compounds of the invention also may be useful for anti-coagulation involving artificial organs, cardiac valves, medical implementation (e.g. an indwelling device such as a catheter, stent, etc.) and the like.

The invention also includes methods for treatment of infertility, which generally comprise administration of one or more pyrrolidine compounds of the invention to a mammal, particularly a primate such as a human, suffering from or suspected of suffering from infertility. See the *Merck Manual*, vol. 2, pages 12-17 (16$^{th}$ ed.) for identification of patients suffering from or suspected of suffering from infertility, which in the case of humans, can include failure to conceive within one year of unprotected intercourse.

The treatment methods of the invention may be particularly beneficial for female mammals suffering from an ovulatory disorder. Additionally, compounds of the invention can be administered to females undergoing assisted reproductive treatments such as in-vitro fertilization, e.g. to stimulate follicular development and maturation, as well as implantation procedures. In particular, treatment methods of the invention may be used in conjunction with in vitro fertilization technology to enhance survival and/or fertilization of a mammalian egg such as in IVF setting.

Treatment methods of the invention also may be employed for control of cervical ripening in late pregnancy (e.g. in humans, late pregnancy would be third trimester, particularly week 30 onward).

Therapeutic methods of the invention also include treatment of glaucoma or other disorder involving elevated intraocular pressure.

Treatment methods of the invention also include inhibition or prevention of bone loss such as to treat osteoporosis, and for promoting bone formation (e.g. to use as a therapy in a bone fracture) and other bone diseases such as Paget's disease. The invention also includes methods for treating a mammal that has low bone mass, or is susceptible to low bone mass such as a mammal having a condition that can present low bone mass, e.g. osteoporosis.

The invention also includes therapeutic methods for other bone mass augmentation treatments or enhancement, such as enhancing bone graft success rates or replacement of the need of such grafts, bone extension, bone healing following facial reconstruction and other treatments. Such treatment also may be used in coordination with an appropriate medical device, such as an orthopedic device e.g. a spinal case, bone pins and screws, and other bone fixation devices.

In general, such therapies are useful for any condition which can present low bone mass, which conditions include those where the level of bone mass is below the age specific normal as defined in standards by the World Health Organization "Assessment of Fracture Risk and its Application to Screening for Postmenopausal Osteoporosis (1994), World Health Organization Technical Series 843." More particularly, such conditions include periodontal disease, alveolar bone loss, post-osteotomy and childhood idiopathic bone loss, and primary and second osteoporosis as discussed above and complications thereof such as curvature of the spine, loss of height and prosthetic surgery.

Subject particularly suitable for such bone growth promotion therapies include subjects suffering from acute injuries that can involve bone damage, subjects having undergone related surgery such as facial reconstruction, and subjects that are at increased risk of the above discussed disorders and diseases such as post-menopausal women and men and women over the age of 50 or 60.

Compounds of the invention also will be useful to treat sexual dysfunction, including male sexual dysfunction, such as erectile dysfunction.

Compounds of the invention also are useful for treatment of a subject suffering from or susceptible to renal dysfunction, including a mammal suffering from or susceptible to acute or chronic renal failure. Such treatment methods can promote repair and/or regeneration of kidney tissue in a mammal, particularly a human.

Compounds of the invention also are useful for treatment of a subject suffering from or susceptible to an immune disorder including an immune deficiency disease or disorder, including such a disorder associated with a viral infection particularly a retroviral infection such as an HIV infection. Particularly benefited by such therapies will be a human suffering from or susceptible to AIDS.

Compounds of the invention will be further useful to reduce elevated intra-ocular pressure of a subject, e.g. through relaxation of pre-contracted isolated ciliary muscle. In particular, a mammal such as a human suffering from or susceptible to glaucoma or other disorder associated with elevated intra-ocular pressure. Compounds of the invention also will be useful for treatment of a mammal, particularly a human that is suffering from or susceptible to dry eye.

Compounds of the invention will be further useful for treatment of a subject suffering from or susceptible to inflammatory diseases or disorders, including vascular inflammation, inflammatory pain and hyperalgesia.

Compounds of the invention also will be useful for promoting sleep in a subject, e.g. to treat a mammal particularly a human suffering from or susceptible to a sleep disorder such as may be associated with advanced age, such as a human of 65 years or older.

The therapeutic methods of the invention generally comprise administration of an effective amount of one or more compounds of the invention to a subject including a mammal, such as a primate, especially a human, in need of such treatment.

Typical candidates for treatment in accordance with the methods of the invention persons suffering from or suspected of suffering from any of the above disorders or diseases, such as a female susceptible or suffering from preterm labor, or a subject suffering from or susceptible to dysmenorrhea or undesired bone loss.

The treatment methods of the invention also will be useful for treatment of mammals other than humans, including for veterinary applications such as to treat horses and livestock e.g. cattle, sheep, cows, goats, swine and the like, and pets such as dogs and cats. Methods of the invention to treat premature labor will be particularly useful for such veterinary applications. Therapeutic methods of the invention also will be useful for treatment of infertility in such veterinary applications.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention, including 1,2-substituted 5-pyrrolidinone compounds and EP4 agonists, may be administered as a "cocktail" formulation with other therapeutics, i.e. coordinated administration for simultaneous, sequential or separate use, of one or more compounds of the invention together with one or more other active therapeutics, particularly one or more other known fertility agents. For instance, one or more compounds of the invention may be administered in coordination for simultaneous, sequential or separate use, with a regime of a pain relief agent, an anti-inflammatory agent, or an anti-coagulant, depending on the indication being treated. Suitable anti-coagulants for such coordinated drug therapies include e.g. warfarin, heparin, hirudin or hirulog or an antiplatelet such as ReoPro.

For treatment of fertility disorders, one or more compounds of the invention, may be suitably administered in coordination, for simultaneous, sequential or separate use, with known fertility agents such as Follicle Stimulating and/or Leutinizing Hormone such as Gonal-F, Metrodin HP or Pergonal.

Compounds of the invention, including 1,2-substituted 5-pyrrolidinone compounds and EP4 agonists, may be administered either as the sole active therapeutic or in a coordinated regime with one or more other therapeutics can be administered by a variety of routes, such as orally or by injection, e.g., intramuscular, intraperitoneal, subcutaneous or intravenous injection, or topically such as transdermally, vaginally and the like. Pyrrolidine compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base addition salts may be prepared. Lists of additional suitable salts may be found, e.g. in Part 5 of *Remington's Pharmaceutical Sciences*, 20$^{th}$ Edition, 2000, Marck Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention may preferably include a compound of the invention, including a 1,2-substituted 5-pyrrolidinone compounds and EP4 agonists, packaged together with instructions (written) for therapeutic use of the compound to treat e.g. premature labor, dysmenorrhea or asthma, or other disorder as disclosed herein, such as a disease or disorder associated with or mediated by prostaglandin.

For oral administration, pharmaceutical compositions containing one or more compounds of the invention, including substituted pyrrolidine compounds and EP4 agonists, may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampules are convenient unit dosages.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more 1,2-substituted 5-pyrrolidinone compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention. In the examples below, "rac." refers to a racemate or racemic mixture of the specified compound.

EXAMPLES 1-80

Synthesis of Compounds of the Invention

The compounds of Examples 1 to 80 are preferred embodiments of the invention. Compounds from example 1 to 80 were synthesized according to scheme 1

EXAMPLES 1 AND 2

Synthesis of 4-(2-{(2R)-2-[(1E)-3-hydroxyoct-1-enyl]-5-oxo-pyrrolidin-1-yl}ethyl)benzoic acid

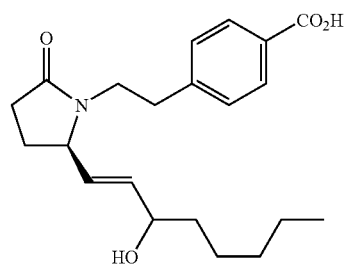

Intermediate 1.1: tert-butyl 1-{2-[4-(methoxycarbonyl)phenyl]ethyl}-5-oxo-D-prolinate To a solution of H-D-Glu(O$^t$Bu)-O$^t$Bu (0.5 g, 2.23 mmol) in MeOH (15 mL) were added 4-carbomethoxyphenylacetaldehyde (obtained from methyl 4-formyl benzoate as described in *J. Med. Chem.* 1989, 32, 1277-1283) (0.4 g, 2.23 mmol), acetic acid (0.15 mL, 2.67 mmol), and NaCNBH$_3$ (3.3 mL, 1.0 M THF solution, 3.3 mmol). The resulting solution was stirred at RT for 3 h then was diluted with EtOAc (100 mL) and washed with water (50 mL), and brine (50 mL). The organic solution was dried over sodium sulfate and concentrated in vacuo. The crude oil was diluted with xylene and the solution refluxed for 5 h. This solution was concentrated under reduced pressure and purified by silica gel column chromatography using EtOAc/hexane as eluent to afford the title compound (0.75 g, 75%) as a white solid. R$_f$ 0.45 (EtOAc/hexane 1/1); $^1$H NMR (CDCl$_3$) δ 1.47 (s, 9H), 1.95-2.05 (m, 1H), 2.10-2.20 (m, 1H), 2.25-2.35 (m, 1H), 2.40-2.50 (m, 1H), 2.80-3.00 (m, 2H), 3.10-3.20 (m, 1H), 3.82 (dd, 1H), 3.91 (s, 3H), 3.90-4.01 (m, 1H), 7.25 (d, 2H), 7.96 (d, 2H).

Intermediate 1.2: 1-{2-[4-(methoxycarbonyl)phenyl]ethyl}-5-oxo-D-proline

Intermediate 1.1 (1.6 g, 4.61 mmol) was dissolved in TFA (20 mL) and water (0.1 mL). This solution was stirred at RT for 3 h then concentrated in vacuo to afford the title compound (1.3 g, 98%) as a pale yellow solid used in the next step without further purification. $^1$H NMR (CDCl$_3$) δ 2.10-2.20 (m, 1H), 2.23-2.35 (m, 1), 2.45-2.65 (m, 2H), 2.85-3.02 (m, 2H), 3.20-3.30 (m, 1H), 3.91 (s, 3H), 3.95-4.05 (m, 2H), 7.25 (d, 2H), 7.97 (d, 2H).

Intermediate 1.3: methyl 4-{2-[(2R)-2-(hydroxymethyl)-5-oxopyrrolidin-1-yl]ethyl}benzoate Intermediate 1.2 (4.14 g, 14.2 mmol) was dissolved in THF (50 mL) and cooled to –10° C. The solution was treated with N-methylmorpholine (1.65 mL, 15.1 mmol) and stirred for 5 min. To the solution was added dropwise isobutyl chloroformate (2.00 mL, 15.1 mmol). After the addition was completed, the solution was stirred for 30 min and then filtered through a pad of celite. The collected solution was cooled to –10° C. To the solution was added sodium borohydride (0.81 g, 21.0 mmol) predissolved in water (30 mL). The solution was stirred at 0° C. for 1 h and then at RT for 1 h. The solution was poured into a separatory funnel and diluted with EtOAc (200 mL). The organic layer was washed with 1N HCl solution, saturated NaHCO₃ solution, and brine. The organic layer was dried over sodium sulfate, filtered, and concentrated. The residue was purified by column chromatography (EtOAc/hexane) and the alcohol (2.0 g, 50%) was isolated as a white solid. ¹H NMR (CDCl₃) δ 1.80-1.90 (m, 2H), 1.95-2.06 (m, 1H), 2.23-2.35 (m, 1H), 2.40-2.51 (m, 1H), 2.83-3.02 (m, 2H), 3.21-3.35 (m, 1H), 3.45-3.53 (m, 1H), 3.56 (dd, 1H), 3.71 (dd, 1H), 3.82-3.95 (m, 1H), 3.89 (s, 3H), 7.27 (dd, 2H), 7.95 (dd, 2H).

Intermediate 1.4: methyl 4-{2-[(2R)-2-formyl-5-oxopyrrolidin-1-yl]ethyl} benzoate A DCM solution of oxalyl chloride (2.34 mL, 2.0 M, 4.69 mmol) was diluted with dry DCM (40 mL) and cooled to −70° C. then a solution of DMSO (0.41 mL, 5.78 mmol) in DCM (5 mL) was added dropwise. After 15 min. to this solution was added dropwise a solution of intermediate 1.3 (1.04 g, 3.61 mmol) in DCM (10 mL). The resulting solution was stirred at −78° C. for 45 min. then Et₃N (2.5 mL, 18 mmol) was added and the solution warmed to RT. After 15 min. the solution was diluted with DCM (100 mL) and washed with a saturated solution of NH4Cl (2×100 mL), brine (100 mL), dried over sodium sulfate and concentrated in vacuo to afford the aldehyde intermediate (0.99 g, 97%) used in the next step without further purification.

Intermediate 1.5: methyl 4-(2-{(5R)-2-oxo-5-[(1E)-3-oxooct-1-enyl]pyrrolidin-1-yl}ethyl)benzoate A suspension of dimethyl (2-oxoheptyl)-phosphonate (1.5 mL, 7.21 mmol) in THF (40 mL) was cooled to 0° C. then NaH (0.29 g, 60%, 7.21 mmol) was added portionwise. After 30 min, a THF (10 mL) solution of intermediate 1.4 previously obtained was added dropwise to the reaction mixture. The resulting mixture was stirred at RT for 3 h then was diluted EtOAc (100 mL) and washed with HCl 1M solution (100 mL) and brine. The organic phase was dried over sodium sulfate, filtered, and concentrated in vacuo. The residue was purified by column chromatography (EtOAc/hexane) and the product (1.3 g, 90%) was isolated as a colorless oil. R_f 0.3 (EtOAc/hexane 2/1); MS (m/z) 372.5 (M+1).

Intermediate 1.6: methyl 4-(2-{(2R)-2-[(1E)-3-hydroxyoct-1-enyl]-5-oxopyrro-lidin-1-yl}ethyl)benzoate To a mixture of intermediate 1.5 (1.3 g, 3.5 mmol) in EtOH (20 mL) and water (20 mL) were added CeCl₃ (1.13 g, 9.15 mmol) followed by NaBH₄ (0.35 g, 9.15 mmol). After 1 h the reaction was diluted with a saturated solution of NaHCO₃ (70 mL) and extracted with EtAOc (3×70 mL). The combined organic phase was washed with brine (100 mL), dried over sodium sulfate, filtered, and concentrated in vacuo. The residue was purified by column chromatography (EtOAc/hexane) and the product (1.3 g, mixture of two diastereoisomers, 90%) was isolated as colorless oil. R_f 0.3 (EtOAc); MS (m/z) 374.5 (M+1).

EXAMPLES 1 AND 2

4-(2-{(2R)-2-[(1E)-3-hydroxyoct-1-enyl]-5-oxopyr-rolidin-1-yl}ethyl) benzoic acid To a solution of intermediate 1.6 (1.3 g, 4.58 mmol) in water (2 mL), MeOH (6 mL), and THF (6 mL) was added NaOH (0.26 g, 6.4 mmol). The resulting solution was stirred at RT for 5 h then was concentrated under reduced pressure. The crude mixture of diastereisomers was purified by RP-HPLC using ACN/H₂O (10 mmol NaOAc) to afford the desired compounds.

EXAMPLE 1

4-(2-{(2R)-2-[(1E,3S)-3-hydroxyoct-1-enyl]-5-oxopyrrolidin-1-yl}ethyl) benzoic acid (first isomer in HPLC: ACN/H₂O 0.1% TFA): ¹H NMR (CD₃OD) δ 0.85-0.95 (m, 3H), 1.20-1.50 (m, 8H), 1.65-1.81 (m, 1H), 2.11-2.41 (m, 3H), 2.79-2.95 (m, 2H), 3.11-3.22 (m, 1H), 3.65-3.80 (m, 1H), 3.98-4.10 (m, 2H), 5.43 (dd, 1H), 5.65 (dd, 1H), 7.31 (d, 2H), 7.94 (d, 2H); MS (m/z) 360 (M+1).

EXAMPLE 2

4-(2-{(2R)-2-[(1E,3R)-3-hydroxyoct-1-enyl]-5-oxopyrrolidin-1-yl}ethyl) benzoic acid (second isomer in HPLC: ACN/H₂O 0.1% TFA): ¹H NMR (CD₃OD) δ 0.85-0.95 (m, 3H), 1.20-1.55 (m, 8H), 1.65-1.78 (m, 1H), 2.11-2.45 (m, 4H), 2.80-2.95 (m, 2H), 3.16-3.28 (m, 1H), 3.65-3.80 (m, 1H), 3.98-4.10 (m, 2H), 5.43 (dd, 1H), 5.70 (dd, 1H), 7.33 (d, 2H), 7.94 (d, 2H); MS (m/z) 360 (M+1).

EXAMPLES 3 AND 4

Synthesis of 4-(2-{(2S)-2-[(1E)-3-hydroxyoct-1-enyl]-5-oxo-pyrrolidin-1-yl}ethyl)benzoic acid

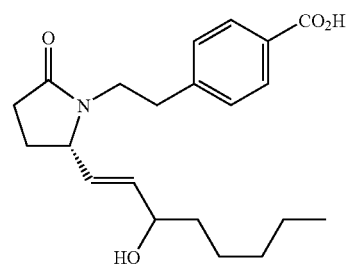

The title compounds were prepared from H-Glu(O^tBu)-O^tBu and dimethyl (2-oxoheptyl)-phosphonate using the procedure of Example 1 and 2.

EXAMPLE 3

4-(2-{(2S)-2-[(1E,3S)-3-hydroxyoct-1-enyl]-5-oxopyrrolidin-1-yl}ethyl) benzoic acid: ¹H NMR (DMSO-d₆) δ 0.85-0.95 (m, 3H), 1.20-1.50 (m, 8H), 1.55-1.67 (m, 1H), 2.05-2.30 (m, 3H), 2.65-2.89 (m, 2H), 2.95-3.05 (m, 1H), 3.55-3.65 (m, 1H), 3.88-4.03 (m, 2H), 4.65-4.80 (m, 1H), 5.35 (dd, 1H), 5.63 (dd, 1H), 7.29 (d, 2H), 7.85 (d, 2H); MS (m/z) 360 (M+1).

EXAMPLE 4

4-(2-{(2S)-2-[(1E,3R)-3-hydroxyoct-1-enyl]-5-oxopyrrolidin-1-yl}ethyl) benzoic acid: ¹H NMR (CD₃OD) δ 0.85-0.95 (m, 3H), 1.20-1.60 (m, 8H), 1.65-1.80 (m, 1H), 2.10-2.40 (m, 3H), 2.80-3.00 (m, 2H), 3.12-3.25 (m, 1H), 3.65-3.80 (m, 1H), 3.95-4.10 (m, 2H), 5.43 (dd, 1H), 5.70 (dd, 1H), 7.33 (d, 2H), 7.94 (d, 2H); MS (m/z) 360 (M+1).

EXAMPLES 5 AND 6

Synthesis of: 4-(2-{(2R)-2-[(1E)-3-hydroxy-4,4-dimethyloct-1-enyl]-5-oxopyrrolidin-1-yl}ethyl) benzoic acid

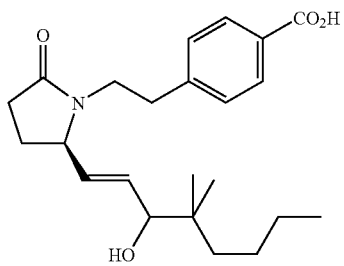

Intermediate 5.1: 2,2-dimethyl-hexanoic acid methyl ester

To a solution of 2,2-Dimethyl-hexanoic acid (10.15 g, 0.07 mol) in ether (150 mL) was added (trimethylsilyl)diazomethane (46 ml, 2M in hexanes, 0.092 mol) drop wise. The mixture was stirred for 3 h, and ether was evaporated without applying reduced pressure. Fractional distillation of the residue provided the title ester 11.12 g (b.p. 90-95° C./1 mmHg). $^1$H NMR (CDCl$_3$): δ 0.85 (t, J=7.0 Hz, 3H), 1.1-1.2 (m, 2H), 1.13 (s, 6H), 1.21-1.31 (m, 2H), 1.44-1.51 (m, 2H), 3.72 (s, 3H).

Intermediate 5.2: dimethyl (3,3-dimethyl-2-oxoheptyl)-phosphonate

To a solution of dimethyl methanephosphonate (19.0 g, 0.15 mol) in dry THF (150 mL) at −70° C. under N$_2$ was added n-BuLi (67.0 ml, 2.5M in hexanes, 0.16 mol). The mixture was stirred at −70° C. for 20 min. Then intermediate 5.1 (11.12 g, 0.07 mol) in THF (25 mL) was added dropwise. The mixture was stirred at −70° C. for an additional 45 min, and then the mixture was allowed to come to room temperature completely. Quenched with 5% HCl (75 mL), diluted with DCM (500 mL) and washed with brine (100 ml). Concentrated and purified on a silica gel column by eluting with 60% EtOAc-hexane mixture to obtain 1.05 g of phosphonate along with the recovery of 5.42 g of the starting ester. $^1$H NMR (CDCl$_3$): δ 0.83 (t, J=7.4 Hz, 3H), 1.1-1.2 (m, 2H), 1.09 (s, 6H), 1.21-1.31 (m, 2H), 1.44-1.51 (m, 2H), 3.43 (d, J=21.2 Hz, 2H), 3.75 (d, J=11.0 Hz, 3H).

Intermediate 5.3: methyl 4-{2-[(2S)-2-formyl-5-oxopyrrolidin-1-yl]ethyl}benzoate A DCM solution of oxalyl chloride (0.7 mL, 2.0 M, 1.4 mmol) was diluted with dry DCM (10 mL) and cooled to −70° C. then a solution of DMSO (0.15 mL, 1.6 mmol) in DCM (3 mL) was added dropwise. After 15 min. to this solution was added dropwise a solution of intermediate 1.3 (278 mg, 1.0 mmol) in DCM (3 mL). The resulting solution was stirred at −78° C. for 45 min. then Et$_3$N (0.7 mL, 5.0 mmol) was added and the solution warmed to RT. After 15 min. the solution was diluted with DCM (100 mL) and washed with a saturated solution of NH$_4$Cl (20 mL), brine (25 mL), dried over sodium sulfate and concentrated in vacuo to afford the aldehyde intermediate (265 mg) used in the next step without further purification.

Intermediate 5.4: methyl 4-(2-{2-[(1E)-4,4-dimethyl-3-oxooct-1-enyl]-5-oxo-pyrrolidin-1-yl}ethyl)benzoate To a suspension of NaH (55 mg, 60% in mineral oil, 1.2 mmol) in dry THF (3 mL) at 0° C. under N$_2$ atmosphere was added intermediate 5.2 (270 mg, 1.1 mmol) in THF (2 mL) dropwise. After 30 min, intermediate 5.3 in THF (3 mL) was added to the pale yellow colored ylide suspension. The resulting mixture was stirred at RT for 1 h, and then was quenched with 5% HCl (1 mL). Diluted with EtOAc (100 mL), washed with water (10 mL) and brine (10 mL). The organic phase was dried over sodium sulfate, filtered, and concentrated in vacuo. The residue was purified by column chromatography (50% EtOAc/hexane) and the product (200 mg, 50%) was isolated as a colorless oil. R$_f$0.4 (EtOAc/hexane 3/1); $^1$H NMR (CDCl$_3$): δ 0.80 (t, J=7.8 Hz, 3H), 0.9-1.14 (m, 2H), 1.06 (s, 6H), 1.16-1.26 (m, 2H), 1.42-1.50 (m, 2H), 1.66-1.76 (m, 1H), 2.06-2.16 (m, 1H), 2.24-2.42 (m, 2H), 2.70-3.08 (m, 3H), 3.76-3.86 (m, 2H), 3.85 (s, 3H), 6.39 (d, J=15.4 Hz, 1H), 6.56 (dd, J$_1$32 15.6 Hz, J$_2$=7.3 Hz, 1H), 7.19 (d, J=8.1 Hz, 2H), 7.91 (d, J=8.4 Hz, 2H), 3.43 (d, J=21.2 Hz, 2H), 3.75 (d, J=11.0 Hz, 3H); $^{13}$C NMR (CDCl$_3$): 14.7, 23.9, 24.5 (2C), 25.7 27.5, 30.2, 34.5, 39.8, 42.7, 47.0, 52.5, 60.2, 125.5, 128.4, 128.5 (2C), 129.6 (2C), 143.4, 143.8, 166.3, 174.3, 202.5

Intermediate 5.5: methyl 4-(2-{2-[(1E)-3-hydroxy-4,4-dimethyloct-1-enyl]-5-oxopyrrolidin-1-yl}ethyl) benzoate To a mixture of intermediate 5.4 (200 mg, 0.5 mmol) in EtOH (10 mL) and water (6 mL) were added CeCl$_3$ (486 mg, 1.3 mmol) followed by NaBH$_4$ (50 mg, 1.3 mmol). After 1 h the reaction was diluted with a saturated solution of NaHCO$_3$ (10 mL) and extracted with EtOAc (3×50 mL). The combined organic phase was washed with brine (15 mL), dried over sodium sulfate, filtered, and concentrated in vacuo to obtain 200 mg of the alcohol as a diastereomeric mixture. The crude mixture was used as such for the next step with out further purification.

EXAMPLES 5 AND 6

4-(2-{(2R)-2-[(1E)-3-hydroxy-4,4-dimethyloct-1-enyl]-5-oxopyrro-lidin-1-yl}ethyl)benzoic acid To a solution of intermediate 5.5 (200 mg, 0.5 mmol) in MeOH (6 mL) and water (0.4 mL) was added NaOH (40 mg, 1 mmol). The resulting solution was heated under microwave oven for 15 min at 80° C. in a sealed tube. Then the reaction mixture was concentrated under reduced pressure. The crude mixture of diastereomers was purified by RP-HPLC using ACN/H$_2$O (10 mmol NaOAc) to afford the desired compounds.

EXAMPLE 5

4-(2-{2-[(1E,3S)-3-hydroxy-4,4-dimethyloct-1-enyl]-5-oxopyrrolidin-1-yl}ethyl)benzoic acid: (First isomer in HPLC: ACN/H$_2$O/TFA, 30 mg): $^1$H NMR (CDCl$_3$): δ 0.76-0.98 (t, 3H, 2s, 6H), 1.1-1.14 (m, 6H), 1.66-1.80 (m, 1H), 2.1-2.44 (m, 3H), 2.74-3.0 (m, 2H), 3.06-3.2 (m, 1H), 3.68-3.86 (m, 2H), 3.94-4.08 (m, 1H), 5.45 (dd, J$_1$=15.4 Hz, J$_2$=8.8 Hz, 1H), 5.71 (dd, J$_1$=15.0 Hz, J$_2$=7.3 Hz, 1H), 7.31 (d, J=7.4 Hz, 2H), 7.94 (d, J=7.7 Hz, 2H); $^{13}$C NMR (CDCl$_3$): 13.8, 22.6, 22.8, 24.0, 25.9, 26.3, 30.2, 33.5, 37.4, 39.1, 42.1, 61.6, 78.3, 128.4 (2C), 128.7, 129.4 (2C), 130.6, 134.5, 144.2, 167.7, 175.6; MS calcd. for $C_{23}H_{33}NO_4$: 387; Found (m/z): 388 (M+1).

EXAMPLE 6

4-(2-{2-[(1E,3R)-3-hydroxy-4,4-dimethyloct-1-enyl]-5-oxopyrrolidin-1-yl}ethyl)benzoic acid: (second isomer in HPLC: ACN/H$_2$O 0.1% TFA, 47 mg): $^1$H NMR (CDCl$_3$): δ 0.76-0.98 (t, 3H, 2s, 6H), 1.14-1.37 (m, 6H), 1.60-1.78 (m, 1H), 2.08-2.44 (m, 3H), 2.76-2.98 (m, 2H), 3.14-3.28 (m, 1H), 3.66-3.84 (m, 2H), 3.94-4.08 (m, 1H), 5.40 (dd, $J_1$=15.2 Hz, $J_2$=8.8 Hz, 1H), 5.71 (dd, $J_1$=15.4 Hz, $J_2$=6.6 Hz, 1H), 7.32 (d, J=7.7 Hz, 2H), 7.94 (d, J=7.7 Hz, 2H); $^{13}$C NMR (CDCl$_3$): δ 13.9, 22.8, 24.0, 26.1, 26.3, 30.3, 33.6, 37.5, 38.9, 42.1, 61.6, 78.0, 128.5 (2C), 129.4 (2C), 130.1, 134.5, 144.2, 167.8, 175.6; MS calcd. for $C_{23}H_{33}NO_4$: 387; Found (m/z): 388 (M+1).

EXAMPLES 7 AND 8

Synthesis of 4-(2-{(2R)-2-[(1E,3R)-3-hydroxy-3-(1-phenylcyclopropyl)prop-1-enyl]-5 oxopyrrolidin-1-yl}ethyl)benzoic acid and 4-(2-{(2R)-2-[(1E,3S)-3-hydroxy-3-(1-phenylcyclopropyl)prop-1-enyl]-5-oxopyrrolidin-1-yl})ethyl)benzoic acid

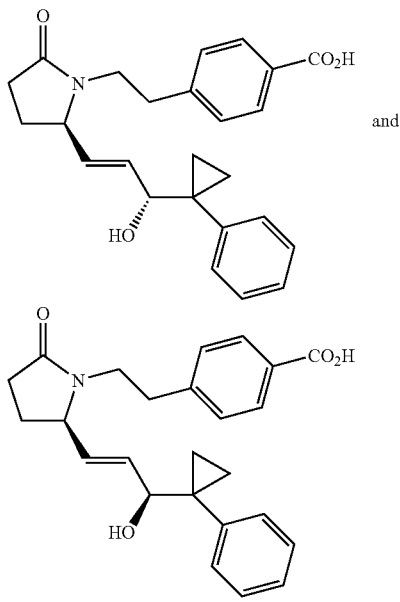

and

The title compound were made in an analogous manner to that described for Example 5 and 6 starting from intermediate 1.4, 1-phenyl cyclopropanecarboxylic acid, and dimethyl methanephosphonate.

EXAMPLE 7

4-(2-{(2R)-2-[(1E,3R)-3-hydroxy-3-(1-phenylcyclopropyl)prop-1-enyl]-5 oxo pyrrolidin-1-yl}ethyl)benzoic acid (First isomer in HPLC: ACN/H$_2$O 0.1% TFA) $^1$H NMR (D$_2$O) δ 0.75-0.93 (m, 4H), 1.45-1.63 (m, 1H), 2.00-2.12 (m, 1H), 2.20-2.35 (m, 2H), 2.78-2.90 (m, 2H), 3.05-3.12 (m, 1H), 3.60-3.78 (m, 2H), 3.81-3.90 (m, 1H), 5.25 (dd, 1H), 5.50 (dd, 1H), 7.20-7.40 (m, 7H), 7.76 (d, 2H); MS (m/z) 406 (M+1).

EXAMPLE 8

4-(2-{(2R)-2-[(1E,3S)-3-hydroxy-3-(1-phenylcyclopropyl)prop-1-enyl]-5-oxo pyrrolidin-1-yl}ethyl)benzoic acid (Second isomer in HPLC: ACN/H$_2$O 0.1% TFA). $^1$H NMR (CD$_3$OD) δ 0.70-0.98 (m, 4H), 1.50-1.63 (m, 1H), 2.05-2.30 (m, 4H), 2.70-2.85 (m, 2H), 2.86-2.98 (m, 1H), 3.50-3.60 (m, 1H), 3.78 (d, 1H), 3.85-3.93 (m, 1H), 5.25 (dd, 1H), 5.64 (dd, 1H), 7.10-7.40 (m, 7H), 7.93 (d, 2H); MS (m/z) 406 (M+1).

EXAMPLE 9

4-(2-{(2R)-2-[(1E,3S)-3-hydroxy-4-(3-chlorophenyl)but-1-enyl]-5-oxopyrrolidin-1-yl}ethyl)benzoic acid

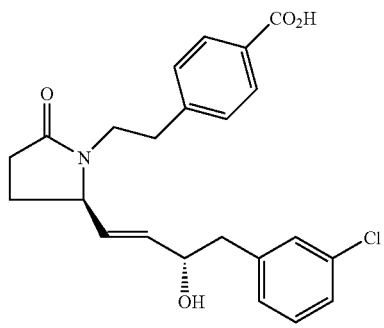

Intermediate 9.1. Dimethyl 3-(3-chlorophenyl)-2-oxopropylphosphonate

To a solution of dimethyl methylphosphonate (4.32 mL, 40 mmol) in anhydrous THF (40 mL), cooled at −78° C. was added n-BuLi (1.6 M in hexane, 27.5 mL, 44 mmol). The mixture was stirred for 30 minutes at this temperature under nitrogen. Methyl 3-chlorophenylacetate (3.69 mL, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (MeOH/CH$_2$Cl$_2$ 1.5/98.5) to give the product (1.43 g) with colorless oil in 26% yield. $^1$H-NMR (CDCl$_3$) δ 3.07 (d, J=21 Hz, 2H), 3.750 (s, 3H), 3.775 (s, 3H), 3.873 (s, 2H), 7.01 (t, J=8.0 Hz, 1H), 7.19 (s, 1H), 7.28 (d, J=8.0 Hz, 2H).

Intermediate 9.2. Methyl 4-(2-{(5R)-2-oxo-5-[(1E)-3-oxo-4-(3-chlorophenyl)-but-1-enyl]pyrrolidin-1-yl}ethyl)benzoate To a solution of Intermediate 9.1 (402.5 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (3 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$, The residue was purified through flash chromatography on silica gel (EtOAc/Hexanes 1/1) to give the product (350 mg) as a colorless oil in 56% yield. $^1$H-NMR (CDCl$_3$) δ 1.57 (m, 2H), 0.829 (m, 2H), 0.937

(m, 2H), 1.091-1.130 (m, 3H), 3.771 (s, 3H), 3.908 (s, 2H), 6.095 (d, J=15.8 Hz, 1H), 6.511 (dd, J=8.1 and 15.8 Hz, 1H), 7.09 (m, 1H), 7.24 (d, J=8.4 Hz, 2H), 7.25 (s, 1H), 7.28 (d, J=8.0 Hz, 2H), 7.95 (d, J=8.4 Hz, 2H).

Intermediate 9.3. Methyl 4-(2-{(2R)-2-[(1E,3S)-3-hydroxy-4-(3-chlorophenyl) but-1-enyl]-5-oxopyrrolidin-1-yl}ethyl)benzoate To a solution of (R)-2-methyl-CBS-oxazaborolidine (1.0 M in toluene, 0.80 mL, 0.80 mmol) in anhydrous THF at 0° C. was added Borane-THF complex (1.0 M, 0.80 mL, 0.80 mmol) dropwise. The mixture was stirred for 15 minutes. Intermediate 9.2 (400 mg, 0.80 mmol) in THF (2 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was purified through flash chromatography on silica gel (EtOAc) to give the product (220 mg) as colorless oil in 64% yield. $^1$H-NMR (CDCl$_3$) δ 2.21 (m, 1H), 2.40 (m, 2H), 2.818 (m, 5H), 3.710 (m, 3H), 3.90 (s, 3H), 4.353 (d, J=7.0 Hz, 1H), 5.340 (dd, J=8.5 and 16.1 Hz, 1H), 5.567 (dd, J=6.2 and 16.1 Hz, 1H), 7.221 (m, 6H), 7.949 (d, J=8.1 Hz, 2H).

EXAMPLE 9

4-(2-{(2R)-2-[(1E,3S)-3-hydroxy-4-(3-chlorophenyl) but-1-enyl]-5-oxopyrrolidin-1-yl}ethyl)benzoic acid To a solution of Intermediate 9.3 (220 mg, 0.514 mmol) in MeOH/THF/H$_2$O (2/2/2 mL) was added NaOH (1.0 M, 1.29 mL, 1.29 mmol). The mixture was stirred for overnight. After concentration under reduced pressure, the residue was purified, through RP-HPLC using ACN and H$_2$O 0.1% TFA to afford the desired product (140 mg, 65%) as a white solid. $^1$HNMR (CD$_3$OD, ppm) δ 1.610 (m, 1H), 2.239 (m, 3H), 3.542 (m, 1H), 3.881 (dd, J=6.4 and 8.0 Hz 1H), 4.305 (dd, J=7.4 and 6.6 Hz, 1H), 5.255 (dd, J=7.7 and 15 Hz, 1H), 5.579 (dd, J=6.6 and 15 Hz, 1H), 7.25 (m, 4H), 7.27 (d, J=8.4 Hz, 2H), 7.943 (d, J=8.4 Hz, 2H). MS (m/z) 414.9 (M+H$^+$), 436.3 (M+Na$^+$).

EXAMPLE 10

4-(2-{(2R)-2-[(1E,3S)-3-hydroxynon-1-enyl]-5-oxopyrrolidin-1-yl}ethyl) benzoic acid

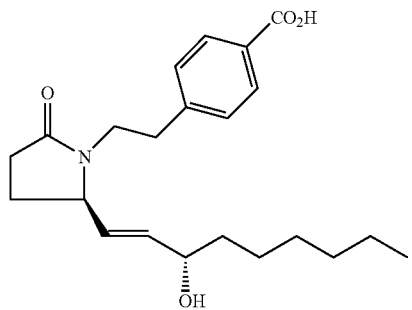

Intermediate 10.1. Ethyl 2-oxooctylphosphonate

To a solution of dimethyl methylphosphonate (3.25 mL, 30 mmol) in anhydrous THF (30 mL), cooled at −78° C. was added n-BuLi (1.6 M in hexane, 20.6 mL, 33 mmol). The mixture was stirred for 30 minutes at this temperature under nitrogen. Methyl enanthate (2.49 mL, 13 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (MeOH: CH$_2$Cl$_2$=2:98) to give the product (3.32 g) with colorless oil in 91% yield. $^1$H NMR (CDCl$_3$) δ 0.801 (m, 3H), 1.214 (m, 6H), 1.56 (m, 2H), 2.548 (m, 2H), 3.048 (d, J=21.8 Hz, 2H), 3.710 (s, 3H), 3.738 (s, 3H).

Intermediate 10.2. Methyl 4-(2-{(5R)-2-oxo-5-[(1E)-3-oxonon-1-enyl]pyrrolidin-1-yl}ethyl) benzoate To a solution of Intermediate 10.1 (343.74 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc: Hexanes=1:1) to give the product (420 mg) as a colorless oil in 75% yield. $^1$H NMR (CDCl$_3$) δ 0.887 (m, 3H), 1.279 (m, 4H), 1.584 (m, 8H), 2.519 (m, 4H), 2.921 (m, 2H), 3.046 (m, 1H), 3.901 (s, 3H), 6.067 (d, J=15.8 Hz, 1H), 6.430 (dd, J=8.0 and 15.8 Hz, 1H), 7.250 (d, J=8.0 Hz, 2H), 7.972 (d, J=8 Hz, 2H), MS (m/z) 408.4 (M+Na$^+$).

Intermediate 10.3. Methyl 4-(2-{(2R)-2-[(1E,3S)-3-hydroxynon-1-enyl]-5-oxopyrrolidin-1-yl}-ethyl) benzoate To a solution of (R)-2-methyl-CBS-oxazaborolidine (1.0 M in toluene, 1.04 mL, 1.04 mmol) in, anhydrous THF at 0° C. was added Borane-THF complex (1.0 M, 1.04 mL, 1.04 mmol) dropwise. The mixture was stirred for 15 minutes. Intermediate 10.2 (400 mg, 1.04 mmol) in THF (3 mL) was added dropwise. The mixture was stirred for 3 hours. The mixture was quenched with addition of 1 mL of the saturated ammonia chloride and was dilute with EtOAc (50 mL). The organic layer was washed with brine (3×5 mL), dried over MgSO4. The residue was purified through flash chromatography on silica gel (EtOAc) to give the product (380 mg) as colorless oil in 95% yield. MS (m/z): 388.3 (M+H$^+$).

EXAMPLE 10

4-(2-{(2R)-2-[(1E,3S)-3-hydroxynon-1-enyl]-5-oxopyrrolidin-1-yl}ethyl) benzoic acid To a solution of Intermediate 10.3 (200 mg, 0.516 mmol) in MeOH/THF/H$_2$O (2/2/2 mL) was added NaOH (1.0 M, 1.29 mL, 1.29 mmol). The mixture was stirred for overnight. After concentration under reduced pressure, the residue was purified through RP-HPLC using ACN and H$_2$O/0.1% TFA to afford the desired product (150 mg, 78%) as a white solid. $^1$H NMR (CD$_3$OD) δ 0.874 (t, J=7 Hz, 3H), 1.285 (m, 2H), 1.503 (m, 2H), 1.746 (m, 2H), 2.326 (m, 3H), 2.901 (m, 2H), 3.176 (m, 2H), 3.30 (m, 4H), 5.484 (dd, J=6.8 and 15.4 Hz, 1H), 5.657 (dd, J=6.6 and 15.4 Hz, 1H), 7.310 (d, J=7.7 Hz, 2H), 7.96 (d, J=7.7 Hz, 2H), MS (m/z) 374.6 (M+H$^+$), 396.4 (M+Na$^+$).

EXAMPLE 11

4-(2-{(2S)-2-[3-(3S)-hydroxynonyl]-5-oxopyrrolidin-1-yl}ethyl) benzoic acid

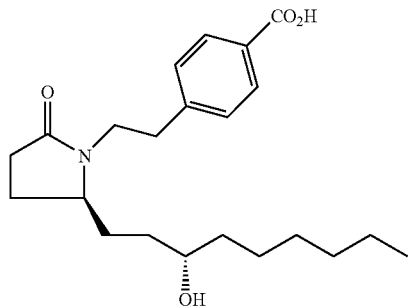

Intermediate 11.1. Methyl 4-(2-{(2S)-3-(3S)-hydroxynonyl]-5-oxopyrrolidin-1-yl}ethyl)benzoate To a solution of Intermediate 10.3 in methanol was added Pd/C. The mixture was exposure to hydrogen (with balloon) for overnight. The Pd/C was filtered through a layer of Celite. After evaporation of the solvent, the crude product was used for the next reaction without further purification.

EXAMPLE 11

4-(2-{(2R)-2-[3-(3S)-hydroxynonyl]-5-oxopyrrolidin-1-yl}ethyl) benzoic acid

To a solution of Intermediate 11.1 (0.4645 mmol) in MeOH/THF/H$_2$O (2/2/2 mL) was added NaOH (1.0 M, 1.16 mL, 1.16 mmol). The mixture was stirred for overnight. After concentration under reduced pressure, the residue was purified through RP-HPLC using ACN and H$_2$O/0.1% TFA to afford the desired product (63 mg, 36%) as a white solid. $^1$H NMR (CD$_3$OD) δ 0.899 (m, 3H), 1.307-1.789 (m, 16H), 2.106 (m, 1H), 2.275 (m, 2H), 2.945 (m, 2H), 3.54 (m, 2H), 3.820 (m, 1H), 7.352 (d, J=7.7 Hz, 2H), 7.973 (d, J=7.7 Hz, 2H), MS (m/z) 376.7 (M+H$^+$), 398.5 (M+Na$^+$).

EXAMPLES 12 AND 13

4-[2-((2R)-2-{(1E)-3-[1-(3-fluorophenyl)cyclopentyl]-3-hydroxyprop-1-enyl}-5-oxopyrrolidin-1-yl) ethyl]benzoic acid

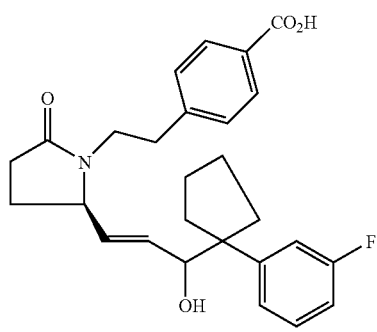

Intermediate 12.1. Methyl 1-(3-fluorophenyl)cyclopentanecarboxylate

To a solution of methyl 1-(3-fluorophenyl)cyclopentanecarboxylic acid (5.0 g, 24.01 mmol) in anhydrous methanol was added 1 mL of concentrated sulfuric acid. The mixture was refluxed overnight. The mixture was neutralized to pH 4-5 with sodium carbonate. The solvent was evaporated. The residue was dissolved in ethyl acetate (50 mL), washed with brine (3×10 mL, dried over MgSO$_4$. The crude product was used for the next reaction without further purification.

Intermediate 12.2. Dimethyl 2-[1-(3-fluorophenyl)cyclopentyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 12.1 (4.44 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (MeOH: CH$_2$Cl$_2$=2:98) to give the product (3.8 g) with colorless oil in 60% yield. $^1$H NMR (CDCl$_3$) δ 1.70 (m, 4H), 1.96 (m, 2H), 2.51 (m, 2H), 2.91 (d, J=12.8 Hz, 2H), 3.71 (d, J=21.2 Hz, 6H), 6.59 (m, 3H), 7.29 (m, 1H).

Intermediate 12.3. Methyl 4-[2-((2R)-2-{(1E)-3-[1-(3-fluorophenyl)cyclopentyl]-3-oxoprop-1-enyl}-5-oxopyrrolidin-1-yl)ethyl]benzoate To a solution of Intermediate 12.2 (457.16 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc:Hexanes=1:1) to give the product (604 mg) as a colorless oil in 90% yield. $^1$H NMR (CDCl$_3$) δ 1.60 (m, 4H), 1.93 (m, 2H), 2.27 (m, 2H), 2.41 (m, 2H), 2.78 (m, 2H), 3.67 (m, 1H), 3.92 (s, 3H), 5.98 (d, J=15.1 Hz, 1H), 6.50 (dd, J=8.4 and 15.1 Hz, 1H), 7.00 (m, 3H), 7.088 (d, J=8.0 Hz, 2H), 7.29 (m, 1H), 7.90 (d, J=8.0 Hz, 2H), MS (m/z) 486.5 (M+Na$^+$).

Intermediate 12.4. Methyl 4-[2-((2R)-2-{(1E)-3-[1-(3-fluorophenyl)cyclopentyl]-3-hydroxyprop-1-enyl}-5-oxopyrrolidin-1-yl)ethyl]benzoate To a solution of Intermediate 12.3 in ethanol/water (20 mL, v/v (1:1)) was added cerium chloride (711.65 mg, 1.91 mmol) and sodium borohydride (96.27 mg, 2.545 mmol). The mixture was stirred for overnight. After evaporation of the solvent, the crude product was used for the next reaction without purification.

EXAMPLES 12 AND 13

4-[2-((2R)-2-{(1E)-3-[1-(3-fluorophenyl)cyclopentyl]-3-hydroxy prop-1-enyl}-5-oxopyrrolidin-1-yl) ethyl]benzoic acid To a solution of Intermediate 12.4 (300 mg, 0.644 mmol) in MeOH/THF/H$_2$O (2/2/2 mL) was added NaOH (1.0 M, 1.61 mL, 1.61 mmol). The mixture was stirred for overnight. After concentration under reduced pressure, the residue was purified through RP-HPLC using ACN and H$_2$O/0.1% TFA to afford example 12 (80 mg, 27%) and example 13 (100 mg) as a white solid.

EXAMPLE 12

4-[2-((2R)-2-{(1E,3R)-3-[1-(3-fluorophenyl)cyclopentyl]-3-hydroxyprop-1-enyl}-5-oxopyrrolidin-1-yl)ethyl] benzoic acid (the first isomer in RP-HPLC: ACN/H$_2$O 0.1% TFA): $^1$H NMR(CD$_3$OD) δ 0.1.56 (m, 2H), 1.599 (m, 2H), 1.990 (m, 2H), 2.21 (m, 2H), 2.88 (m, 2H), 3.77 (m, 1H), 5.32 (m, 2H), 6.89 (m, 1H), 7,13 (m, 2H), 7.23 (m, 1H), 7.29 (d, J=8.4 Hz, 2H), 7.94 (d, J=8.4 Hz, 2H), MS (m/z): 452.2 (M+H$^+$).

EXAMPLE 13

4-[2-((2R)-2-{(1E,3S)-3-[1-(3-fluorophenyl)cyclopentyl]-3-hydroxyprop-1-enyl}-5-oxopyrrolidin-1-yl)ethyl] benzoic acid (the second isomer in RP-HPLC: ACN/H$_2$O 0.1% TFA): $^1$HNMR (CD$_3$OD, ppm) δ 0.1.56 (m, 2H), 1.599 (m, 2H), 1.990 (m, 2H), 2.21 (m, 2H), 2.88 (m, 2H), 3.77 (m, 1H), 5.32 (m, 2H), 6.89 (m, 1H), 7,13 (m, 2H), 7.23 (m, 1H), 7.29 (d, J=8.4 Hz, 2H), 7.94 (d, J=8.4 Hz, 2H), MS (m/z): 452.2 (M+H$^+$).

EXAMPLES 14 AND 15

4-[2-{(2R)-2-[(1E)-3-hydroxy-4-methyl-4-phenyl-pent-1-enyl]-5-oxopyrrolidin-1-yl}ethyl)benzoic acid

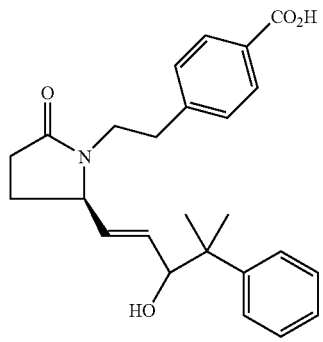

Intermediate 14.1. Dimethyl 3-methyl-2-oxo-3-phenylbutylphosphonate

To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Methyl 3-methyl-3-phenyl proponate (3.56 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc:Hexanes=1:1) to give the product (3.5 g) with colorless oil in 65% yield. $^1$H NMR (CDCl$_3$) δ 1.54 (s, 6H), 2.87 (d, J=15.8 Hz, 2H), 3.69 (d, J=11.2 Hz, 6H), 7.23 (m, 3H), 7.35 (m, 2H).

Intermediate 14.2. Methyl 4-[2-((2R)-2-{(1E)-4-methyl-3-oxo-4-phenylpent-1-enyl]-5-oxopyrrolidin-1-yl}ethyl)benzoate To a solution of Intermediate 14.1 (393.24 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with ethyl acetate (30 mL). The organic layer was washed with brine (3×5 mL), dried over MgSO$_4$, The residue was purified through flash chromatography on silica gel (EtOAc/Hexanes 1/1) to give the product (520 mg) as a colorless oil in 85% yield. $^1$H NMR (CDCl$_3$) δ 1.51 (s, 6H), 2.03 (m, 3H), 2.27 (m, 2H), 2.65 (m, 1H), 2.73 (m, 4H), 3.63 (m, 2H), 3.95 (s, 3H), 5.88 (d, J=15.3 Hz, 1H), 6.51 (dd, J=8.1 and 15.1 Hz, 1H), 7.13 (d, J=8.0 Hz, 2H), 7.23 (d, J=8.0 Hz, 2H), 7.32 (m, 3H), 7.89 (d, J=8.0 Hz, 2H), MS (m/z) 420.4 (M+H$^+$).

Intermediate 14.3. Methyl 4-[2-((2R)-2-{(1E)-3-hydroxy-4-methyl-4-phenylpent-1-enyl}-5-oxo-pyrrolidin-1-yl)ethyl]benzoate To a solution of Intermediate 14.2 (510 mg, 1.216 mmol) in ethanol/water (20 mL, v/v (1:1)) was added cerium chloride (679.6 mg, 1.824 mmol) and sodium borohydride (91.97 mg, 2.43 mmol). The mixture was stirred for overnight. After evaporation of the solvent, the crude product was used for the next reaction without purification.

EXAMPLES 14 AND 15

4-[2-{(2R)-2-[(1E)-3-hydroxy-4-methyl-4-phenyl-pent-1-enyl]-5-oxopyrrolidin-1-yl}ethyl)benzoic acid To a solution of Intermediate 14.3 (300 mg, 0.712 mmol) in MeOH/THF/H$_2$O (2/2/2 mL) was added NaOH (1.0 M, 1.78 mL, 1.78 mmol). The mixture was stirred for overnight. After concentration under reduced pressure, the residue was purified through RP-HPLC using ACN and H$_2$O/0.1% TFA to afford example 14 (70 mg) and example 15 (120 mg) as a white solid.

EXAMPLE 14

4-[2-{(2R)-2-[(1E,3R)-3-hydroxy-4-methyl-4-phenyl-pent-1-enyl]-5-oxopyrrolidin-1-yl}ethyl)benzoic acid (the first isomer in RP-HPLC: ACN/H$_2$O 0.1% TFA): $^1$H NMR (CD$_3$OD, ppm) δ 1.314 (s, 3H), 1.340 (s, 2H), 1.568 (m, 1H), 2.08 (m, 1H), 2.37 (m, 2H), 2.68 (m, 2H), 3.55 (m, 1H), 3.73 (m, 1H), 4.24 (m, 1H), 5.25 (dd, J=8.0 and 15.0 Hz, 1H), 6.39 (dd, J=6.8 and 15.0 Hz, 1H), 7.16 (d, J=8.0 Hz, 1H), 7.23 (m, 4H), 7.37 (d, J=8.0 Hz, 2H), 7.93 (d, J=8.0 Hz, 2H), MS (m/z) 408.4 (M+H$^+$).

EXAMPLE 15

4-[2-{(2R)-2-[(1E,3S)-3-hydroxy-4-methyl-4-phenyl-pent-1-enyl]-5-oxopyrrolidin-1-yl}ethyl)benzoic acid (the second isomer in RP-HPLC: ACN/H$_2$O 0.1% TFA): $^1$H NMR (CD$_3$OD) δ 1.314 (s, 3H), 1.340 (s, 2H), 1.568 (m, 1H), 2.08 (m, 1H), 2.37 (m, 2H), 2.68 (m, 2H), 3.55 (m, 1H), 3.73 (m, 1H), 4.24 (m, 1H), 5.25 (dd, J=8.0 and 15.0 Hz, 1H), 6.39 (dd, J=6.8 and 15.0 Hz, 1H), 7.16 (d, J=8.0 Hz, 1H), 7.23 (m, 4H), 7.37 (d, J=8.0 Hz, 2H), 7.93 (d, J=8.0 Hz, 2H), MS (m/z) 408.4 (M+H⁺).

EXAMPLE 16

4-[2-{(2R)-2-[(1E,3S)-3-hydroxyhept-1-enyl]-5-oxopyrrolidin-1-yl}ethyl) benzoic acid

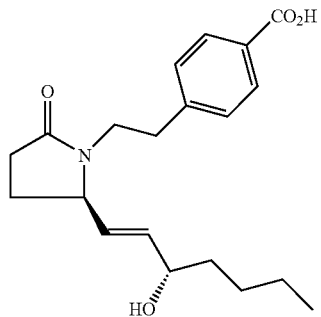

Intermediate 16.1. Dimethyl 2-oxohexylphosphonate

To a solution of dimethyl methylphosphonate (3.25 mL, 30 mmol) in anhydrous THF (30 mL), cooled at −78° C. was added n-BuLi (1.6 M in hexane, 20.6 mL, 33 mmol). The mixture was stirred for 30 minutes at this temperature under nitrogen. Methyl valerate (2.0 mL, 15 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO₄. The residue was purified through flash chromatography on silica gel (MeOH/DCM 2/98) to give the product (3.0 g) with colorless oil in 96% yield. ¹H NMR (CDCl₃) δ 0.848 (t, J=7.3 Hz, 3H), 1.28 (m, 2H), 1.52 (m, 2H), 2.57 (t, J=2.4 Hz, 2H) 3.074 (d, J=21 Hz, 2H), 3.760 (s, 3H), 3.762 (s, 3H).

Intermediate 16.2. Methyl 4-(2-{(5R)-2-oxo-5-[(1E)-3-oxohept-1-enyl]pyrrolidin-1-yl}ethyl)benzoate To a solution of Intermediate 16.1 (302.49 mg, 1.453 mmol) in anhydrous THF (10 mL) at 0° C. was added 60% NaH (58.12 mg, 1.453 mmol) in mineral oil. The mixture was stirred for 10 minutes. Intermediate 1.4 (200 mg, 0.7265 mmol) in THF (1 mL) was added dropwise. The mixture was stirred for overnight. The mixture was quenched with addition of the saturated ammonia chloride. The mixture was dilute with ethyl acetate (15 mL). The organic layer was washed with brine (3×5 mL), dried over MgSO₄, The residue was purified through flash chromatography on silica gel (EtOAc/Hexanes 1/1) to give the product (167 mg) as a colorless oil in 64% yield. ¹H NMR (CDCl₃) δ 0.908 (t, J=7.0 Hz, 3H), 1.32 (m, 2H), 1.57 (m, 2H), 1.75 9m, 2H), 2.16 (m, 2H), 2.43 (m, 2H), 2.50 (t, J=7.0 Hz, 2H), 2.60 (t, J=7.0 Hz, 2H), 2.90 (m, 1H), 3.90 (s, 3H), 6.07 (d, J=15.2 Hz, 1H), 6.44 (dd, J=8.1 and 15.3 Hz, 1H ), 7.25 (d, J=8.4 Hz, 2H), 7.91 (d, J=8.4 Hz, 2H), (m/z) 380.6 (M+Na⁺).

Intermediate 16.3. Methyl 4-(2-{(2R)-2-[(1E,3S)-3-hydroxyhept-1-enyl-5-oxopyrrolidin-1-yl}ethyl) benzoate To a solution of (R)-2-methyl-CBS-oxazaborolidine (1.0 M in toluene, 1.2 mL, 1.20 mmol) in anhydrous THF at 0° C. was added Borane-THF complex (1.0 M, 1.2 mL, 1.20 mmol) dropwise. The mixture was stirred for 15 minutes. Intermediate 16.2 (420 mg, 1.18 mmol) in THF (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was purified through flash chromatography on silica gel (EtOAc) to give the product (340 mg) as colorless oil in 81% yield.

EXAMPLE 16

4-[2-{(2R)-2-[(1E,3S)-3-hydroxyhept-1-enyl]-5-oxopyrrolidin-1-yl}ethyl) benzoic acid To a solution of Intermediate 16.3 (170 mg, 0.474 mmol) in MeOH/THF/H₂O (2/2/2 mL) was added NaOH (1.0 M, 1.18 mL, 1.18 mmol). The mixture was stirred for overnight. After concentration under reduced pressure, the residue was purified through RP-HPLC using ACN and H₂O/0.1% TFA to afford the desired product (89 mg) as a white solid. ¹H NMR (CD₃OD) δ 0.896 (t, J=7.3 Hz, 3H), 1.35 (m, 4H), 1.51 (m, 2H), 1.71 (m, 1H), 2.19 (m, 1H), 2.32 (m, 2H), 2.90 (m, 2H), 3.16 (m, 1H), 3.73 (m, 1H), 5.45 (dd, J=8.8 and 15.0 Hz, 1H), 5.63 (dd, J=6.2 and 15.0 Hz, 1H), 7.33 (d, J=7.6 Hz, 2H), 7.95 (d, J=7.6 Hz, 2H), MS (m/z): 346.6 (M+H⁺).

EXAMPLES 17 AND 18

4-[2-((2R)-2-{(1E)-3-[1-(4-chlorophenyl)cyclopentyl]-3-hydroxyprop-1-enyl}-5-oxopyrrolidin-1-yl)ethyl]benzoic acid

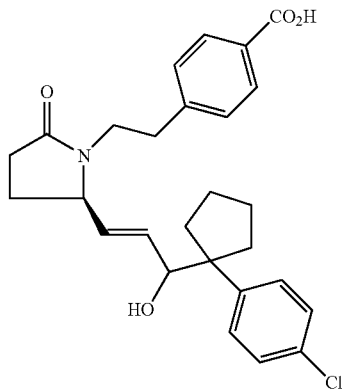

Intermediate 17.1. Methyl 1-(4-chlorophenyl)cyclopentanecarboxylate

To a solution of methyl 1-(4-chlorophenyl)cyclopentanecarboxylic acid (5.0 g, 22.25 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL0, dried over MgSO₄. The crude product was used for the next reaction without further purification.

Intermediate 17.2. Dimethyl 2-[1-(4chlorophenyl)cyclopentyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 17.1 (4.77 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (3.56 g) with colorless oil in 54% yield. $^1$H NMR (CDCl$_3$) δ 1.61 (m, 4H), 1.96 (m, 2H), 2.49 (m, 2H), 2.91 (d, J=21.3 Hz, 2H), 3.68 (s, 3H), 3.71 (s, 3H), 7.20 (d, J=8.8 Hz, 2H), 7.32 (d, J=8.8 Hz, 2H).

Intermediate 17.3. Methyl 4-[2-((2R)-2-{(1E)-3-[1-(4-chlorophenyl)cyclopentyl]-3-oxoprop-1-enyl}-5-oxopyrrolidin-1-yl)ethyl]benzoate To a solution of Intermediate 17.2 (480 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc/Hexanes 1/1) to give the product (520 mg) as a colorless oil in 75% yield. $^1$H NMR (CDCl$_3$) δ 1.60 (m, 4H), 1.93 (m, 2H), 2.27 (m, 2H), 2.41 (m, 2H), 2.78 (m, 2H), 3.67 (m, 1H), 3.92 (s, 3H), 5.98 (d, J=15.4 Hz, 1H), 6.50 (dd, J=8.4 and 15.4 Hz, 1H), 7.00 (m, 3H), 7.088 (d, J=8.4 Hz, 2H), 7.23 (d, J=8.4 Hz, 2H), 7.29 (d, J=8.4 Hz, 2H), 7.94 (d, J=8.4 Hz, 2H), MS (m/z) 502.8 (M+Na$^+$).

Intermediate 17.4. Methyl 4-[2-((2R)-2-{(1E)-3-[1-(4-chlorophenyl)cyclopentyl]-3-hydroxyprop-1-enyl}-5-oxopyrrolidin-1-yl)ethyl]benzoate To a solution of Intermediate 17.3 (520 mg, 1.08 mmol) in ethanol/water (20 mL, v/v (1:1)) was added cerium chloride (605.5 mg, 1.63 mmol) and sodium borohydride (81.94 mg, 2.17 mmol). The mixture was stirred for overnight. After evaporation of the solvent, the crude product was used for the next reaction without purification.

EXAMPLES 17 AND 18

4-[2-((2R)-2-{(1E)-3-[1-(4-chlorophenyl)cyclopentyl]-3-hydroxy prop-1-enyl}-5-oxopyrrolidin-1-yl)ethyl]benzoic acid To a solution of Intermediate 7.4 in MeOH/THF/H$_2$O (2/2/2 mL) was added NaOH (1.0 M, 2.7 mL, 2.7 mmol). The mixture was stirred for overnight. After concentration under reduced pressure, the residue was purified through RP-HPLC using ACN and H$_2$O/0.1% TFA to afford example 17 (118 mg) and example 18 (290 mg) as a white solid.

EXAMPLE 17

4-[2-((2R)-2-{(1E,3R)-3-[1-(4-chlorophenyl)cyclopentyl]-3-hydroxyprop-1-enyl}-5-oxopyrrolidin-1-yl)ethyl]benzoic acid (the first isomer in RP-HPLC: ACN/H$_2$O/TFA): $^1$HNMR (CD$_3$OD, ppm) δ 0.1.56 (m, 2H), 1.599 (m, 2H), 1.990 (m, 2H), 2.21 (m, 2H), 2.88 (m, 2H), 3.77 (m, 1H), 5.29 (dd, J=8.1 and 15.3 Hz, 1H), 5.33 (dd, J=7.0 and 15.3 Hz, 1H), 7.19 (d, J=8.8 Hz, 2H), 7.28 (d, J=8.8 Hz, 2H), 7.29 (d, J=8.4 Hz, 2H), 7.98 (d, J=8.4 Hz, 2H), MS (m/z) 468.3(M+H$^+$).

EXAMPLE 18

4-[2-((2R)-2-{(1E,3S)-3-[1-(4-chlorophenyl)cyclopentyl]-3-hydroxyprop-1-enyl}-5-oxopyrrolidin-1-yl)ethyl]benzoic acid (the second isomer in RP-HPLC: ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.29 (dd, J=8.1 and 15.3 Hz, 1H), 5.33 (dd, J=7.0 and 15.3 Hz, 1H), 7.19 (d, J=8.8 Hz, 2H), 7.28 (d, J=8.8 Hz, 2H), 7.29 (d, J=8.4 Hz, 2H), 7.98 (d, J=8.4 Hz, 2H), MS (m/z) 468.3(M+H$^+$).

EXAMPLES 19 AND 20

4-[2-((2R)-2-{(1E)-3-[1-(4-fluorophenyl)cyclopentyl]-3-hydroxyprop-1-enyl}-5-oxopyrrolidin-1-yl)ethyl]benzoic acid

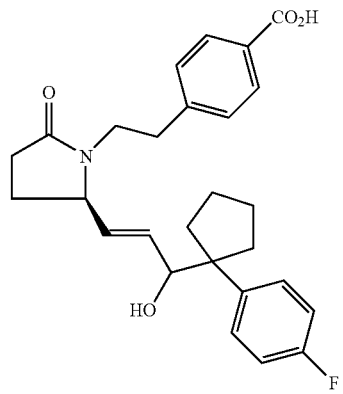

Intermediate 19.1. Methyl 1-(4-fluorophenyl)cyclopentanecarboxylate

To a solution of methyl 1-(4-fluorophenyl)cyclopentanecarboxylic acid (5.0 g, 24.01 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL), dried over MgSO$_4$. The crude product was used for the next reaction without further purification.

Intermediate 19.2. Dimethyl 2-[1-(4-fluorophenyl)cyclopentyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 19.1 (4.44 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (3.50 g) with colorless oil in 56% yield. $^1$H NMR (CDCl$_3$) δ 1.61 (m, 4H), 1.96 (m, 2H), 2.49 (m, 2H), 2.91 (d, J=21.3 Hz, 2H), 3.68 (s, 3H), 3.71 (s, 3H), 7.02 (d, J=8.4 Hz, 2H), 7.20 (m, 2H).

Intermediate 19.3. Methyl 4-[2-((2R)-2-{(1E)-3-[1-(4-fluorophenyl)cyclopentyl]3-oxoprop-1-enyl}-5-oxopyrrolidin-1-yl)ethyl]benzoate To a solution of Intermediate 19.2 (457 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with ethyl acetate (30 mL). The organic layer was washed with brine (3×5 mL), dried over MgSO$_4$. The residue was purified through flash chromatography on silica gel (EtOAc/Hexanes 1/1) to give the product (560 mg) as a colorless oil in 83% yield. $^1$H NMR (CDCl$_3$) δ 1.60 (m, 4H), 1.93 (m, 2H), 2.27 (m, 2H), 2.41 (m, 2H), 2.78 (m, 2H), 3.67 (m, 1H), 3.92 (s, 3H), 5.99 (d, J=15.3 Hz, 1H), 6.50 (dd, J=8.8 and 15.4 Hz, 1H), 7.01 (d, J=8.4 Hz, 2H), 7.09 (d, J=8.1 Hz, 2H), 7.24 (m, 2H), 7.92 (d, J=8.1 Hz, 2H), MS (m/z) 486.4 (M+Na$^+$).

Intermediate 19.4. Methyl 4-[2-((2R)-2-{(1E)-3-[1-(4-fluorophenyl)cyclopentyl]-3-hydroxyprop-1-enyl}-5-oxopyrrolidin-1-yl)ethyl]benzoate To a solution of Intermediate 19.3 (560 mg, 1.21 mmol) in ethanol/water (20 mL, v/v (1:1)) was added cerium chloride (675.1 mg, 1.81 mmol) and sodium borohydride (91.40 mg, 2.42 mmol). The mixture was stirred at RT for overnight. After evaporation of the solvent, the crude product was used for the next reaction without purification.

EXAMPLES 19 AND 20

4-[2-((2R)-2-{(1E)-3-[1-(4-fluorophenyl)cyclopentyl]-3-hydroxy prop-1-enyl}-5-oxopyrrolidin-1-yl)ethyl]benzoic acid To a solution of Intermediate 19.4 in MeOH/THF/H$_2$O (2/2/2 mL) was added NaOH (1.0 M, 3.02 mL, 3.02 mmol). The mixture was stirred for overnight. After concentration under reduced pressure, the residue was purified through RP-HPLC using ACN and H$_2$O/0.1% TFA to afford example 19 (160 mg) and example 20 (284 mg) as a white solid.

EXAMPLE 19

4-[2-((2R)-2-{(1E,3R)-3-[1-(4-fluorophenyl)cyclopentyl]-3-hydroxyprop-1-enyl}-5-oxopyrrolidin-1-yl)ethyl]benzoic acid (the first isomer in RP-HPLC: (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.28 (dd, J=8.1 and 15.4 Hz, 1H), 5.33 (dd, J=7.0 and 15.4 Hz, 1H), 6.96 (d, J=8.8 Hz, 2H), 7.29 (m, 4H), 7.98 (d, J=8.1 Hz, 2H), MS (m/z) 452.3 (M+H$^+$).

EXAMPLE 20

4-[2-((2R)-2-{(1E,3S)-3-[1-(4-fluorophenyl)cyclopentyl]-3-hydroxyprop-1-enyl}-5-oxopyrrolidin-1-yl)ethyl]benzoic acid (the second isomer in RP-HPLC: (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.28 (dd, J=8.1 and 15.4 Hz, 1H), 5.33 (dd, J=7.0 and 15.4 Hz, 1H), 6.96 (d, J=8.8 Hz, 2H), 7.29 (m, 4H), 7.98 (d, J=8.1 Hz, 2H), MS (m/z) 452.3 (M+H$^+$).

EXAMPLES 21 AND 22

4-[2-((2R)-2-{(1E)-3-[1-(2-fluorophenyl)cyclopentyl]-3-hydroxy prop-1-enyl}-5-oxopyrrolidin-1-yl)ethyl]benzoic acid

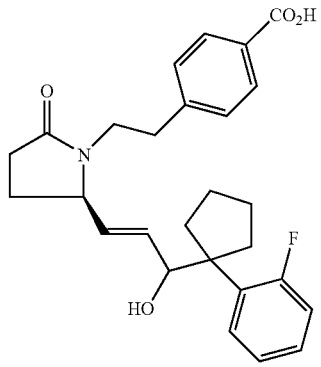

Intermediate 21.1. Methyl 1-(2-fluorophenyl)cyclopentanecarboxylate

To a solution of methyl 1-(2-fluorophenyl)cyclopentanecarboxylic acid (5.0 g, 24.01 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL), dried over MgSO$_4$. The crude product was used for the next reaction without further purification.

Intermediate 21.2. Dimethyl 2-[1-(2-fluorophenyl)cyclopentyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 21.1 (4.44 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (3.50 g) with colorless oil in 56% yield. $^1$H NMR (CDCl$_3$) δ 1.61 (m, 4H), 1.96 (m, 2H), 2.49 (m, 2H), 2.91 (d, J=21.3 Hz, 2H), 3.68 (s, 3H), 3.71 (s, 3H), 7.04 (t, J=8.4 Hz, 1H), 7.16 (d, J=8.4 Hz, 1H), 7.25 (m, 1H), 7.37 (t, J=8.4 Hz, 1H).

Intermediate 21.3. Methyl 4-[2-((2R)-2-{(1E)-3-[1-(2-fluorophenyl)cyclopentyl]-3-oxoprop-1-enyl}-5-oxopyrrolidin-1-yl)ethyl]benzoate To a solution of Intermediate 21.2 (457 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$. The residue was purified through flash chromatography on silica gel (EtOAc/Hexanes 1/1) to give the product (440 mg) as a colorless oil in 65% yield. $^1$H NMR (CDCl$_3$) δ 1.60 (m, 4H), 1.93 (m, 2H), 2.27 (m, 2H), 2.41 (m, 2H), 2.78 (m, 2H), 3.67 (m, 1H), 3.92 (s, 3H), 5.94 (d, J=15.4 Hz, 1H), 6.51 (dd, J=8.1 and 15.4 Hz, 1H), 6.97 (t, J=8.3, 1H), 7.09 (d, J=8.1 Hz, 2H), 7.21 (m, 2H), 7.40 (t, J=8.3 Hz, 1H), 7.92 (d, J=8.1 Hz, 2H), MS (m/z) 486.6 (M+Na$^+$).

Intermediate 21.4. Methyl 4-[2-((2R)-2-{(1E)-3-[1-(2-fluorophenyl)cyclopentyl]-3-hydroxyprop-1-enyl}-5-oxopyrrolidin-1-yl)ethyl]benzoate To a solution of Intermediate 21.3 (440 mg, 0.949 mmol) in ethanol/water (20 mL, v/v (1:1)) was added cerium chloride (530.5 mg, 1.43 mmol) and sodium borohydride (71.82 mg, 1.89 mmol). The mixture was stirred at RT for overnight. After evaporation of the solvent, the crude product was used for the next reaction without purification.

EXAMPLES 21 AND 22

4-[2-((2R)-2-{(1E)-3-[1-(2-fluorophenyl)cyclopentyl]-3-hydroxy prop-1-enyl}-5-oxopyrrolidin-1-yl) ethyl]benzoic acid To a solution of Intermediate 21.4 in MeOH/THF/H$_2$O (2/2/2 mL) was added NaOH (1.0 M, 2.37 mL, 2.37 mmol). The mixture was stirred for overnight. After concentration under reduced pressure, the residue was purified through RP-HPLC using ACN and H$_2$O/0.1% TFA to afford example 21 (94 mg) and example 22 (220 mg) as a white solid.

EXAMPLE 21

4-[2-((2R)-2-{(1E,3R)-3-[1-(2-fluorophenyl)cyclopentyl]-3-(3S)hydroxy prop-1-enyl}-5-oxopyrrolidin-1-yl) ethyl]benzoic acid (the first isomer in RP-HPLC (ACN/H$_2$O 0.1% TFA): $^1$H NMR (CD$_3$OD) δ 0.1.56 (m, 2H), 1.599 (m, 2H), 1.990 (m, 2H), 2.21 (m, 2), 2.88 (m, 2H), 3.77 (m, 1H), 5.23 (dd, J=8.8 and 15.0 Hz, 1H), 5.44 (dd, J=7.0 and 15.0 Hz, 1H), 6.99 (m, 2H), 7.19 (m, 1H), 7.28 (d, J=8.0 Hz, 2H), 7.29 (m, 1H), 7.98 (d, J=8.0 Hz, 2H), MS (m/z) 452.3 (M+H$^+$).

EXAMPLE 22

4-[2-((2R)-2-{(1E,3S)-3-[1-(2-fluorophenyl)cyclopentyl]-3-(3S)hydroxy prop-1-enyl}-5-oxopyrrolidin-1-yl) ethyl]benzoic acid (the second isomer in RP-HPLC (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.23 (dd, J=8.8 and 15.0 Hz, 1H), 5.44 (dd, J=7.0 and 15.0 Hz, 1H), 6.99 (m, 2H), 7.19 (m, 1H), 7.28 (d, J=8.0 Hz, 2H), 7.29 (m, 1H), 7.98 (d, J=8.0 Hz, 2H), MS (m/z) 452.3 (M+H$^+$).

EXAMPLES 23 AND 24

4-[2-((2R)-2-{(1E)-3-[1-(4-methylphenyl)cyclopentyl]-3-hydroxyprop-1-enyl}-5-oxopyrrolidin-1-yl) ethyl]benzoic acid

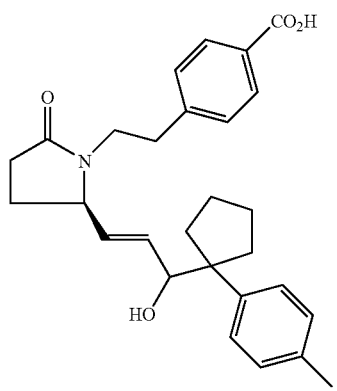

Intermediate 23.1. Methyl 1-(4-methylphenyl)cyclopentanecarboxylate

To a solution of methyl 1-(2-fluorophenyl)cyclopentanecarboxylic acid (5.0 g, 24.48 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL), dried over MgSO$_4$. The crude product was used for the next reaction without further purification.

Intermediate 23.2. Dimethyl 2-[1-(4-methylphenyl)cyclopentyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 23.1 (4.36 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (4.30 g) with colorless oil in 69% yield. $^1$H NMR (CDCl$_3$) δ 1.61 (m, 4H), 1.96 (m, 2H), 2.27 (s, 3H), 2.49 (m, 2H), 2.91 (d, J=21.3 Hz, 2H), 3.68 (s, 3H), 3.71 (s, 3H), 7.13 (s, 4H).

Intermediate 23.3. Methyl 4-[2-((2R)-2-{(1E)-3-[1-(4-methylphenyl)cyclopentyl]-3-oxoprop-1-enyl}-5-oxopyrrolidin-1-yl)ethyl]benzoate To a solution of Intermediate 23.2 (451.4 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc/Hexanes 1/1) to give the product (520 mg) as a colorless oil in 78% yield. $^1$H NMR (CDCl$_3$) δ 1.60 (m, 4H), 1.93 (m, 2H), 2.27 (m, 2H), 2.28 (s, 3H), 2.41 (m, 2H), 2.78 (m, 2H), 3.67 (m, 1H), 3.92 (s, 3H), 6.03 (d, J=15.4 Hz, 1H), 6.45 (dd, J=8.1 and 15.4 Hz, 1H), 7.06 (d, J=8.2 Hz, 2H), 7.12 (s, 4H), 7.90 (d, J=8.2 Hz, 2H), MS (m/z) 482.7 (M+Na$^+$).

Intermediate 23.4. Methyl 4-[2-((2R)-2-{(1E)-3-[1-(4-methylphenyl)cyclopentyl]-3-hydroxyprop-1-enyl}-5-oxopyrrolidin-1-yl)ethyl]benzoate To a solution of Intermediate 23.3 (520 mg, 1.13 mmol) in ethanol/water (20 mL, v/v (1:1)) was added cerium chloride (632 mg, 1.69 mmol) and sodium borohydride (85.61 mg, 2.26 mmol). The mixture was stirred at RT for overnight. After evaporation of the solvent, the crude product was used for the next reaction without purification.

EXAMPLES 23 AND 24

4-[2-((2R)-2-{(1E)-3-[1-(4-methylphenyl)cyclopentyl]-3-hydroxy prop-1-enyl}-5-oxopyrrolidin-1-yl) ethyl]benzoic acid To a solution of Intermediate 23.4 in MeOH/THF/H$_2$O (2/2/2 mL) was added NaOH (1.0 M, 2.82 mL, 2.82 mmol).

The mixture was stirred for overnight. After concentration under reduced pressure, the residue was purified through RP-HPLC using ACN and H$_2$O/0.1% TFA to afford example 23 (133 mg) and example 24 (265 mg) as a white solid.

EXAMPLE 23

4-[2-((2R)-2-{(1E,3R)-3-[1-(4-methylphenyl)cyclopentyl]-3-hydroxyprop-1-enyl}-5-oxopyrrolidin-1-yl)ethyl]benzoic acid (the first isomer in RP-HPLC (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.24 (s, 3H), 2.88 (m, 2H), 3.77 (m, 1H), 5.23 (dd, J=8.4 and 15.4 Hz, 1H), 5.44 (dd, J=8.0 and 15.0 Hz, 1H), 7.03 (d, J=8.0 Hz, 2H), 2.90 (d, J=6.9 Hz, 2H), 7.32 (d, J=6.9 Hz, 2H), 7.95 (d, J=8.0 Hz, 2H), MS (m/z) 448.5 (M+H$^+$).

EXAMPLE 24

4-[2-((2R)-2-{(1E,3S)-3-[1-(4-methylphenyl)cyclopentyl]-3-hydroxyprop-1-enyl}-5-oxopyrrolidin-1-yl)ethyl]benzoic acid (the second isomer in RP-HPLC (ACN/H$_2$O 0.1% TFA): $^1$H NMR(CD$_3$OD) δ 0.1.56 (m, 2H), 1.599 (m, 2H), 1.990 (m, 2H), 2.21 (m, 2H), 2.24 (s, 3H), 2.88 (m, 2H), 3.77 (m, 1H), 5.23 (dd, J=8.4 and 15.4 Hz, 1H), 5.44 (dd, J=8.0 and 15.0 Hz, 1H), 7.03 (d, J=8.0 Hz, 2H), 2.90 (d, J=6.9 Hz, 2H), 7.32 (d, J=6.9 Hz, 2H), 7.95 (d, J=8.0 Hz, 2H), MS (m/z) 448.5 (M+H$^+$).

EXAMPLES 25 AND 26

4-[2-((2R)-2-{(1E)-3-[1-(4-chlorophenyl)cyclobutyl]-3-hydroxy prop-1-enyl}-5-oxopyrrolidin-1-yl) ethyl]benzoic acid

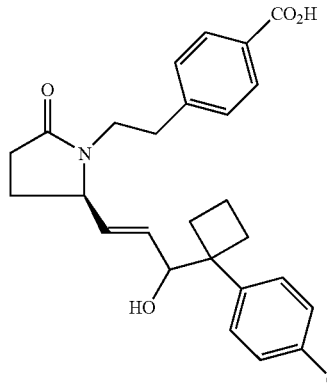

Intermediate 25.1. Methyl 1-(4-chlorophenyl)cyclobutanecarboxylate

To a solution of methyl 1-(4-chlorophenyl)cyclobutanecarboxylic acid (5.0 g, 23.73 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL), dried over MgSO$_4$. The crude product was used for the next reaction without further purification.

Intermediate 25.2. Dimethyl 2-[1-(4-chlorophenyl)cyclobutyl]-2-oxoethyl phosphonate To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 25.1 (4.50 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (4.36 g) with colorless oil in 65% yield. $^1$H NMR (CDCl$_3$) δ 1.61 (m, 2H), 1.96 (m, 2H), 2.49 (m, 2H), 2.91 (d, J=21.3 Hz, 2H), 3.68 (s, 3H), 3.71 (s, 3H), 7.16 (d, J=8.8 Hz, 2H), 7.32 (d, J=8.8 Hz, 2H).

Intermediate 25.3. Methyl 4-[2-((2R)-2-{(1E)-3-[1-(4-chlorophenyl)cyclobutyl]-3-oxoprop-1-enyl}-5-oxopyrrolidin-1-yl)ethyl]benzoate To a solution of Intermediate 25.2 (460.8 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc/Hexanes 1/1) to give the product (380 mg) as a colorless oil in 71% yield. $^1$H NMR (CDCl$_3$) δ 1.60 (m, 2H), 1.93 (m, 2H), 2.27 (m, 2H), 2.41 (m, 4H), 2.78 (m, 4H), 3.67 (m, 1H), 3.92 (s, 3H), 5.98 (d, J=15.4 Hz, 1H), 6.50 (dd, J=8.4 and 15.4 Hz, 1H), 7.00 (m, 3H), 7.088 (d, J=8.0 Hz, 2H), 7.15 (d, J=8.4 Hz, 2H), 7.30 (d, J=8.4 Hz, 2H), 7.94 (d, J=8.0 Hz, 2H), MS (m/z) 488.6 (M+Na$^+$).

Intermediate 25.4. Methyl 4-[2-((2R)-2-{(1E)-3-[1-(4-chlorophenyl)cyclobutyl]-3-hydroxyprop-1-enyl}-5-oxopyrrolidin-1-yl)ethyl]benzoate To a solution of Intermediate 25.3 (480 mg, 1.03 mmol) in ethanol/water (20 mL, v/v (1:1)) was added cerium chloride (575.7 mg, 1.55 mmol) and sodium borohydride (77.93 mg, 2.06 mmol). The mixture was stirred for overnight. After evaporation of the solvent, the crude product was used for the next reaction without purification.

EXAMPLES 25 AND 26

4-[2-((2R)-2-{(1E)-3-[1-(4-chlorophenyl)cyclobutyl]-3-hydroxy prop-1-enyl}-5-oxopyrrolidin-1-yl) ethyl]benzoic acid To a solution of Intermediate 25.4 in MeOH/THF/H$_2$O (2/2/2 mL) was added NaOH (1.0 M, 2.57 mL, 2.57 mmol). The mixture was stirred for overnight. After concentration under reduced pressure, the residue was purified through RP-HPLC using ACN and H$_2$O/0.1% TFA to afford the desired product (130 mg) and the second isomer (230 mg) as a white solid.

EXAMPLE 25

4-[2-((2R)-2-{(1E,3R)-3-[1-(4-chlorophenyl)cyclobutyl]-3-hydroxyprop-1-enyl}-5-oxopyrrolidin-1-yl)ethyl]benzoic acid (the first isomer in RP-HPLC (ACN/H$_2$O 0.1% TFA): $^1$H NMR (CD$_3$OD) δ 0.1.56 (m, 2H), 1.990 (m, 2H), 2.21 (m, 2H), 2.42 (m, 4H), 2.88 (m, 4H), 3.77 (m, 1H), 5.29 (dd, J=8.4 and 15.3 Hz, 1H), 5.33 (dd, J=6.6 and 15.3 Hz, 1H), 7.19 (d, J=8.8 Hz, 2H), 7.28 (d, J=8.8 Hz, 2H), 7.29 (d, J=8.4 Hz, 2H), 7.98 (d, J=8.4 Hz, 2H), MS (m/z) 454.3 (M+H$^+$).

EXAMPLE 26

4-[2-((2R)-2-{(1E,3S)-3-[1-(4-chlorophenyl)cyclobutyl]-3-hydroxyprop-1-enyl}-5-oxopyrrolidin-1-yl)ethyl]benzoic acid (the second isomer in RP-HPLC (ACN/H2O 0.1% TFA): $^1$H NMR (CD$_3$OD) δ 0.1.56 (m, 2H), 1.990 (m, 2H), 2.21 (m, 2H), 2.42 (m, 4H), 2.88 (m, 4H), 3.77 (m, 1H), 5.29 (dd, J=8.4 and 15.3 Hz, 1H), 5.33 (dd, J=6.6 and 15.3 Hz, 1H), 7.19 (d, J=8.8 Hz, 2H), 7.28 (d, J=8.8 Hz, 2H), 7.29 (d, J=8.4 Hz, 2H), 7.98 (d, J=8.4 Hz, 2H), MS (m/z) 454.3 (M+H$^+$).

EXAMPLES 27 AND 28

4-[2-((2R)-2-{(1E)-3-[1-(phenyl)cyclopentyl]-3-hydroxyprop-1-enyl}-5-oxopyrrolidin-1-yl)ethyl]benzoic acid

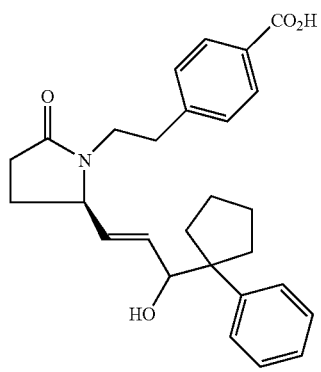

Intermediate 27.1. Methyl 1-(phenyl)cyclopentanecarboxylate

To a solution of methyl 1-(2-fluorophenyl)cyclopentanecarboxylic acid (10 g, 52.56 mmol) in anhydrous methanol was added 1 mL of the concentration of sulfuric acid. The mixture was refluxed for overnight. The mixture was neutralized to pH 4-5 with sodium carbonate. The solvent was evaporated. The residue was dissolved in ethyl acetate (50 mL), washed with brine (3×10 mL), dried over MgSO$_4$. The crude product was used for the next reaction without further purification.

Intermediate 27.2. Dimethyl 2-[1-(phenyl)cyclopentyl]-2-oxoethylphosphonate

To a solution of dimethyl methylphosphonate (4.32 mL, 40 mmol) in anhydrous THF (30 mL), cooled at −78° C. was added n-BuLi (1.6 M in hexane, 27.50 mL, 44 mmol). The mixture was stirred for 30 minutes at this temperature under nitrogen. Intermediate 27.1 (4.09 g, 20 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc/Hexanes 1/1) to give the product (3.43 g) with colorless oil in 58% yield. $^1$H NMR (CDCl$_3$) δ 1.61 (m, 4H), 1.96 (m, 2H), 2.49 (m, 2H), 2.91 (d, J=21.3 Hz, 2H), 3.68 (s, 3H), 3.71 (s, 3H), 7.25 (m, 5H).

Intermediate 27.3. Methyl 4-[2-((2R)-2-{(1E)-3-[1-(phenyl)cyclopentyl]-3-oxo prop-1-enyl}-5-oxopyrrolidin-1-yl)ethyl]benzoate To a solution of Intermediate 27.2 (430.82 mg, 1.455 mmol) in anhydrous THF (15 mL) at 0° C. was added 60% NaH (58.2 mg, 1.455 mmol) in mineral oil. The mixture was stirred for 10 minutes. Intermediate 1.4 (400 mg, 1.455 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc/Hexanes 1/1) to give the product (520 mg) as a colorless oil in 83% yield. $^1$H NMR (CDCl$_3$) δ 1.60 (m, 4H), 1.93 (m, 2H), 2.27 (m, 2H), 2.41 (m, 2H), 2.78 (m, 2H), 3.67 (m, 1H), 3.92 (s, 3H), 6.01 (d, J=15.4 Hz, 1H), 6.49 (dd, J=8.1 and 15.4 Hz, 1H), 7.24 (m, 5H), 7.90 (d, J=8.2 Hz, 2H), MS (m/z) 446.5 M+H$^+$).

Intermediate 27.4. Methyl 4-[2-((2R)-2-{(1E)-3-[1-(phenyl)cyclopentyl]-3-hydroxyprop-1-enyl}-5-oxopyrrolidin-1-yl)ethyl]benzoate To a solution of Intermediate 27.3 (520 mg, 1.17 mmol) in ethanol/water (20 mL, v/v (1:1)) was added cerium chloride (652.2 mg, 1.75 mmol) and sodium borohydride (88.3 mg, 2.33 mmol). The mixture was stirred for overnight. After evaporation of the solvent, the crude product was used for the next reaction without purification.

EXAMPLES 27 AND 28

4-[2-((2R)-2-{(1E)-3-[1-(phenyl)cyclopentyl]-3-hydroxyprop-1-enyl}-5-oxopyrrolidin-1-yl)ethyl]benzoic acid To a solution of Intermediate 27.4 in MeOH/THF/H$_2$O (2/2/2 mL) was added NaOH (1.0 M, 2.91 mL, 2.91 mmol). The mixture was stirred for overnight. After concentration under reduced pressure, the residue was purified through RP-HPLC using ACN and H$_2$O/0.1% TFA to afford example 27 (150 mg) and example 28 (314 mg) as a white solid.

EXAMPLE 27

4-[2-((2R)-2-{(1E,3R)-3-[1-(phenyl)cyclopentyl]-3-hydroxyprop-1-enyl}-5-oxopyrrolidin-1-yl)ethyl]benzoic acid (the first isomer in RP-HPLC (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.23 (dd, J=8.4 and 15.4 Hz, 1H), 5.44 (dd, J=8.0 and 15.0 Hz, 1H), 7.03 (d, J=8.0 Hz, 2H), 7.30 (m, 5H), 7.95 (d, J=8.0, 2H), MS (m/z) 434.3 (M+H$^+$).

EXAMPLE 28

4-[2-((2R)-2-{(1E,3s)-3-[1-(phenyl)cyclopentyl]-3-hydroxyprop-1-enyl}-5-oxopyrrolidin-1-yl)ethyl]benzoic acid (the first isomer in RP-HPLC (ACN/H$_2$O 0.1% TFA): $^1$H NMR (CD$_3$OD) δ 0.1.56 (m, 2H), 1.599 (m, 2H), 1.990 (m, 2H), 2.21 (m, 2H), 2.88 (m, 2H), 3.77 (m, 1H), 5.23 (dd, J=8.4 and 15.4 Hz, 1H), 5.44 (dd, J=8.0 and 15.0 Hz, 1H), 7.03 (d, J=8.0 Hz, 2H), 7.30 (m, 5H), 7.95 (d, J=8.0, 2H), MS (m/z) 434.3 (M+H$^+$).

EXAMPLE 29

4-(2-{(2R)-2-[(1E,3S)-3-hydroxy-6-methoxyhex-1-enyl]-5-oxo pyrrolidin-1-yl}ethyl)benzoic acid

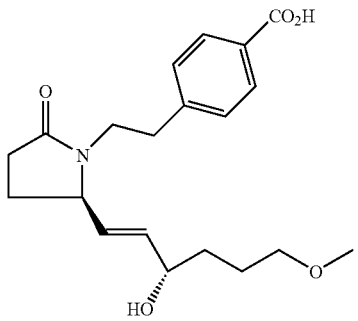

Intermediate 29.1. Methyl 4-(2-{(2R)-2-[(1E)-6-methoxy-3-oxohex-1-enyl]5-oxopyrrolidin-1-yl}ethyl)benzoate To a solution of dimethyl 5-methoxy-2-oxopentylphosphonate (160 mg, 0.714 mmol), prepared from methyl 4-methoxybutyrate, dimethyl methylphosphonate and n-BuLi, in anhydrous THF (15 mL) at 0° C. was added 60% NaH (31.4 mg, 0.785 mmol) in mineral oil. The mixture was stirred for 10 minutes. Intermediate 1.4 (196 mg, 0.714 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc/Hexanes 1/1) to give the product (195 mg) as a colorless oil in 73% yield. $^1$H NMR (CDCl$_3$) δ 1.75 (m, 2H), 1.87 (t, J=7.0 Hz, 2H), 2.15 (m, 1H), 2.33 (m, 1H), 2.62 (t, J=7.0 Hz, 2H), 2.90 (m, 2H), 3.07 (m, 1H), 3.30 (s, 3H), 3.38 (t, J=6.2 Hz, 2H), 3.86 (m, 2H), 3.90 (s, 3H), 6.07 (d, J=15.3 Hz, 1H), 6.47 (dd, J=8.1 and 15.3 Hz, 1H), 7.25 (d, J=6.6 Hz, 2H), 7.97 (d, J=6.6 Hz, 2H).

Intermediate 29:2. Methyl 4-(2-{(2R)-2-[(1E,3S)-3-hydroxy-6-methoxy-hex-1-enyl]-5-oxopyrrolidin-1-yl}ethyl)benzoate To a solution of (R)-2-methyl-CBS-oxazaborolidine (1.0 M in toluene, 0.48 mL, 0.48 mmol) in anhydrous THF at 0° C. was added Borane-THF complex (1.0 M, 0.48 mL, 0.48 mmol) dropwise. The mixture was stirred for 15 minutes. Intermediate 29.1 (180 mg, 0.48 mmol) in THF (3 mL) was added dropwise. The mixture was stirred for 3 hours. The mixture was quenched with addition of 1 mL of the saturated ammonia chloride and was dilute with EtOAc (50 mL). The organic layer was washed with brine (3×5 mL), dried over MgSO4. The residue was used for the next reaction without purification.

EXAMPLE 29

4(2-{(2R)-2-[(1E,3S)-3-hydroxy-6-methoxyhex-1-enyl]-5-oxo pyrrolidin-1-yl}ethyl)benzoic acid To a solution of Intermediate 29.3 in MeOH/THF/H$_2$O (2/2/2 mL) was added NaOH (1.0 M, 1.21 mL, 1.21 mmol). The mixture was stirred for overnight. After concentration under reduced pressure, the residue was purified through RP-HPLC using ACN and H$_2$O/0.1% TFA to afford the desired product (150 mg) as a white solid. $^1$HNMR (CD$_3$OD, ppm) δ 1.75 (m, 2H), 2.15 (m, 2H), 2.33 (m, 2H), 2.62 (t, J=7.0 Hz, 2H), 2.90 (m, 2H), 3.07 (m, 1H), 3.30 (s, 3H), 3.38 (t, J=6.2 Hz, 2H), 3.86 (m, 2H), 4.80 (m, 1H), 6.07 (d, J=15.3 Hz, 1H), 6.47 (dd, J=8.1 and 15.3 Hz, 1H), 7.25 (d, J=6.6 Hz, 2H), 7.97 (d, J=6.6 Hz, 2H).

EXAMPLE 30

4(2-{(2R)-2-[(1E,3S)-3-hydroxy-4-cyclohexyl-but-1-enyl]-5-oxo pyrrolidin-1-yl}ethyl)benzoic acid

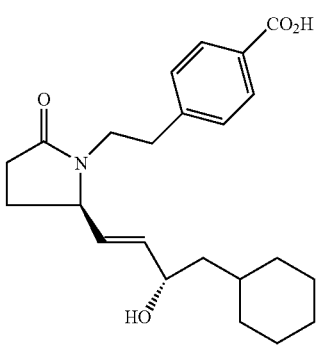

Intermediate 30.1. Methyl 4-(2-{(2R)-2-[(1E)-4-cyclohexyl-3-oxobutyl-1-enyl]-5-oxopyrrolidin-1-yl}ethyl)benzoate To a solution of dimethyl 3-cyclohexyl-2-oxo-propylphosphonate (225.4 mg, 0.908 mmol), prepared from methyl cyclohexylacetate and dimethyl methylphosphonate and butyllithium, in anhydrous THF (15 mL) at 0° C. was added 60% NaH (40 mg, 1.0 mmol) in mineral oil. The mixture was stirred for 10 minutes. Intermediate 1.4 (250 mg, 0.908 mmol) in THF (5 mL) was added dropwise. The mixture was stirred for overnight. The mixture was quenched with addition of the saturated ammonia chloride. The mixture was dilute with Ethyl acetate (30 mL). The organic layer was washed with brine (3×5 mL), dried over MgSO$_4$, The residue was purified through flash chromatography on silica gel (EtOAc:Hexanes=1:1) to give the product (260 mg) as white solid in 73% yield. $^1$HNMR (CDCl$_3$, ppm) δ 0.888 (m, 4H), 1.26 (m, 4H), 1.66 (m, 6H), 2.22 (m, 1H), 2.38 (m, 3H), 2.82 (m, 1H), 2.92 (m, 1H), 3.08 (m, 1H), 3.86 (m, 1H), 3.90 (s, 3H) 6.06 (d, J=15.7 Hz, 1H), 6.43 (dd, J=8.0 and 15.4 Hz, 1H), 7.25 (d, J=8.5 Hz, 2H), 7.97 (d, J=8.5 Hz, 2H).

Intermediate 30.2. Methyl 4-(2-{(2R)-2-[(1E,3S)-3-hydroxy-4-cyclohexyl-but-1-enyl]-5-oxopyrrolidin-1-yl}ethyl)benzoate To a solution of (R)-2-methyl-CBS-oxazaborolidine (1.0 M in toluene, 0.654 mL, 0.654 mmol) in anhydrous THF at 0° C. was added Borane-THF complex (1.0 M, 0.654 mL, 0.654 mmol) dropwise. The mixture was stirred for 15 minutes. Intermediate 30.1 (260 mg, 0.654 mmol) in THF (3 mL) was added dropwise. The mixture was stirred for 3 hours. The mixture was quenched with addition of 1 mL of the saturated ammonia chloride and was dilute with EtOAc (50 mL). The organic layer was washed with brine (3×5 mL), dried over MgSO4. The residue was used for the next reaction without purification.

EXAMPLE 30

4-(2-{(2R)-2-[(1E,3S)-3-hydroxy-4-cyclohexyl-but-1-enyl]-5-oxopyrrolidin-1-yl}ethyl)benzoic acid To a solution of Intermediate 30.2 in MeOH/THF/H$_2$O (2/2/2 mL) was added NaOH (1.0 M, 1.21 mL, 1.21 mmol). The mixture was stirred for overnight. After concentration under reduced pressure, the residue was purified through RP-HPLC using ACN and H$_2$O/0.1% TFA to afford the desired product (79.4 mg) as a white solid. $^1$HNMR (CD$_3$OD, ppm) δ 0.888 (m, 4H), 1.26 (m, 4H), 1.66 (m, 6H), 2.22 (m, 1H), 2.32 (m, 2H), 2.82 (m, 1H), 2.82 (m, 2H), 3.08 (m, 1H), 3.77 (m, 1H), 4.03 (m, 1H), 4.16 (m, 1H), 5.45 (dd, J=8.8 and 15.4 Hz, 1H), 5.63 (dd, J=6.3 and 15.4 Hz, 1H), 7.33 (d, J=8.1 Hz, 2H), 7.96 (d, J=8.1 Hz, 2H), MS (m/z): 386.3 (M+H$^+$).

EXAMPLE 31

4-[2-{(2R)-2-[(1E,3S)-3-hydroxy-4-phenylbut-1-enyl]-5-oxopyrrolidin-1-yl}ethyl)benzoic acid

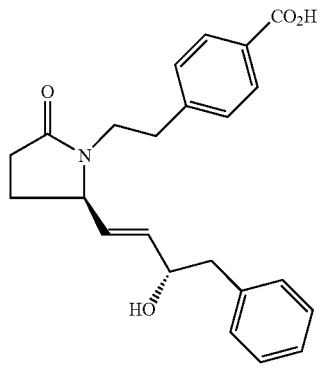

Intermediate 31.1. Dimethyl 2-oxo-3-phenylpropylphosphonate

To a solution of dimethyl methylphosphonate (2.16 mL, 20 mmol) in anhydrous THF (30 mL), cooled at −78° C. was added n-BuLi (1.6 M in hexane, 13.75 mL, 22 mmol). The mixture was stirred for 30 minutes at this temperature under nitrogen. Methyl phenylacetate (1.40 mL, 10 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (MeOH: CH$_2$Cl$_2$=2:98) to give the product (1.50 g) with colorless oil in 62% yield. $^1$HNMR (CDCl$_3$, ppm) δ 3.074 (d, J=21 Hz, 2H), 3.760 (s, 3H), 3.762 (s, 3H), 3.86 (s, 2H), 7.31 (m, 5H).

Intermediate 31.2. Methyl 4-(2-{(5R)-2-oxo-5-[(1E)-3-oxo-4-phenylbut-1-enyl]pyrrolidin-1-yl}ethyl)benzoate To a solution of Intermediate 31.1 (107.3 mg, 0.443 mmol) in anhydrous THF (10 mL) at 0° C. was added 60% NaH (17.73 mg, 0.443 mmol) in mineral oil. The mixture was stirred for 10 minutes. Intermediate 1.4 (122 mg, 0.443 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$, The residue was purified through flash chromatography on silica gel (EtOAc:Hexanes=1:1) to give the product (120 mg) as a colorless oil in 69% yield. $^1$HNMR (CDCl$_3$, ppm) δ 1.66 (m, 2H), 2.12 (m, 2H), 2.34 (m, 2H), 2.83 (m, 2H), 3.75 (s, 2H), 3.80 (m, 1H), 3.90 (s, 3H), 6.06 (d, J=15.8 Hz, 1H), 6.50 (dd, J=8.1 and 15.8 Hz, 1H), 7.19 (m, 7H), 7.92 (d, J=8.4 Hz, 2H). (m/z) 392.4 (M+H$^+$).

Intermediate 31.3. Methyl 4-(2-{(2R)-2-[(1E,3S)-3-hydroxy-4-phenylbut-1-enyl]-5-oxopyrrolidin-1-yl}ethyl)benzoate To a solution of (R)-2-methyl-CBS-oxazaborolidine (1.0 M in toluene, 0.51 mL, 0.51 mmol) in anhydrous THF at 0° C. was added Borane-THF complex (1.0 M, 0.51 mL, 0.51 mmol) dropwise. The mixture was stirred for 15 minutes. Intermediate 31.2 (200 mg, 0.51 mmol) in THF (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was purified through flash chromatography on silica gel (EtOAc) to give the product (150 mg) as colorless oil in 77% yield.

EXAMPLE 31

4-[2-{(2R)-2-[(1E,3S)-3-hydroxy-4-phenylbut-1-enyl]-5-oxopyrrolidin-1-yl]ethyl)benzoic acid To a solution of Intermediate 31.3 (150 mg, 0.381 mmol) in MeOH/THF/H$_2$O (2/2/2 mL) was added NaOH (1.0 M, 0.95 mL, 0.95 mmol). The mixture was stirred for overnight. After concentration under reduced pressure, the residue was purified through RP-HPLC using ACN and H$_2$O/0.1% TFA to afford the desired product (89 mg) as a white solid. $^1$HNMR (CD$_3$OD, ppm) δ 1.60 (m, 1H), 2.12 (m, 1H), 2.23 (m, 2H), 2.75 (m, 4H), 2.92 (dd, J=8.2 and 13.5 Hz, 1H), 3.54 (m, 1H), 3.88 (m, 1H), 4.31 (m, 1H), 5.26 (dd, J=7.7 and 14.3 Hz, 1H), 5.58 (dd, J=6.6 and 14.3 Hz, 1H), 7.19 (m, 5H), 7.23 (d, J=8.4 Hz, 2H), 7.95 (d, J=8.4 Hz, 2H), MS (m/z) 380.6 (M+H$^+$), 402.2 (M+Na$^+$).

EXAMPLE 32

4-[2-{(2R)-2-[(1E,3S)-3-hydroxy-oct-1-en-7-nyyl]-5-oxopyrrolidin-1-yl}ethyl)benzoic acid

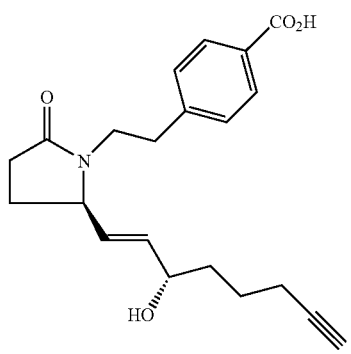

Intermediate 32.1. Dimethyl 2-oxohept-6-ynylphosphonate

To a solution of dimethyl methylphosphonate (2.16 mL, 20 mmol) in anhydrous THF (30 mL), cooled at −78° C. was added n-BuLi (1.6 M in hexane, 13.75 mL, 22 mmol). The mixture was stirred for 30 minutes at this temperature under nitrogen. Methyl hexynoate (1.26 g, 10 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over $MgSO_4$. The residue was purified through flash chromatography on silica gel ($MeOH:CH_2Cl_2=2:98$) to give the product (370 mg) with colorless oil in 17% yield. $^1HNMR$ ($CDCl_3$, ppm) δ 1.80 (t, J=7.0 Hz, 2H), 1.95 (s, 1H), 2.24 (dt, J=2.9 and 7.0 Hz, 2H), 2.73 (t, J=7.0 Hz, 2H), 3.06 (d, J=22.7 Hz, 2H), 3.77 (s, 3H), 3.70 (s, 3H).

Intermediate 32.2. Methyl 4-(2-{(2R)-[(1E)-3-oxooct-1-en-7-ynyl]-5-oxopyrrolidin-1-yl}ethyl)benzoate To a solution of Intermediate 32.1 (198.1 mg, 0.908 mmol) in anhydrous THF (10 mL) at 0° C. was added 60% NaH (43.6 mg, 1.17 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over $MgSO_4$. The crude product was used for the next reaction without further purification. $^1HNMR$ ($CDCl_3$, ppm) δ 1.02 (s, 9H), 1.74 (m, 1H), 2.15 (m, 1H), 2.34 (m, 2H), 2.39 (s, 2H), 2.83 (m 1H), 2.92 (m, 1H), 3.06 (m, 1H), 6.02 (d, J=15.7 Hz, 1H), 6.40 (dd, J=8.0 and 15.7 Hz, 1H), 7.24 (d, J=8.1 Hz, 2H), 7.97 (d, J=8.1 Hz, 2H).

Intermediate 32.3. Methyl 4-(2-{(2R)-2-[(1E,3S)-3-hydroxy-oct-1-en-7-ynyl]-5-oxopyrrolidin-1-yl}ethyl)benzoate To a solution of (R)-2-methyl-CBS-oxazaborolidine (1.0 M in toluene, 0.49 mL, 0.49 mmol) in anhydrous THF at 0° C. was added Borane-THF complex (1.0 M, 0.49 mL, 0.49 mmol) dropwise. The mixture was stirred for 15 minutes. Intermediate 32.2 (180 mg, 0.51 mmol) in THF (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was used for the next step without purification.

EXAMPLE 32

4-[2-{(2R)-2-[(1E,3S)-3-hydroxy-oct-1-en-7-nyyl]-5-oxopyrrolidin-1-yl}ethyl)benzoic acid To a solution of Intermediate 32.3 in $MeOH/THF/H_2O$ (2/2/2 mL) was added NaOH (1.0 M, 1.23 mL, 1.23 mmol). The mixture was stirred for overnight. After concentration under reduced pressure, the residue was purified through RP-HPLC using ACN and $H_2O$/0.1% TFA to afford the desired product (168 mg) as a white solid. $^1HNMR$ ($CD_3OD$, ppm) δ 1.80 (t, J=7.0 Hz, 2H), 1.95 (s, 1H), 2.24 (dt, J=2.9 and 7.0 Hz, 2H), 2.36 (m, 2H), 3.13 (m, 1H), 3.51 (m, 1H), 3.70 (m, 1H), 3.88 (m, 1H), 5.35 (dd, J=8.6 and 15.4 Hz, 1H), 5.57 (dd, J=6.6 and 15.4 Hz, 1H), 7.21 (d, J=8.1 Hz, 2H), 7.89 (d, J=8.1 Hz, 2H), (m/z): 356.3 (M+H$^+$).

EXAMPLE 33

4-[2-{(2R)-2-[(1E,3S)-5,5-dimethyl-3-hydroxyhex-1-enyl]-5-oxo pyrrolidin-1-yl}ethyl)benzoic acid

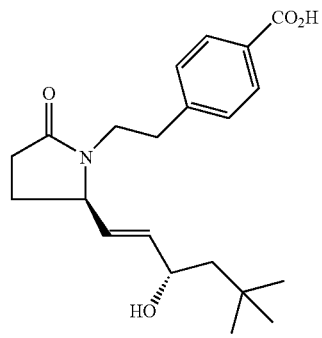

Intermediate 33.1. Methyl 4-(2-{(2R)-2-[(1E)-5,5-dimethyl-3-oxohex-1-enyl]-5-oxopyrrolidin-1-yl}ethyl)benzoate To a solution of Dimethyl 4,4-dimethyl-2-oxopentylphosphonate (201.8 mg, 0.908 mmol), prepared from ethyl tert-butylacetate and dimethyl methylphosphonate and n-butyllithium, in anhydrous THF (10 mL) at 0° C. was added 60% NaH (43.6 mg, 1.17 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over $MgSO_4$. The residue was purified through silica gel to afford the compound (220 mg) in 65% yield.

Intermediate 33.2. Methyl 4-(2-{(2R)-2-[(1E,3S)-5,5-dimethyl-3-hydroxyhex-1-enyl]-5-oxopyrrolidin-1-yl}ethyl)benzoate To a solution of (R)-2-methyl-CBS-oxazaborolidine (1.0 M in toluene, 0.59 mL, 0.59 mmol) in anhydrous THF at 0° C. was added Borane-THF complex (1.0 M, 0.59 mL, 0.59 mmol) dropwise. The mixture was stirred for 15 minutes. Intermediate 33.1 (220 mg, 0.59 mmol) in THE (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was used for the next step without purification.

EXAMPLE 33

4-[2-{(2R)-2-[(1E,3S)-5,5-dimethyl-3-hydroxyhex-1-enyl]-5-oxopyrrolidin-1-yl}ethyl)benzoic acid To a solution of Intermediate 33.2 in $MeOH/THF/H_2O$ (2/2/2 mL) was added NaOH (1.0 M, 1.48 mL, 1.48 mmol). The mixture was stirred for overnight. After concentration under reduced pressure, the residue was purified through RP-HPLC using ACN and H₂O/0.1% TFA to afford the desired product (155 mg) as a white solid. ¹HNMR (CD₃OD, ppm) δ 0.975 (s, 9H), 1.438 (m, 2H), 1.73 (m, 1H), 2.13 (m, 1H), 2.31 (m, 2H), 2.91 (m, 2H), 3.19 (m, 1H), 3.73 (m, 1H), 3.97 (m, 1H), 4.21 (m, 1H), 5.48 (dd, J=8.8 and 15.4 Hz, 1H), 5.71 (dd, J=6.2 and 15.4 Hz, 1H), 7.33 (d, J=8.4 Hz, 2H), 7.95 (d, J=8.4 Hz, 2H), (m/z): 360.1 (M+H⁺).

EXAMPLE 34

4-[2-{(2R)-2-[(1E,3S)-5-methyl-3-hydroxyhex-1-enyl]-5-oxopyrrolidin-1-yl}ethyl)benzoic acid

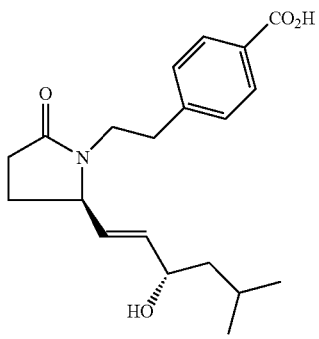

Intermediate 34.1. Methyl 4-(2-{(2R)-2-[(1E)-5-methyl-3-oxohex-1-enyl]-5-oxopyrrolidin-1-yl}ethyl)benzoate To a solution of Dimethyl 4-methyl-2-oxopentylphosphonate (189 mg, 0.908 mmol), prepared from ethyl isovalerate, dimethyl methylphosphonate and n-butyllithium, in anhydrous THF (10 mL) at 0° C. was added 60% NaH (43.6 mg, 1.17 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO₄. The residue was purified through silica gel to afford the compound (240 mg) in 74% yield.

Intermediate 34.2. Methyl 4-(2-{(2R)-2-[(1E,3S)-5-methyl-3-hydroxyhex-1-enyl]-5-oxopyrrolidin-1-yl}ethyl)benzoate To a solution of (R)-2-methyl-CBS-oxazaborolidine (1.0 M in toluene, 0.67 mL, 0.67 mmol) in anhydrous THF at 0° C. was added Borane-THF complex (1.0 M, 0.67 mL, 0.67 mmol) dropwise. The mixture was stirred for 15 minutes. Intermediate 34.1 (240 mg, 0.67 mmol) in THF (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was used for the next step without purification.

EXAMPLE 34

4-[2-{(2R)-2-[(1E,3S)-5-methyl-3-hydroxyhex-1-enyl]-5-oxopyrrolidin-1-yl}ethyl)benzoic acid To a solution of Intermediate 34.2 in MeOH/THF/H₂O (2/2/2 mL) was added NaOH (1.0 M, 1.68 mL, 1.68 mmol). The mixture was stirred for overnight. After concentration under reduced pressure, the residue was purified through RP-HPLC using ACN and H₂O/0.1% TFA to afford the desired product (155 mg) as a white solid. ¹HNMR (CD₃OD, ppm) δ 0.975 (d, J=3.5 Hz, 6H), 1.300 (m, 1H), 1.438 (m, 2H), 1.73 (m, 1H), 2.13 (m, 1H), 2.31 (m, 2H), 2.91 (m, 2H), 3.19 (m, 1H), 3.73 (m, 1H), 3.97 (m, 1H), 4.21 (m, 1H), 5.48 (dd, J=8.8 and 15.4 Hz, 1H), 5.71 (dd, J=6.2 and 15.4 Hz, 1H), 7.33 (d, J=8.4 Hz, 2H), 7.95 (d, J=8.4 Hz, 2H), (m/z): 346.1 (M+H⁺).

EXAMPLE 35

4-[2-{(2R)-2-[(1E,3S)-7-chloro-3-hydroxyhept-1-enyl]-5-oxopyrrolidin-1-yl}ethyl)benzoic acid

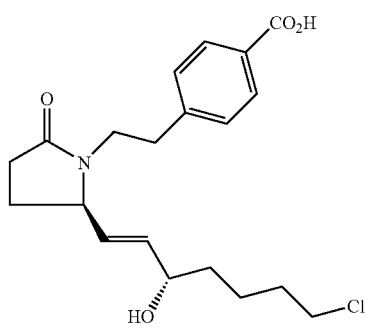

Intermediate 35.1. Dimethyl 6-chloro-2-oxohexylphosphonate

To a solution of dimethyl methylphosphonate (2.16 mL, 20 mmol) in anhydrous THF (30 mL), cooled at −78° C. was added n-BuLi (1.6 M in hexane, 13.75 mL, 22 mmol). The mixture was stirred for 30 minutes at this temperature under nitrogen. Methyl 5-chloropentanoate (1.50 g, 10 mmol) was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO₄. The residue was purified through flash chromatography on silica gel (MeOH:CH₂Cl₂=2:98) to give the product (1.60 g) with colorless oil in 17% yield. ¹HNMR (CDCl₃, ppm) δ 1.76 (m, 6H), 2.67 (t, J=6.6 Hz, 2H), 3.01 (d, J=21.7 Hz, 2H), 3.35 (t, J=6.2 Hz, 2H), 3.76 (s, 3H), 3.79 (s, 3H).

Intermediate 35.2. Methyl 4-(2-{(2R)-2-[(1E)-7-chloro-3-oxohept-1-enyl]-5-oxopyrrolidin-1-yl}ethyl)benzoate To a solution of Intermediate 35.1 (291 mg, 1.2 mmol) in anhydrous THF (15 mL) at 0° C. was added 60% NaH (52.8 mg, 1.32 mmol) in mineral oil. The mixture was stirred for 10 minutes. Intermediate 1.4 (330 mg, 1.2 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO₄. The residue was purified through silica gel to afford the compound (280 mg) in 73% yield. ¹HNMR (CDCl₃, ppm) δ 1.78 (br, 6H), 2.12 (m, 1H), 2.34 (m, 2H), 2.54 (m, 1H), 2.86 (m, 1H), 3.98 (m, 1H), 3.54 (t, J=6.2 Hz, 2H), 3.85 (m, 1H), 3.90 (s, 3H), 6.06 (d, J=15.7 Hz, 1H), 6.45 (dd, J=8.1 and 15.7 Hz, 1H), 7.25 (d, J=8.5 Hz, 2H), 7.97 (d, J=8.5 Hz, 2H).

Intermediate 35.3. Methyl 4-(2-{(2R)-2-[(1E 3S)-7-chloro-3-hydroxyhept-1-enyl]-5-oxopyrrolidin-1-yl}ethyl)benzoate To a solution of (R)-2-methyl-CBS-oxazaborolidine (1.0 M in toluene, 0.56 mL, 0.56 mmol) in anhydrous THF at 0° C. was added Borane-THF complex (1.0 M, 0.56 mL, 0.56 mmol) dropwise. The mixture was stirred for 15 minutes. Intermediate 35.2 (180 mg, 0.46 mmol) in THF (1 mL) was added dropwise. The mixture was stirred for 3 hours. The mixture was quenched with addition of 1 mL of the saturated ammonia chloride and was dilute with EtOAc (15 mL). The organic layer was washed with brine (3×5 mL), dried over MgSO4. The residue was used for the next step without purification.

EXAMPLE 35

4-[2-{(2R)-2-[(1E,3S)-7-chloro-3-hydroxyhept-1-enyl]-5-oxopyrrolidin-1-yl}ethyl)benzoic acid To a solution of Intermediate 35.3 in MeOH/THF/H$_2$O (2/2/2 mL) was added NaOH (1.0 M, 1.14 mL, 1.14 mmol). The mixture was stirred for overnight. After concentration under reduced pressure, the residue was purified through RP-HPLC using ACN and H$_2$O/0.1% TFA to afford the desired product (155 mg) as a white solid. $^1$HNMR (CD$_3$OD, ppm) δ 1.54 (br, 3H), 1.67 (m, 3H), 2.12 (m, 1H), 2.34 (m, 2H), 2.92 (m, 1H), 3.19 (m, 1H), 3.54 (t, J=6.2 Hz, 2H), 3.72 (m, 1H), 4.01 (m, 2H), 5.47 (dd, J=8.8 and 15.7 Hz, 1H), 5.65 (dd, J=6.2 and 15.7 Hz, 1H), 7.25 (d, J=8.4 Hz, 2H), 7.97 (d, J=8.4 Hz, 2H), (m/z): 380.1 (M+H$^+$).

EXAMPLE 36

4-[2-{(2R)-2-[(1E,3S)-3-hydroxy-oct-1-enyl]-5-oxopyrrolidin-1-yl}ethyl)benzamide

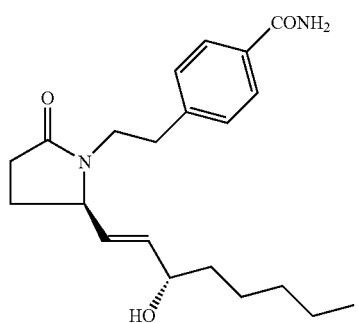

To a solution of 4-[2-{(2R)-2-[(1E,3S)-3-hydroxy-oct-1-enyl]-5-oxopyrrolidin-1-yl}ethyl)benzoic acid (71.90 mg, 0.2 mmol) in DMF (1 mL) was added EDC (57.51 mg, 0.3 mmol), HOBt (40.54 mg, 0.3 mmol), ammonia chloride (21.40 mg, 0.4 mmoL) and DIPEA. The mixture was stirred for overnight. After evaporation of the solvent, the residue was purified through RP-HPLC using ACN and H$_2$O/0.1% TFA to afford the desired product (70 mg) as a white solid. $^1$HNMR (CD$_3$OD, ppm) δ 0.879 (m, 3H), 2.297 (br, 6H), 1.49 (m, 2H), 1.75 (m, 1H), 2.19 (m, 1H), 2.34 (m, 2H), 2.89 (m, 2H), 3.17 (m, 1H), 3.73 (t, J=7.0 Hz, 1H), 4.04 (t, J=6.2 Hz, 2H), 5.45 (dd, J=8.8 and 15.1 Hz, 1H), 5.66 (dd, J=6.6 and 15.1 Hz, 1H), 7.30 (d, J=7.7 Hz, 2H), 7.82 (d, J=7.7 Hz, 2H), (m/z): 381.4 (+Na$^+$).

EXAMPLES 37 AND 38

4-[2-{(2S)-2-[3-(1-butylcyclobutyl)-3-hydroxypropyl]-5-oxopyrrolidin-1-yl}ethyl)benzoic acid

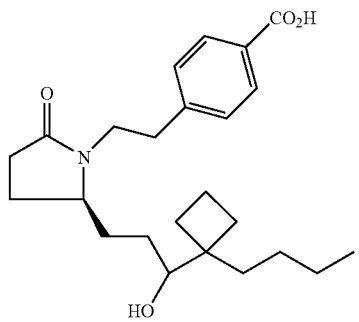

To a solution of methyl 4-[2-{(2R)-2-[(1E)-3-hydroxy-4-cyclobutyloct-1-enyl]-5-oxopyrrolidin-1-yl}ethyl)benzoate (0.85 g, 2.1 mmol) in methanol (20 mL) was added Pd/C (20 mg). The mixture was stirred under H$_2$ for overnight. The mixture was filtered through a pad of Celite. The Celite was washed with methanol. The crude product was dissolved in MeOH/THF/H$_2$O (6/6/6 mL) and added NaOH (1.0 M, 5.25 mL, 5.25 mmol). The mixture was stirred for overnight. The residue was purified through RP-HPLC using ACN and H$_2$O/ 0.1% TFA to afford Example 37 (232.33 mg) and Example 38 (90 mg) as a white solid.

EXAMPLE 37

4-[2-{(2S)-2-[(3S)-3-(1-butylcyclobutyl)-3-hydroxypropyl]-5-oxo pyrrolidin-1-yl}ethyl)benzoic acid (the first isomer from RP-HPLC (ACN/H$_2$O/TFA): $^1$HNMR (CD$_3$OD, ppm) δ 0.92 (m, 5H), 1.38 (br, 8H), 1.65 (br, 4H), 1.79 (m, 2H), 2.00 (m, 2H), 2.31 (m, 2H), 2.89-2.97 (m, 2H), 3.30 (m, 1H), 3.35 (m, 1H), 3.58 (m, 1H), 3.80 (m, 1H), 7.37 (d, J=8.1 Hz, 2H), 7.96 (d, J=8, 1 Hz, 2H). (m/z): 402.5 (M+H$^+$).

EXAMPLE 38

4-[2-{(2S)-2-[(3R)-3-(1-butylcyclobutyl)-3-hydroxypropyl]-5-oxo pyrrolidin-1-yl}ethyl)benzoic acid (the second isomer from RP-HPLC (ACN/H$_2$O/TFA): $^1$HNMR (CD$_3$OD, ppm) δ 0.92 (m, 5H), 1.38 (br, 8H), 1.65 (br, 4H), 1.79 (m, 2H), 2.00 (m, 2H), 2.31 (m, 2H), 2.89-2.97 (m, 2H), 3.30 (m, 1H), 3.35 (m, 1H), 3.58 (m, 1H), 3.80 (m, 1H), 7.37 (d, J=8.1 Hz, 2H), 7.96 (d, J=8,1 Hz, 2H). (m/z): 402.5 (M+H$^+$).

EXAMPLE 39

4-{2-[(2R)-2((1E,3S,7R)-3,7-dihydroxyoct-1-enyl)-5-oxopyrrolidin-1-yl]ethyl}benzoic acid

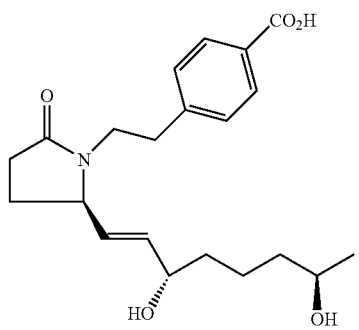

Intermediate 39.1. Ethyl (5R)-hydroxyhexanoate

To a solution of (S)-2-methyl-CBS-oxazaborolidine (1.0 M in toluene, 20 mL, 20 mmol) in anhydrous THF (50 mL) at 0° C. was added Borane-THF complex (1.0 M, 20 mL, 20 mmol) dropwise. The mixture was stirred for 15 minutes. Ethyl 5-oxohexanoate (3.20 mL, 20 mmol) in THF (4 mL) was added dropwise. The mixture was stirred for 3 hours. The mixture was quenched with addition of 1 mL of the saturated ammonia chloride and was dilute with EtOAc (50 mL). The organic layer was washed with brine (3×15 mL), dried over MgSO4. The residue was purified through flash chromatography on silica gel (EtOAc/Hexanes=1/4) to give the product (1.2 g) as colorless oil. $^1$HNMR (CD$_3$Cl, ppm) δ 1.18 (d, J=6.3 Hz, 3H), 1.25 (t, J=6.9 Hz, 3H), 1.48 (m, 2H), 1.60-1.80 (m, 2H), 2.33 (t, J=7.3 Hz, 2H), 3.78 (m, 1H), 4.15 (q, J=6.9 Hz, 2H).

Intermediate 39.2. Ethel (5R)-5-{[tert-butyl(dimethyl)silyl]oxy}hexanoate

To a solution of Intermediate 39.1 (1.1 g, 6.87 mmol), in anhydrous DMF (30 mL), was added TBSCl (1.55 g, 10.30 mmol) and imidazole (1.40 g, 20.6 mmol). The mixture was stirred for overnight. After evaporation of DMF under reduced pressure, the residue was purified through silica gel (EtOAc:Hexanes=1:4) to give 1.6 g of the colorless product in 85% yield. $^1$HNMR (CD$_3$Cl, ppm) δ 0.037 (s, 6H), 0.880 (s, 9H), 1.12 (d, J=6.2 Hz, 3H), 1.22 (t, J=7.0 Hz, 3H), 1.43 (m, 2H), 1.73 (m, 2H), 2.28 (t, J=7.3 Hz, 2H), 3.78 (tt, J=5.9 and 6.2 Hz, 1H), 4.15 (q, J=6.9 Hz, 2H), (m/z): 297.5 (M+Na$^+$).

Intermediate 39.3. Dimethyl (6R)-6-{[tert-butyl(dimethyl)silyl]oxy}-2-oxoheptyl phosphonate To a solution of dimethyl methylphosphonate (1.26 ml, 11.66 mmol) in anhydrous THF (20 mL), cooled at –78° C. was added n-BuLi (1.6 M in hexane, 8.0 mL, 12.87 mmol). The mixture was stirred for 30 minutes at this temperature under nitrogen. Ethyl (5R)-5-{[tert-butyl(dimethyl)silyl]oxy}hexanoate (1.60 g, 5.83 mmol) was added dropwise for 10 minutes. The mixture was stirred for 2 hours at –78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc:Hexanes=1:1) to give the product (1.25 g) with colorless oil in 59% yield. $^1$HNMR (CD$_3$OD, ppm) δ 0.013 (s, 6H), 0.874 (s, 9H), 1.07 (d, J=6.2 Hz, 3H), 1.22 (t, J=7.0 Hz, 3H), 1.43 (m, 2H), 1.73 (m, 2H), 2.59 (t, J=7.3 Hz, 2H), 3.08 (d, J=22.7 Hz, 2H), 3.74 (s, 3H), 3.77 (s, 3H).

Intermediate 39.4. Methyl 4-{2-[(2R)-2((1E,7R)-7-{[tert-butyl(dimethyl)silyl]oxy}-3-oxooct-1-enyl)-5-oxopyrrolidin-1-yl]ethyl}benzoate To a solution of intermediate 39.3 (399.5 mg, 1.09 mmol) in anhydrous THF (10 mL) at 0° C. was added 60% NaH (48 mg, 1.20 mmol) in mineral oil. The mixture was stirred for 10 minutes. Intermediate 1.4 (300 mg, 1.09 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$. The residue was purified through silica gel to afford the compound (410 mg) in 75% yield. $^1$HNMR (CD$_3$Cl, ppm) δ 0.015 (s, 6H), 0.853 (s, 9H), 1.11 (d, J=5.8 Hz, 3H), 1.38 (m, 2H), 1.50-1.80 (m, 4H), 2.12 (m, 1H), 2.40 (m, 2H), 2.50 (t, J=7.3 Hz, 2H), 2.84 (m, 1H), 2.89 (m, 1H), 3.06 (m, 1H), 6.02 (d, J=15.8 Hz, 1H), 6.43 (dd, J=8.1 and 15.8 Hz, 1H), 7.24 (d, J=8.4 Hz, 2H), 7.94 (d, J=8.4 Hz, 2H), (m/z): 524.6 (M+Na$^+$).

Intermediate 39.5. Methyl 4-{2-[(2R)-2((1E,3S,7R)-7-{[tert-butyl(dimethyl) silyl]oxy}-3-hydroxyoct-1-enyl)-5-oxopyrrolidin-1-yl]ethyl}benzoate To a solution of (R)-2-methyl-CBS-oxazaborolidine (1.0 M in toluene, 0.4 mL, 0.4 mmol) in anhydrous THF (10 mL) at 0° C. was added Borane-THF complex (1.0 M, 0.4 mL, 0.4 mmol) dropwise. The mixture was stirred for 15 minutes. Intermediate 39.4 (200 mg, 0.4 mmol) in THF (1 mL) was added dropwise. The mixture was stirred for 3 hours. The mixture was quenched with addition of 1 mL of the saturated ammonia chloride and was dilute with EtOAc (20 mL). The organic layer was washed with brine (3×5 mL), dried over MgSO4. The residue was used for the next reaction without purification.

Intermediate 39.6. Methyl 4-{2-[(2R)-2((1E,3S,7R)-3,7-dihydroxyoct-1-enyl)-5-oxopyrrolidin-1-yl]ethyl}benzoate To a solution of Intermediate 39.5 in THF (5 mL) was added TBAF (1.0 M, 1.0 mL). The mixture was stirred for overnight. The Residue was purified through silica gel (EtOAc:MeOH=95:5) to give the product (96 mg). (m/z): 412.2 (M+Na$^+$).

EXAMPLE 39

4-{2-[(2R)-2((1E,3S,7R)-3,7-dihydroxyoct-1-enyl)-5-oxopyrrolidin-1-yl]ethyl}benzoic acid Intermediate 39.6 (96 mg, 0.247 mmol) was dissolved in MeOH/THF/H$_2$O (1/1/1 mL) and added NaOH (1.0 M, 0.62 mL, 0.62 mmoL). The mixture was stirred for overnight. The residue was purified through RP-HPLC using ACN and H$_2$O/0.1% TFA to afford product (70 mg) as a white solid. $^1$HNMR (CD$_3$OD, ppm) δ 1.11 (d, J=6.2 Hz, 3H), 1.3-1.6 (m, 4H), 1.67 (m, 2H), 2.12 (m, 1H), 2.34 (m, 2H), 2.84 (m, 1H), 2.89 (m, 1H), 3.06 (m, 1H), 3.71 (m, 1H), 4.05 (m 2H), 5.48 (dd, J=8.8 and 15.4 Hz, 1H), 5.66 (dd, J=6.2 and 15.4 Hz, 1H), 7.33 (d, J=8.4 Hz, 2H), 7.96 (d, J=8.4 Hz, 2H), (m/z): 398.5 (M+Na$^+$).

EXAMPLE 40

4-{2-[(2R)-2((1E,3R,7R)-3,7-dihydroxyoct-1-enyl)-5-oxopyrrolidin-1-yl]ethyl}benzoic acid

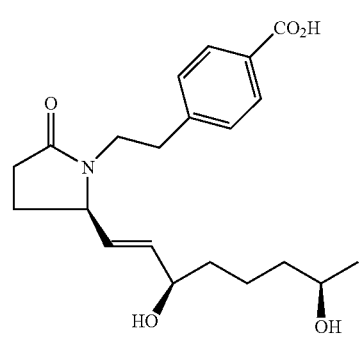

Intermediate 40.1. Methyl 4-{2-[(2R)-2((1E,3R,7R)-7-{[tert-butyl(dimethyl)silyl]oxy}-3-hydroxyoct-1-enyl)-5-oxopyrrolidin-1-yl]ethyl}benzoate To a solution of (S)-2-methyl-CBS-oxazaborolidine (1.0 M in toluene, 0.4 mL, 0.4 mmol) in anhydrous THF (10 mL) at 0° C. was added Borane-THF complex (1.0 M, 0.4 mL, 0.4 mmol) dropwise. The mixture was stirred for 15 minutes. Methyl 4-{2-[(2R)-2((1E,7R)-7-{[tert-butyl(dimethyl)silyl]oxy}-3-oxooct-1-enyl)-5-oxopyrrolidin-1-yl]ethyl}benzoate (200 mg, 0.4 mmol) in THF (1 mL) was added dropwise. The mixture was stirred for 3 hours. The mixture was quenched with addition of 1 mL of the saturated ammonia chloride and was dilute with EtOAc (20 mL). The organic layer was washed with brine (3×5 mL), dried over MgSO4. The residue was used for the next reaction without purification.

Intermediate 40.2. Methyl 4-{2-[(2-R)-2((1E,3R,7R)-3,7-dihydroxyoct-1-enyl)-5-oxopyrrolidin-1-yl]ethyl}benzoate To a solution of Intermediate 40.1 in THF (5 mL) was added TBFA (1.0 M, 1.0 mL). The mixture was stirred for overnight. The Residue was purified through silica gel (EtOAc:MeOH=95:5) to give the product (90 mg). (m/z): 412.4 (M+Na$^+$).

EXAMPLE 40

4-{2-[(2R)-2((1E,3R,7R)-3,7-dihydroxyoct-1-enyl)-5-oxopyrrolidin-1-yl]ethyl}benzoic acid Intermediate 40.2 (90 mg, 0.231 mmol) was dissolved in MeOH/THF/H$_2$O (1/1/1 mL) and added NaOH (1.0 M, 0.58 mL, 0.58 mmoL). The mixture was stirred for overnight. The residue was purified through RP-HPLC using ACN and H$_2$O/ 0.1% TFA to afford product (80 mg) as a white solid. $^1$HNMR (CD$_3$OD, ppm) δ 1.11 (d, J=6.2 Hz, 3H), 1.3-1.6 (m, 4H), 1.67 (m, 2H), 2.12 (m, 1H), 2.34 (m, 2H), 2.84 (m, 1H), 2.89 (m, 1H), 3.06 (m, 1H), 3.71 (m, 1H), 4.05 (m 2H), 5.48 (dd, J=8.8 and 15.4 Hz, 1H), 5.66 (dd, J=6.2 and 15.4 Hz, 1H), 7.33 (d, J=8.4 Hz, 2H), 7.96 (d, J=8.4 Hz, 2H), (m/z): 398.5 (M+Na$^+$).

EXAMPLES 41 AND 42

4-{2-[(2R)-2((1E,7S)-3,7-dihydroxyoct-1-enyl)-5-oxo Pyrrolidin-1-yl]ethyl}benzoic acid

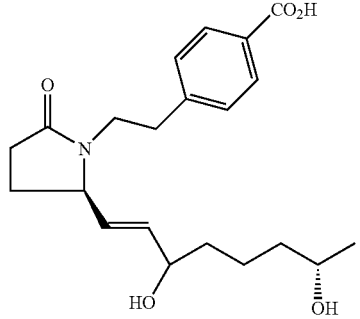

Intermediate 41.1. Ethyl (5S)-hydroxyhexanoate

To a solution of (R)-2-methyl-CBS-oxazaborolidine (1.0 M in toluene, 20 mL, 20 mmol) in anhydrous THF (50 mL) at 0° C. was added Borane-THF complex (1.0 M, 20 mL, 20 mmol) dropwise. The mixture was stirred for 15 minutes. Ethyl 5-oxohexanoate (3.20 mL, 20 mmol) in THF (4 mL) was added dropwise. The mixture was stirred for 3 hours. The mixture was quenched with addition of 1 mL of the saturated ammonia chloride and was dilute with EtOAc (50 mL). The organic layer was washed with brine (3×15 mL), dried over MgSO4. The residue was purified through flash chromatography on silica gel (EtOAc/Hexanes=1/4) to give the product (2.4 g) as colorless oil in 75% yield. $^1$HNMR (CD$_3$Cl, ppm) δ 1.18 (d, J=6.3 Hz, 3H), 1.25 (t, J=6.9 Hz, 3H), 1.48 (m, 2H), 1.60-1.80 (m, 2H), 2.33 (t, J=7.3 Hz, 2H), 3.78 (m, 1H), 4.15 (q, J=6.9 Hz, 2H).

Intermediate 41.2. Ethyl (5S)-5-{[tert-butyl(dimethyl silyl]oxy}hexanoate

To a solution of Intermediate 41.1 (1.0 g, 6.24 mmol), in anhydrous DMF (30 mL), was added TBSCl (1.41 g, 9.36 mmol) and imidazole (1.27 g, 18.72 mmol). The mixture was stirred for overnight. After evaporation of DMF under reduced pressure, the residue was purified through silica gel (EtOAc:Hexanes=1:4) to give 1.42 g of the colorless product in 80% yield. $^1$HNMR (CD$_3$Cl, ppm) δ 0.037 (s, 6H), 0.880 (s, 9H), 1.12 (d, J=6.2 Hz, 3H), 1.22 (t, J=7.0 Hz, 3H), 1.43 (m, 2H), 1.73 (m, 2H), 2.28 (t, J=7.3 Hz, 2H), 3.78 (tt, J=5.9 and 6.2 Hz, 1H), 4.15 (q, J=6.9 Hz, 2H).

Intermediate 41.3. Dimethyl (6S)-6-{[tert-butyl(dimethyl)silyl]oxy}-2-oxoheptyl phosphonate To a solution of dimethyl methylphosphonate (1.11 ml, 10.2 mmol) in anhydrous THF (20 mL), cooled at –78° C. was added n-BuLi (1.6 M in hexane, 7.0 mL, 11.22 mmol). The mixture was stirred for 30 minutes at this temperature under nitrogen. Ethyl (5S)-5-{[tert-butyl(dimethyl)silyl]oxy}hexanoate (1.40 g, 5.1 mmol) was added dropwise for 10 minutes. The mixture was stirred for 2 hours at –78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc:Hexanes=1:1) to give the product (1.60 g) with colorless oil in 85% yield. $^1$HNMR (CD$_3$Cl, ppm) δ 0.013 (s, 6H), 0.874 (s, 9H), 1.07 (d, J=6.2 Hz, 3H), 1.22 (t, J=7.0 Hz, 3H), 1.43 (m, 2H), 1.73 (m, 2H), 2.59 (t, J=7.3 Hz, 2H), 3.08 (d, J=22.7 Hz, 2H), 3.74 (s, 3H), 3.77 (s, 3H).

Intermediate 41.4. Methyl 4-{2-[(2R)-2((1E,7S)-7-{[tert-butyl(dimethyl) silyl]oxy}-3-oxooct-1-enyl)-5-oxopyrrolidin-1-yl]ethyl}benzoate To a solution of intermediate 41.3 (322.83 mg, 0.908 mmol) in anhydrous THF (10 mL) at 0° C. was added 60% NaH (40 mg, 1.0 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$. The residue was purified through silica gel to afford the compound (330 mg) in 72% yield. $^1$HNMR (CD$_3$Cl, ppm) δ 0.015 (s, 6H), 0.853 (s, 9H), 1.11 (d, J=5.8 Hz, 3H), 1.38 (m, 2H), 1.50-1.80 (m, 4H), 2.12 (m, 1H), 2.40 (m, 2H), 2.50 (t, J=7.3 Hz, 2H), 2.84 (m, 1H), 2.89 (m, 1H), 3.06 (m, 1H), 6.02 (d, J=15.8 Hz, 1H), 6.43 (dd, J=8.1 and 15.8 Hz, 1H), 7.24 (d, J=8.4 Hz, 2H), 7.94 (d, J=8.4 Hz, 2H), (m/z): 524.6 (M+Na$^+$).

Intermediate 41.5. Methyl 4-{2-[(2R)-2((1E,7S)-7-{[tert-butyl(dimethyl) silyl]oxy}-3-hydroxyoct-1-enyl)-5-oxopyrrolidin-1-yl]ethyl]benzoate To a solution of (S)-2-methyl-CBS-oxazaborolidine (1.0 M in toluene, 0.66 mL, 0.66 mmol) in anhydrous THF (10 mL) at 0° C. was added Borane-THF complex (1.0 M, 0.66 mL, 0.66 mmol) dropwise. The mixture was stirred for 15 minutes. Intermediate 41.4 (200 mg, 0.4 mmol) in THF (1 mL) was added dropwise. The mixture was stirred for 3 hours. The mixture was quenched with addition of 1 mL of the saturated ammonia chloride and was dilute with EtOAc (20 mL). The organic layer was washed with brine (3×5 mL), dried over MgSO4. The residue was used for the next reaction without purification.

Intermediate 41.6. Methyl 4-{2-[(2R)-2((1E,7S)-3,7-dihydroxyoct-1-enyl)-5-oxopyrrolidin-1-yl]ethyl}benzoate To a solution of Intermediate 41.5 in THF (5 mL) was added TBAF (1.0 M, 1.0 mL). The mixture was stirred for overnight. The Residue was purified through silica gel (EtOAc:MeOH=95:5) to give the product (140 mg). (m/z): 412.2 (M+Na$^+$).

EXAMPLES 41 AND 42

4-{2-[(2R)-2((1E,7S)-3,7-dihydroxyoct-1-enyl)-5-oxo pyrrolidin-1-yl]ethyl}benzoic acid Intermediate 41.6 (96 mg, 0.247 mmol) was dissolved in MeOH/THF/H$_2$O (1/1/1 mL) and added NaOH (1.0 M, 0.62 mL, 0.62 mmoL). The mixture was stirred for overnight. The residue was purified through RP-HPLC using ACN and H$_2$O/0.1% TFA to afford Example 41 (130 mg) and example 42 (32 mg) as a white solid.

EXAMPLE 41

4-{2-[(2R)-2((1E,3S,7S)-3,7-dihydroxyoct-1-enyl)-5-oxopyrrolidin-1-yl]ethyl} benzoic acid (the first isomer from RP-HPLC (ACN/H$_2$O/TFA): $^1$HNMR (CD$_3$OD, ppm) δ 1.11 (d, J=6.2 Hz, 3H), 1.3-1.6 (m, 4H), 1.67 (m, 2H), 2.12 (m, 1H), 2.34 (m, 2H), 2.84 (m, 1H), 2.89 (m, 1H), 3.06 (m, 1H), 3.71 (m, 1H), 4.05 (m 2H), 5.48 (dd, J=8.8 and 15.4 Hz, 1H), 5.66 (dd, J=6.2 and 15.4 Hz, 1H), 7.33 (d, J=8.4 Hz, 2H), 7.96 (d, J=8.4 Hz, 2H), (m/z): 375.8(M$^+$).

EXAMPLE 42

4-{2-[(2R)-2((1E,3R,7S)-3,7-dihydroxyoct-1-enyl)-5-oxopyrrolidin-1-yl]ethyl} benzoic acid (the second isomer from RP-HPLC (ACN/H$_2$O/TFA): $^1$HNMR (CD$_3$OD, ppm) δ 1.13 (d, J=6.2 Hz, 3H), 1.34-1.63 (m, 5H), 1.69 (m, 2H), 2.17 (m, 1H), 2.32 (m, 2H), 2.80 (m, 1H), 2.86 (m, 1H), 3.06 (m, 1H), 3.68 (m, 2H), 3.71 (m, 1H), 4.05 (m 1H), 5.41 (dd, J=8.8 and 15.4 Hz, 1H), 5.59 (dd, J=6.2 and 15.4 Hz, 1H), 7.23 (d, J=8.4 Hz, 2H), 7.88 (d, J=8.4 Hz, 2H), (m/z): 398.5(M+Na$^+$).

EXAMPLE 43

4-(2-{(2R)-3-(3R)-3-hydroxy-4-methyl-4-phenylpentyl]-5-oxo pyrrolidin-1-yl}ethyl)benzoic acid

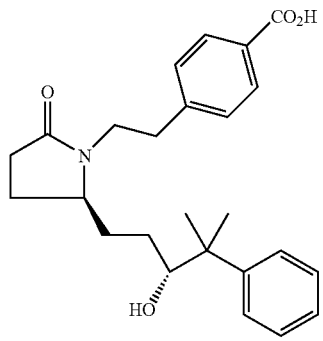

Intermediate 43.1. Methyl 4-(2-{(2R)-3-hydroxy-4-methyl-4-phenylpentyl]-5-oxopyrrolidin-1-yl}ethyl)benzoate To a solution of methyl 4-[2-((2R)-2-{(1E)-3-hydroxy-4-methyl-4-phenylpent-1-enyl}-5-oxopyrrolidin-1-yl)ethyl]benzoate (200 mg, 0.474 mmol) in methanol (20 mL) was added Pd/C (20 mg). The mixture was exposure to hydrogen (with balloon) for overnight. The Pd/C was filtered through a layer of Celite. After evaporation of the solvent, the crude product was used for the next reaction without further purification.

EXAMPLE 43

4-(2-{(2R)-3-(3R)-hydroxy-4-methyl-4-phenylpentyl]-5-oxopyrrolidin-1-yl}ethyl)benzoic acid Intermediate 43.1 (0.474 mmol) was dissolved in MeOH/THF/H$_2$O (2/2/2 mL) and added NaOH (1.0 M, 0.1.20 mL, 1.20 mmoL). The mixture was stirred for overnight. The residue was purified through RP-HPLC using ACN and H$_2$O/0.1% TFA to afford Example 43 (88 mg) as a white solid. $^1$HNMR (CD$_3$OD, ppm) δ 1.314 (s, 3H), 1.340 (s, 2H), 1.568 (m, 1H), 1.98 (m, 2H), 2.08 (m, 3H), 2.37 (m, 2H), 2.68 (m, 2H), 3.55 (m, 1H), 3.73 (m, 1H), 4.24 (m, 1H), 7.16 (d, J=8.0 Hz, 1H), 7.23 (m, 4H), 7.37 (d, J=8.0 Hz, 2H), 7.93 (d, J=8.0 Hz, 2H), MS (m/z) 410.6 (M+H$^+$), 432.3 (M+Na$^+$).

EXAMPLES 45 AND 46

Synthesis of: 4-(2-{(2R)-2-[(1E)-3-(1-butylcyclobutyl)-3-hydroxyprop-1-enyl]-5-oxopyrrolidin-1-yl}ethyl)benzoic acid

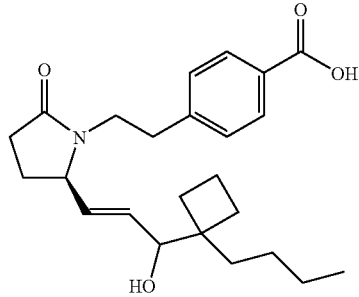

Intermediate 45.1: 1-butylcyclobutanecarboxylic acid

To a solution of LDA (30 mL, 2.0M, 60 mmol) in THF/heptane/ethylbenzene and anhydrous THF (30 mL) at 0° C. was added cyclobutane carboxylic acid (3.0 g, 30 mmol) dropwise. After addition was complete, the cold bath was removed, the reaction mixture was stirred at room temperature for 2 hr. Neat n-BuI (3.41 mL, 30 mmol) was added dropwise at room temperature. The mixture was stirred over night. To the mixture was added 2N HCl and the mixture was extracted with ethyl acetate. The combined organic phase was washed with water and brine to afford the title compound as a light yellow oil (quantitative), which was used in the next step without purification.

Intermediate 45.2: methyl 1-butylcyclobutanecarboxylate

To a solution of 1-butylcyclobutanecarboxylic acid (4.69 g, 30 mmol) in dry dichloromethane (70 mL) and dry MeOH (17 mL) was added trimethylsiyldiazomethane (16.50, 2.0 M, 33 mmol) in hexane dropwise under Ar at room temperature. TLC showed completion of the reaction (Rf=0.58, 1:10 ethyl acetate/hexanes). After concentration, the product (3.07 g, 60% 2 steps) was obtained by flash column chromatography through silica gel (hexanes).

Intermediate 45.3: dimethyl 2-(1-butylcyclobutyl)-2-oxoethylphosphonate

To a solution of dimethyl methylphosphonate (1.46 g, 11.8 mmol) in anhydrous THF (25 mL) at −78° C. was added n-BuLi (7.4 mL, 1.6 M, 11.8 mmol) dropwise under Ar. The reaction was stirred for 15 minutes. A solution of methyl 1-butylcyclobutanecarboxylate (1.00 g, 5.87 mmol) in THF (5 mL) was added dropwise. The reaction mixture was stirred for 30 minutes at −78° C., after which it was allowed to warn to room temperature. The reaction was quenched with 5% HCl, extracted with $CH_2Cl_2$ (3×30 mL), the combined organic phase was washed with brine, dried ($MgSO_4$). After concentration, flash chromatography (silica gel, 1:1 ethylacetate:hexanes), the title compound was obtained as a colorless oil. $^1$HNMR ($CDCl_3$) δ 0.85~0.89 (m, 3H), 1.05~1.15 (m, 2H), 1.22~1.35 (m, 2H), 1.65~1.95 (m, 6H), 2.35~2.50 (m, 2H), 3.00 (s, 1H0, 3.06 (s, 1H), 3.78 (s, 3H), 3.82 (s, 3H). MS (m/z) 285 (M+Na)

Intermediate 45.4: methyl 4-(2-{(2R)-2-[(1E)-3-(1-butylcyclobutyl)-3-oxoprop-1-enyl]-5-oxopyrrolidin-1-yl}ethyl)benzoate This intermediate was synthesized using procedure of Intermediate 1.4 from intermediate 1.3 and intermediate 45.3. The crude product was used for next step without purification.

Intermediate 45.5: methyl 4-(2-{(2R)-2-[(1E)-3-(1-butylcyclobutyl)-3-hydroxy-prop-1-enyl]-5-oxopyrrolidin-1-yl}ethyl)benzoate This intermediate was synthesized using the procedure of Intermediate 1.5 from intermediate 45.4. MS (m/z) 436 (M+Na). The crude mixture product was used for next step without purification.

EXAMPLES 45 AND 46

4-(2-{(2R)-2-[(1E)-3-(1-butylcyclobutyl)-3-hydroxyprop-1-enyl]-5-oxopyrrolidin-1-yl}ethyl)benzoic acid This intermediate was synthesized using the procedure of Example 1 and 2 from intermediate 45.5.

EXAMPLE 45

4-(2-{(2R)-2-[(1E,3R)-3-(1-butylcyclobutyl)-3-hydroxyprop-1-enyl]-5-oxopyrrolidin-1-yl}ethyl)benzoic acid: $^1$H NMR ($CD_3OD$) δ 0.85~0.95 (m, 3H), 1.18~1.40 (m, 6H), 1.45~1.90 (m, 6H), 1.98~2.42 (m, 4H), 2.78~2.95 (m, 2H), 3.05~3.15 (m, 1H), 3.70~3.82 (m, 1H), 3.90~4.05 (m, 2H), 5.50 (dd, J=8.1, 15 Hz, 1H), 5.68 (dd, J=6.9, 15 Hz, 1H), 7.31 (d, J=8.0 Hz, 2H), 7.94 (d, J=8.0 Hz, 2H). MS (m/z) 400.1 (M+H).

EXAMPLE 46

4-(2-{(2R)-2-[(1E,3S)-3-(1-butylcyclobutyl)-3-hydroxyprop-1-enyl]-5-oxopyrrolidin-1-yl}ethyl)benzoic acid: $^1$H NMR ($CD_3OD$) δ 0.85~0.95 (m, 3H), 1.18~1.40 (m, 6H), 1.45~1.90 (m, 6H), 1.98~2.42 (m, 4H), 2.78~2.95 (m, 2H), 3.05~3.15 (m, 1H), 3.70~3.82 (m, 1H), 3.90~4.10 (m, 2H), 5.47 (ddd, J=1.1, 8.8, 15 Hz, 1H), 5.74 (dd, J=6.2, 15 Hz, 1H), 7.31 (d, J=8.2 Hz, 2H), 7.94 (d, J=8.2 Hz, 2H). MS (m/z) 400.2 (M+H).

EXAMPLES 47 AND 48

Synthesis of 4-(2-{(2R)-2-[(1E)-3-hydroxy-3-(1-propyl cyclobutyl)prop-1-enyl]-5-oxopyrrolidin-1-yl}ethyl)benzoic acid

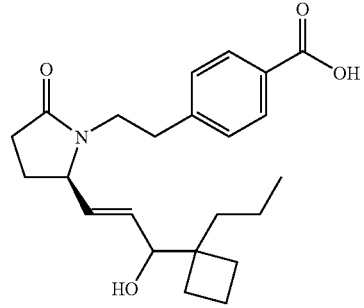

The title compound was prepared using the procedure of Example 45 and 46 from cyclobutane carboxylic acid and n-propyl ioide.

EXAMPLE 47

4-(2-{(2R)-2-[(1E,3R)-3-hydroxy-3-(1-propylcyclobutyl)prop-1-enyl]-5-oxopyrrolidin-1-yl}ethyl)benzoic acid: $^1$H NMR ($CD_3OD$) δ 0.80~0.95 (m, 3H), 1.28~1.90 (m, 10H), 1.98~2.42 (m, 4H), 2.78~2.95 (m, 2H), 3.05~3.20 (m, 1H), 3.75~3.85 (m, 1H), 3.90~4.05 (m, 2H), 5.50 (dd, J=8.1, 15 Hz, 1H), 5.68 (dd, J=6.9, 15 Hz, 1H), 7.31 (d, J=8.1 Hz, 2H), 7.94 (d, J=8.1 Hz, 2H). MS (m/z) 386.5 (M+H).

EXAMPLE 48

4-(2-{(2R)-2-[(1E,3S)-3-hydroxy-3-(1-propylcyclobutyl)prop-1-enyl]-5-oxopyrrolidin-1-yl}ethyl)benzoic acid: $^1$H NMR ($CD_3OD$) δ 0.80~0.95 (m, 3H), 1.28~1.90 (m, 10H), 1.98~2.42 (m, 4H), 2.78~2.95 (m, 2H), 3.05~3.20 (m, 1H), 3.75~3.85 (m, 1H), 3.90~4.05 (m, 2H), 5.50 (dd, J=8.1, 15 Hz, 1H), 5.68 (dd, J=6.9, 15 Hz, 1H), 7.31 (d, J=8.1 Hz, 2H), 7.94 (d, J=8.1 Hz, 2H). MS (m/z) 386.5 (M+H).

EXAMPLE 49

Synthesis of 4-(2-{(2R)-2-[(1E,3R)-3-(1-benzylcyclobutyl)-3-hydroxyprop-1-enyl]-5-oxopyrrolidin-1-yl}ethyl)benzoic acid

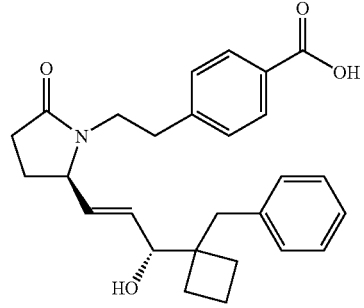

The title compound was prepared using the procedure of Example 45, and Example 9 from cyclobutane carboxylic acid and benzyl bromide. $^1$HNMR ($CD_3OD$) δ 1.35~2.45 (m, 10H), 2.60 (d, J=14 Hz, 1H), 2.78~2.95 (m, 3H), 3.10~3.20 (m, 1H), 3.70~3.80 (m, 1H), 3.95~4.10 (m, 2H), 5.51 (ddd, J=1.1, 8.8, 15 Hz, 1H), 5.82 (dd, J=6.6, 15 Hz, 1H), 7.15~7.35 (m, 7H), 7.94 (d, J=8.1 Hz, 2H). MS (m/z) 434.1 (M+H).

EXAMPLES 50 AND 51

Synthesis of 4-[2-((2R)-2-{(1E)-3-hydroxy-3-[1-(2-phenylethyl)cyclobutyl]prop-1-enyl}-5-oxopyrrolidin-1-yl)ethyl]benzoic acid

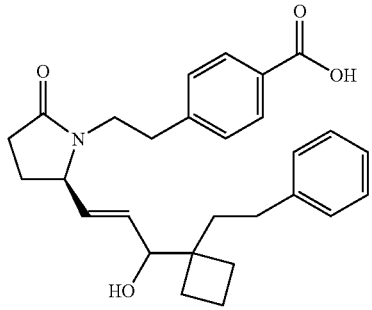

The title compound was prepared using the procedure of Example 45 and 46 from cyclobutane carboxylic acid and (2-bromoethyl)benzene.

EXAMPLE 50

4-[2-((2R)-2-{(1E,3R)-3-hydroxy-3-[1-(2-phenylethyl)cyclobutyl]prop-1-enyl}-5-oxopyrrolidin-1-yl)ethyl]benzoic acid: $^1$H NMR (CD$_3$OD) δ 1.50~2.50 (m, 12H), 2.55~2.95 (m, 4H), 3.05~3.20 (m, 1H), 3.75~3.85 (m, 1H), 3.90~4.10 (m, 2H), 5.50~5.60 (m, 1H), 5.70 (dd, J=6.9, 15 Hz, 1H), 7.00~7.30 (m, 7H), 7.90 (d, J=8.4 Hz, 2H). MS (m/z) 448.2 (M+H).

EXAMPLE 51

4-[2-((2R)-2-{(1E,3S)-3-hydroxy-3-[1-(2-phenylethyl)cyclobutyl]prop-1-enyl}-5-oxopyrrolidin-1-yl)ethyl]benzoic acid: $^1$H NMR (CD$_3$OD) δ 1.50~2.50 (m, 12H), 2.55~2.95 (m, 4H), 3.05~3.20 (m, 1H), 3.75~3.85 (m, 1H), 3.90~4.10 (m, 2H), 5.50~5.60 (m, 1H), 5.78 (dd, J=6.2, 15 Hz, 1H), 7.00~7.40 (m, 7H), 7.91 (d, J=8.1 Hz, 2H). MS (m/z) 448.2 (M+H).

EXAMPLE 52

Synthesis of 4-(2-{(2R)-2-[(1E,3S)-3-hydroxy-5-phenylpent-1-enyl]-5-oxopyrrolidin-1-yl}ethyl)benzoic acid

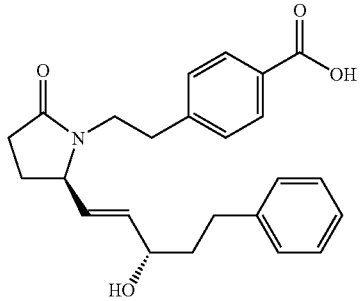

The title compound was prepared using the procedure of Example 9 from intermediate 1.4 and methyl 3-phenylpropionate. $^1$H NMR (CD$_3$OD) δ 1.70~1.85 (m, 2H), 2.15~2.45 (m, 3H), 2.60~2.95 (m, 4H), 3.10~3.25 (m, 1H), 3.65~3.75 (m, 1H), 4.00~4.10 (m, 2H), 5.36~5.50 (m, 1H), 5.71 (dd, J=6.3, 15 Hz, 1H), 7.10~7.36 (m, 7H), 7.90 (d, J=8.1 Hz, 2H). MS (m/z) 394.4 (M+H).

EXAMPLE 53

Synthesis of 4-(2-{(2R)-2-[(1E,3S)-3-hydroxy-4-(3-methylphenyl)but-1-enyl]-5-oxopyrrolidin-1-yl}ethyl)benzoic acid

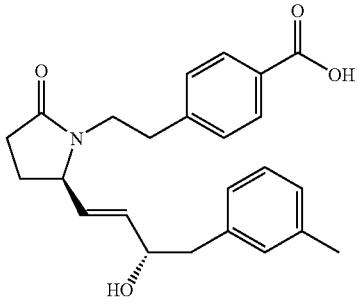

Example 53 was prepared using the procedure of Example 9 from ethyl m-tolylacetate. $^1$H NMR (CD$_3$OD) δ 1.55~1.68 (m, 1H), 2.10~2.40 (m, 4H), 2.27 (s, 3H), 2.70~2.90 (m, 3H), 2.95~3.15 (m, 2H), 3.55~3.65 (m, 1H), 3.90~4.00 (m, 1H), 5.48 (dd, J=8.8, 15 Hz, 1H), 5.58~5.76 (m, 1H), 7.00~7.16 (m, 4H), 7.24 (d, J=8.4 Hz, 2H), 7.94 (d, J=8.4 Hz, 2H). MS (m/z) 394.4 (M+H).

EXAMPLE 54

Synthesis of 4-(2-{(2S)-2-[(3R)-3-hydroxy-4-(3-methylphenyl)butyl]-5-oxopyrrolidin-1-yl}ethyl)benzoic acid

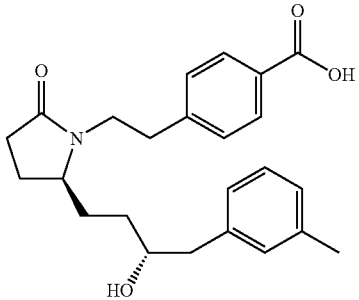

Example 54 was prepared using the procedure of Example 53 from ethyl m-tolylacetate. $^1$HNMR (CD$_3$OD) δ 1.20~1.80 (m, 5H), 1.90~2.10 (m, 1H), 2.15~2.30 (m, 2H), 2.28 (s, 3H), 2.60~3.00 (m, 4H), 3.15~3.25 (m, 1H), 3.545~3.55 (m, 1H), 3.75~3.85 (m, 2H), 6.90~7.16 (m, 4H), 7.32 (d, J=8.1 Hz, 2H), 7.93 (d, J=8.1 Hz, 2H). MS (m/z) 396.1 (M+H).

EXAMPLE 55

Synthesis of 4-(2-{(2R)-2-[(1E,3S)-3-hydroxy-5-phenylpent-1-enyl]-5-oxopyrrolidin-1-yl}ethyl)benzoic acid

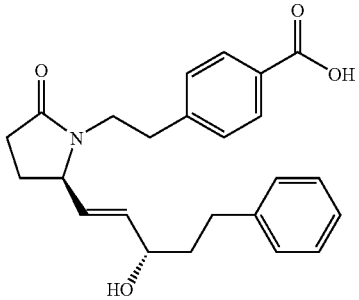

The title compound was prepared using the procedure of Example 9 from intermediate 1.4 and methyl 3-phenylpropionate. $^1$H NMR (CD$_3$OD) δ 1.70~1.85 (m, 2H), 2.15~2.45 (m, 3H), 2.60~2.95 (m, 4H), 3.10~3.25 (m, 1H), 3.65~3.75 (m, 1H), 4.00~4.10 (m, 2H), 5.36~5.50 (m, 1H), 5.71 (dd, J=6.3, 15 Hz, 1H), 7.10~7.36 (m, 7H), 7.90 (d, J=8.1 Hz, 2H). MS (m/z) 394.4 (M+H).

EXAMPLES 56 AND 57

Synthesis of 4-[2-((2R)-2-{(1E)-3-[1-(4-chlorophenyl) cyclopropyl]-3-hydroxyprop-1-enyl}-5-oxopyrrolidin-1-yl)ethyl]benzoic acid

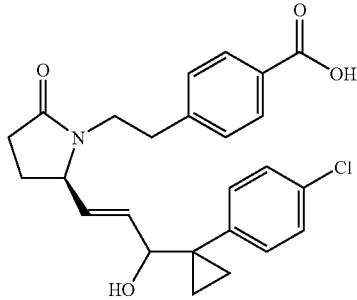

Example 56 and 57 were prepared using the procedure of Example 45 and 46 from 1-(4-chlorophenyl)cyclopropanecarboxylic acid.

EXAMPLE 56

4-[2-((2R)-2-{(1E,3R)-3-[1-(4-chlorophenyl)cyclopropyl]-3-hydroxyprop-1-enyl}-5-oxopyrrolidin-1-yl)ethyl] benzoic acid: $^1$H NMR (CD$_3$OD) δ 0.70~1.00 (m, 4H), 1.55~1.65 (m, 1H), 2.00~2.40 (m, 3H), 2.50~3.00 (m, 3H), 3.50~3.90 (m, 3H), 5.26~5.38 (m, 1H), 5.55 (dd, J=6.6, 15 Hz, 1H), 7.10~7.60 (m, 6H), 7.95 (d, J=8.0 Hz, 2H). MS (m/z) 440.0 M+H).

EXAMPLE 57

4-[2-((2R)-2-{(1E,3S)-3-[1-(4-chlorophenyl)cyclopropyl]-3-hydroxyprop-1-enyl}-5-oxopyrrolidin-1-yl)ethyl] benzoic acid: $^1$H NMR (CD$_3$OD) δ 0.70~1.00 (m, 4H), 1.55~1.65 (m, 1H), 2.00~2.40 (m, 3H), 2.50~3.00 (m, 3H), 3.50~3.90 (m, 3H), 5.26 (dd, J=8.7, 15 Hz, 1H), 5.63 (dd, J=6, 15 Hz, 1H), 7.10~7.60 (m, 6H), 7.95 (d, J=8.1 Hz, 2H). MS (m/z) 440.0 (M+H).

EXAMPLES 58 AND 59

Synthesis of 4-(2-{(2R)-2-[(1E)-4-(4-chlorophenyl)-3-hydroxy-4-methylpent-1-enyl]-5-oxopyrrolidin-1-yl}ethyl)benzoic acid

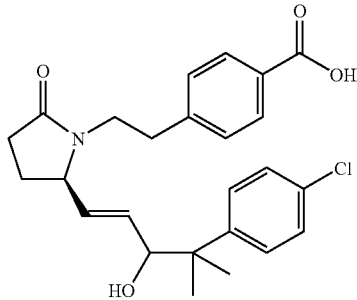

Example 58 and 59 were prepared using the procedure of example 45 and 46 from 2-(4-chlorophenyl)-2-methylpropanoic acid.

EXAMPLE 58

4-(2-{(2R)-2-[(1E,3R)-4-(4-chlorophenyl)-3-hydroxy-4-methylpent-1-enyl]-5-oxopyrrolidin-1-yl}ethyl)benzoic acid: $^1$H NMR (CD$_3$OD) δ 1.30 (s, 3H), 1.32 (s, H), 1.50~1.65 (m, 1H), 1.95~2.35 (m, 3H), 2.70~3.05 (m, 3H), 3.55~3.70 (m, 1H), 3.75~3.85 (m, 1H), 4.15~4.25 (m, 1H), 5.20~5.30 (m, 1H), 5.42 (dd, J=7.0, 15 Hz, 1H), 7.10~7.45 (m, 6H), 7.95 (d, J=8.0 Hz, 2H). MS (m/z) 442.1 (M+H).

EXAMPLE 59

4-(2-{(2R)-2-[(1E,3S)-4-(4-chlorophenyl)-3-hydroxy-4-methylpent-1-enyl]-5-oxopyrrolidin-1-yl}ethyl)benzoic acid: $^1$H NMR (CD$_3$OD) δ 1.30 (s, 3H), 1.32 (s, H), 1.50~1.65 (m, 1H), 2.00~2.35 (m, 3H), 2.60~2.85 (m, 3H), 3.55~3.60 (m, 1H), 3.75~3.85 (m, 1H), 4.15~4.25 (m, 1H), 5.20~5.30 (m, 1H), 5.42 (dd, J=6.3, 15 Hz, 1H), 7.10~7.45 (m, 6H), 7.95 (d, J=8.4 Hz, 2H). MS (m/z) 442.1 (M+H).

EXAMPLES 60 AND 61

Synthesis of 4-(2-{(2R)-2-[(1E)-4-cyclopropyl-3-hydroxybut-1-enyl]-5-oxopyrrolidin-1-yl}ethyl)benzoic acid

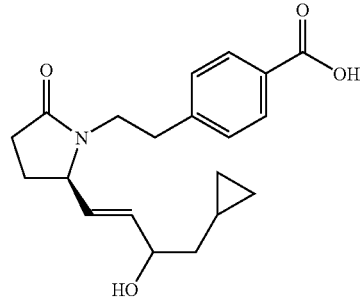

Example 60 and 61 were prepared using the procedure of Example 45 and 46 starting from cyclopropylacetic acid.

EXAMPLE 60

4-(2-{(2R)-2-[(1E,3S)-4-cyclopropyl-3-hydroxybut-1-enyl]-5-oxo pyrrolidin-1-yl}ethyl)benzoic acid: $^1$H NMR (CD$_3$OD) δ 0.05~0.15 (m, 2H), 0.35~0.50 (m, 2H), 0.70~0.82 (m, 1H), 1.30~1.40 (m, 1H), 1.41~1.55 (m, 1H), 1.65~1.80 (m 1H), 2.10~2.20 (m, 1H), 2.22~2.40 (m, 2H), 2.75~2.95 (m, 2H), 3.10~3.20 (m, 1H), 3.65~3.75 (m, 1H), 3.88~4.00 (m, 1H), 4.10~4.20 (m, 1H), 5.47 (ddd, J=1.1, 8.8, 15 Hz, 1H), 5.68 (dd, J=6.2, 15 Hz, 1H), 7.21 (d, J=8.4 Hz, 2H), 7.88 (d, J=8.4 Hz, 2H). MS (m/z) 344.0 (M+H).

EXAMPLE 61

4-(2-{(2R)-2-[(1E,3R)-4-cyclopropyl-3-hydroxybut-1-enyl]-5-oxo pyrrolidin-1-yl}ethyl)benzoic acid: $^1$H NMR (CD$_3$OD) δ 0.00~0.15 (m, 2H), 0.40~0.55 (m, 2H), 0.70~0.82 (m, 1H), 1.25~1.40 (m, 1H), 1.45~1.60 (m, 1H), 1.65~1.80 (m 1H), 2.10~2.45 (m, 3H), 2.75~2.95 (m, 2H), 3.15~3.25 (m, 1H), 3.65~3.80 (m, 1H), 3.90~4.05 (m, 1H), 4.10~4.20 (m, 1H), 5.47 (ddd, J=1.1, 8.7, 15 Hz, 1H), 5.68 (dd, J=6.2, 15 Hz, 1H), 7.28 (d, J=8.1 Hz, 2H), 7.91 (d, J=8.1 Hz, 2H). MS (m/z) 344.1 (M+H).

EXAMPLES 62 AND 63

Synthesis of 4-(2-{(2R)-2-[(1E)-4-cyclopentyl-3-hydroxybut-1-enyl]-5-oxopyrrolidin-1-yl}ethyl)benzoic acid

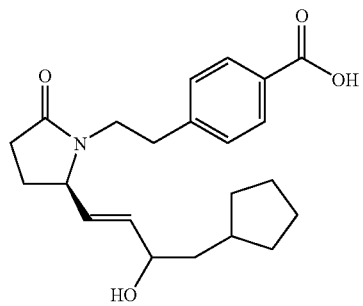

Example 62 and 63 were prepared using the procedure of example 45 and 46 starting from cyclopentylacetic acid.

EXAMPLE 62

4-(2-{(2R)-2-[(1E,3S)-4-cyclopentyl-3-hydroxybut-1-enyl]-5-oxo pyrrolidin-1-yl}ethyl)benzoic acid: $^1$H NMR (CD$_3$OD) δ 1.05~1.20 (m, 2H), 1.40~1.90 (m, 10H), 2.10~2.40 (m, 3H), 2.70~2.95 (m, 2H), 3.08~3.15 (m, 1H), 3.65~3.75 (m, 1H), 3.90~4.00 (m, 1H), 4.05~4.10 (m, 1H), 5.43 (ddd, J=1.1, 8.8, 15 Hz, 1H), 5.64 (dd, J=6.6, 15 Hz, 1H), 7.18 (d, J=8.1 Hz, 2H), 7.87 (d, J=8.1 Hz, 2H). MS (m/z) 372.1 (M+H).

EXAMPLE 63

4-(2-{(2R)-2-[(1E,3R)-4-cyclopentyl-3-hydroxybut-1-enyl]-5-oxo pyrrolidin-1-yl}ethyl)benzoic acid: $^1$H NMR (CD$_3$OD) δ 1.05~1.20 (m, 2H), 1.40~2.00 (m, 10H), 2.10~2.45 (m, 3H), 2.75~3.00 (m, 2H), 3.10~3.30 (m, 1H), 3.65~3.80 (m, 1H), 3.95~4.15 (m, 2H), 5.40 (ddd, J=1.1, 8.8, 15 Hz, 1H), 5.70 (dd, J=6.6, 15 Hz, 1H), 7.33 (d, J=8.4 Hz, 2H), 7.94 (d, J=8.4 Hz, 2H). MS (m/z) 372.1 (M+H).

EXAMPLE 64

Synthesis of 4-(2-{(2R)-2-[(1E)-4-hydroxyoct-1-enyl]-5-oxopyrrolidin-1-yl}ethyl)benzoic acid

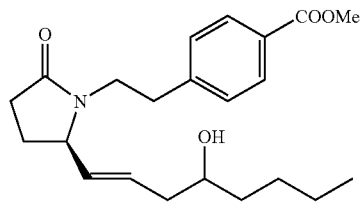

Intermediate 64.1: Synthesis of methyl 4-(2-{(2R)-2-[(1E)-4-hydroxyoct-1-enyl]-5-oxopyrrolidin-1-yl}ethyl)benzoate To a suspension of methyltriphenylphosphonium bromide (220 mg, 0.61 mmol) in dry THF (3 mL) at 0° C. under N$_2$ atmosphere was added n-BuLi (0.25 mL, 1.0M in THF, 0.62 mmol). The resulting blood red colored reaction mixture was stirred for 20 min. and the 1,2-epoxyhexane (80 mg, 0.8 mmol) in THF (3 mL) was added at 0° C. Then the reaction mixture was warmed to room temperature by removing the cold bath, and stirred for 1 h. The reaction mixture was recooled to −25° C., n-BuLi (0.25 mL, 0.62 mmol) was added. Stirred for 20 min, and then intermediate 1.4 (140 mg, 0.5 mmol) in THF (3 mL) was added. The reaction mixture was allowed to warm to room temperature, and stirred overnight. Quenched with water (10 mL). Extracted with EtOAc (3×25 mL), washed with water (10 mL) and brine (10 mL). The organic phase was dried over sodium sulfate, filtered, and concentrated in vacuo. The residue was purified by column chromatography (40% EtOAc/hexane) and the product as a mixture (40 mg, 68%) which was further purified on HPLC; $^1$H NMR (CDCl$_3$): δ 0.89 (t), 1.2-1.5 (m), 1.5-1.7 (m), 2.02-2.46 (m), 2.72-2.98 (m), 3.06-3.20 (m), 3.56-3.82 (m), 3.89 (s), 5.22 (dd, J$_1$=15.4 Hz, J$_2$=8.8 Hz), 5.5-5.7 (m), 7.24 (d, J=8.06 Hz, 2H), 7.94 (d, J=8.06 Hz, 2H);

EXAMPLE 64

4-(2-{(2R)-2-[(1E)-4-hydroxyoct-1-enyl]-5-oxopyrrolidin-1-yl}ethyl) benzoic acid To a solution of intermediate 63.1 (10 mg, 0.026 mmol) in MeOH (3 mL), water (0.2 mL) was added NaOH (4 mg, 0.1 mmol). The resulting solution was heated under microwave oven for 15 min at 80° C. in a sealed tube. Then the reaction mixture was concentrated under reduced pressure. The crude mixture was purified by RP-HPLC using ACN/H$_2$O/TFA, to afford the desired compound (2 mg). $^1$H NMR (CDCl$_3$): δ 0.89 (t, J=7.14 Hz, 3H), 1.18-1.54 (m, 8H), 1.60-1.76 (m, 1H), 2.06-2.44 (m, 6H), 2.74-2.96 (m, 2H), 3.5-3.7 (m, 2H), 3.96 (m, 1H), 5.28 (dd, J$_1$=15.2 Hz, J$_2$=9.15 Hz, 1H), 5.74 (m, 1H), 7.32 (d, J=8.4 Hz, 2H), 7.94 (d, J=8.06 Hz, 2H). The corresponding sodium salt was prepared by treating with 1.1 equiv. NaOH in MeOH for 1 h. The solvent was removed, the residue was dissolved in water (3 mL) and lyophilized.

EXAMPLES 65 AND 66

Synthesis of: 4-[2-((2R)-2-{(1E,3R)-3-[1-(cyclopropylmethyl) cyclobutyl]-3-hydroxyprop-1-enyl}-5-oxopyrrolidin-1-yl)ethyl]benzoic acid

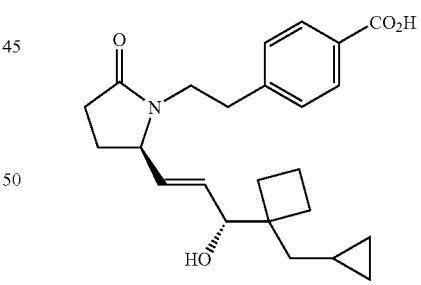

The title compound was synthesized from intermediate 1.4, cyclobutanecarboxylic acid and (bromomethyl)cyclopropane following the procedure described for examples 45 and 46.

EXAMPLE 65

4-[2-((2R)-2-{(1E,3R)-3-[1-(cyclopropylmethyl)cyclobutyl]-3-hydroxyprop-1-enyl}-5-oxopyrrolidin-1-yl)ethyl] benzoic acid (first isomer in HPLC: ACN/H$_2$O/TFA): $^1$H NMR (CD$_3$OD) δ 0.01-0.12 (m, 2H), 0.45-0.49 (m, 2H), 0.73-0.83 (m, 1H), 1.32-1.48 (m, 2H), 1.69-1.91 (m, 4H), 1.99-2.08 (m, 2H), 2.13-2.22 (m, 1H), 2.27-2.42 (m, 2H), 2.74-2.93 (m, 2H), 3.07-3.16 (m, 1H), 3.71-3.80 (m, 1H), 3.92-3.99 (m, 1H), 4.12-4.17 (m, 1H), 5.46-5.54 (m, 1H), 5.70-5.77 (m, 1H), 7.20 (d, J=7.7 Hz, 2H), 7.88 (d, J=8.0 Hz, 2H); MS (m/z) 420 (M+23).

EXAMPLE 66

4-[2-((2R)-2-{(1E,3S)-3-[1-(cyclopropylmethyl)cyclobutyl]-3-hydroxy prop-1-enyl}-5-oxopyrrolidin-1-yl)ethyl] benzoic acid (second isomer in HPLC: ACN/H$_2$O/TFA): $^1$H NMR (CD$_3$OD) δ 0.02-0.11 (m, 2H), 0.45-0.49 (m, 2H), 0.76-0.80 (m, 1H), 1.32 (dd, J=14.2, 6.2 Hz, 1H), 1.47 (dd, J=13.9, 6.6 Hz, 1H), 1.68-1.91 (m, 4H), 1.99-2.08 (m, 2H), 2.10-2.20 (m, 1H), 2.27-2.42 (m, 2H), 2.75-2.93 (m, 2H), 3.11-3.20 (m, 1H), 3.70-3.78 (m, 1H), 3.90-3.97 (m, 1H), 4.13-4.16 (m, 1H), 5.49 (dd, J=15.4, 8.8 Hz, 1H), 5.77 (dd, J=15.4, 5.5 Hz, 1H), 7.20 (d, J=8.4 Hz, 2H), 7.88 (d, J=8.5 Hz, 2H); MS (m/z) 420 (M+23).

EXAMPLE 67

Synthesis of: 4-(2-{(2R)-2-[(1E,3S)-3-hydroxypent-1-enyl]-5-oxo pyrrolidin-1-yl}ethyl)benzoic acid

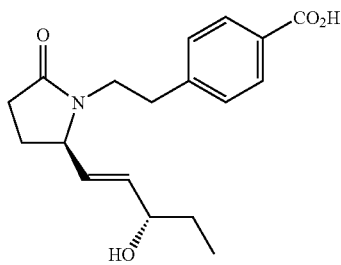

The title compound was synthesized from intermediate 1.4 and methyl propionate following the procedure described for example 9. $^1$H NMR (CD$_3$OD) δ 0.93 (t, J=7.3 Hz, 3H), 1.48-1.58 (m, 2H), 1.66-1.75 (m, 1H), 2.11-2.20 (m, 1H), 2.26-2.41 (m, 2H), 2.75-2.92 (m, 2H), 3.11-3.18 (m, 1H), 3.69-3.76 (m, 1H), 3.88-4.00 (m, 2H), 5.41 (dd, J=15.4, 8.8 Hz, 1H), 5.62 (dd, J=15.4, 6.6 Hz, 1H), 7.19 (d, J=8.1 Hz, 2H), 7.87 (d, J=8.1 Hz, 2H); MS (m/z) 318 (M+1).

EXAMPLE 68

Synthesis of: 4-(2-{(2R)-2-[(1E,3S)-3-hydroxyhex-1-enyl]-5-oxo pyrrolidin-1-yl}ethyl)benzoic acid

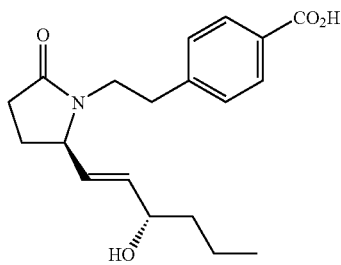

The title compound was synthesized from intermediate 1.4 and methyl butyrate following the procedure described for example 9. $^1$H NMR (CD$_3$OD) δ 0.94 (t, J=7.3 Hz, 3H), 1.3-1.6 (m, 4H), 1.67-1.76 (m, 1H), 2.12-2.21 (m, 1H), 2.26-2.41 (m, 2H), 2.76-2.94 (m, 2), 3.12-3.19 (m, 1H), 3.68-3.76 (m, 1H), 3.93-4.08 (m, 2H), 5.42 (dd, J=15.4, 8.8 Hz, 1H), 5.64 (dd, J=15.3, 6.6 Hz, 1H), 7.26 (d, J=7.6 Hz, 2H), 7.91 (d, J=7.7 Hz, 2H); MS (m/z) 354 (M+23).

EXAMPLE 69

Synthesis of: 4-(2-{(5R)-2-oxo-5-[(1E,3S)-6,6,6-trifluoro-3-hydroxyhex-1-enyl]pyrrolidin-1-yl}ethyl) benzoic acid

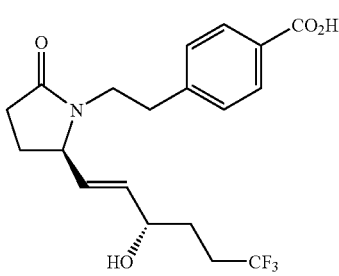

The title compound was synthesized from intermediate 1.4 and ethyl 4,4,4-trifluorobutanoate following the procedure described for example 9. $^1$H NMR (CD$_3$OD) δ 1.63-1.81 (m, 3H), 2.11-2.42 (m, 5H), 2.76-2.93 (m, 2H), 3.12-3.19 (m, 1H), 3.68-3.75 (m, 1H), 3.90-3.95 (m, 1H), 4.11 (dd, J=12.5, 5.5 Hz, 1H), 5.46 (dd, J=15.4, 8.8 Hz, 1H), 5.66 (dd, J=15.4, 5.8 Hz, 1H), 7.21 (d, J=8.1 Hz, 2H), 7.89 (d, J=8.1 Hz, 2H); MS (m/z) 386(M+1).

EXAMPLE 70

Synthesis of: 4-(2-{(2R)-2-[(1E,3S)-3-hydroxy-6-methylhept-1-enyl]-5-oxopyrrolidin-1-yl}ethyl)benzoic acid

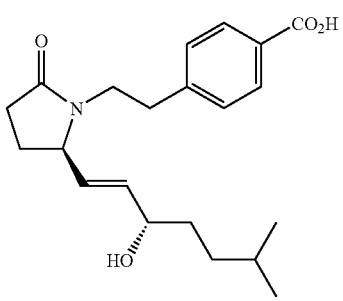

The title compound was synthesized from intermediate 1.4 and methyl 4-methylpentanoate following the procedure described for example 9. $^1$H NMR (CD$_3$OD) δ 0.89 (d, J=6.6 Hz, 6H), 1.15-1.34 (m, 2H), 1.45-1.59 (m, 3H), 1.67-1.76 (m, 1H), 2.12-2.21 (m, 1H), 2.26-2.42 (m, 2H), 2.76-2.93 (m, 2H), 3.11-3.19 (m, 1H), 3.69-3.76 (m, 1H), 3.92-4.04 (m, 2H), 5.41 (dd, J=15.4, 8.8 Hz, 1H), 5.64 (dd, J=15.3, 6.6 Hz, 1H), 7.22 (d, J=8.4 Hz, 2H), 7.89 (d, J=8.1 Hz, 2H); MS (m/z) 382 (M+23).

EXAMPLE 71

Synthesis of: 4-(2-{(2R)-2-[(1E,3S)-6-cyclopropyl-3-hydroxyhex-1-enyl]-5-oxopyrrolidin-1-yl}ethyl)benzoic acid

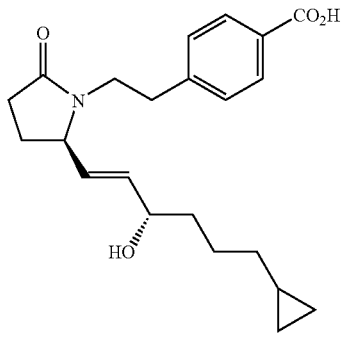

The title compound was synthesized following the procedure described for example 9 from intermediate 1.4 and methyl 4-cyclopropylbutanoate (obtained by esterification of 4-cyclopropylbutanoic acid using the procedure described for intermediate 5.1; for synthesis of 4-cyclopropylbutanoic acid, see *J. Med. Chem.* 1998, 41, 1112). $^1$H NMR (CD$_3$OD) δ −0.03−−0.02 (m, 2H), 0.36-0.40 (m, 2H), 0.60-0.68 (m, 1H), 1.19-1.25 (m, 2H), 1.41-1.59 (m, 4H), 1.67-1.75 (m, 1H), 2.12-2.21 (m, 1H), 2.26-2.42 (m, 2H), 2.76-2.93 (m, 2H), 3.12-3.19 (m, 1H), 3.69-3.76 (m, 1H), 3.91-3.96 (m, 1H), 4.02-4.07 (m, 1H), 5.41 (dd, J=15.0, 8.8 Hz, 1H), 5.63 (dd, J=15.4, 6.6 Hz, 1H), 7.22 (d, J=8.5 Hz, 2H), 7.89 (d, J=8.1 Hz, 2H); MS (m/z) 394 (M+23).

EXAMPLE 72

Synthesis of: 4-(2-{(2R)-2-[(1E,3R)-4-(allyloxy)-3-hydroxybut-1-enyl]-5-oxopyrrolidin-1-yl}ethyl)benzoic acid

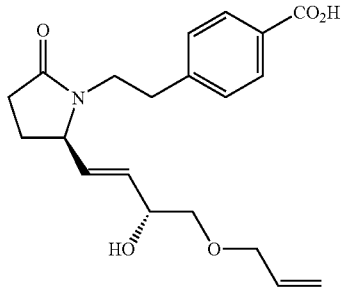

Intermediate 72.1: methyl (allyloxy)acetate

To a suspension of sodium hydride (1.76 g, 60% in oil, 44.0 mmol) in DMF (40 mL) cooled at 0° C. was added dropwise methyl glycolate (3.09 mL, 3.60 g, 40.0 mmol). The mixture was warmed to 25° C., stirred for 1 h and cooled down to 0° C., before allyl bromide (3.81 mL, 5.32 g, 44.0 mmol) was added dropwise. The solution was warmed to 25° C., stirred for 1 h, poured in a saturated solution of NH$_4$Cl (100 mL) and extracted with ethyl acetate (3×50 mL). The organic phases were washed with brine (2×50 mL), dried over sodium sulfate and the concentrated. The residue was distilled in vacuo utilizing a Vigreux column to afford the ester (2.77 g, 53%) as a colorless oil (b.p. 54-55° C./2 mmHg). $^1$H NMR (CDCl$_3$) δ 3.74 (s, 3H), 4.06-4.08 (m, 4H), 5.21 (d, J=10.2 Hz, 1H), 5.29 (d, J=17.2 Hz, 1H), 5.84-5.94 (m, 1H).

4-(2-{(2R)-2-[(1E,3R)-4-(allyloxy)-3-hydroxybut-1-enyl]-5-oxopyrrolidin-1-yl}ethyl)benzoic acid: This compound was synthesized from intermediate 1.4 and intermediate 71.1 following the procedure described for example 9. $^1$H NMR (CD$_3$OD) δ 1.67-1.77 (m, 1H), 2.12-2.21 (m, 1H), 2.26-2.42 (m, 2H), 2.76-2.93 (m, 2H), 3.14-3.21 (m, 1H), 3.41-3.43 (m, 2H), 3.66-3.74 (m, 1H), 3.92-3.98 (m, 1H), 4.01 (d, J=5.5 Hz, 2H), 4.26 (dd, J=11.4, 5.2 Hz, 1H), 5.14 (d, J=10.3 Hz, 1H), 5.27 (d, J=17.6 Hz, 1H), 5.53 (dd, J=15.3, 8.8 Hz, 1H), 5.69 (dd, J=15.3, 5.8 Hz, 1H), 5.84-5.94 (m, 1H), 7.24 (d, J=8.5 Hz, 2H), 7.90 (d, J=8.0 Hz, 2H); MS (m/z) 360 (M+1).

EXAMPLE 73

Synthesis of: 4-(2-{(2R)-2-[(1E,3R)-3-hydroxy-4-phenoxybut-1-enyl]-5-oxopyrrolidin-1-yl}ethyl)benzoic acid

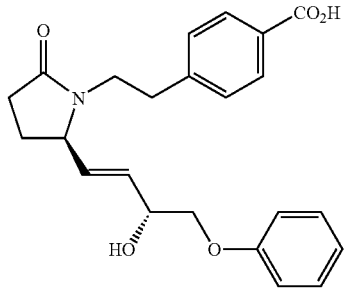

The title compound was synthesized from intermediate 1.4 and methyl phenoxyacetate following the procedure described for example 9. $^1$H NMR (CD$_3$OD) δ 1.68-1.77 (m, 1H), 2.12-2.21 (m, 1H), 2.27-2.41 (m, 2H), 2.72-2.90 (m, 2H), 3.12-3.22 (m, 1H), 3.67-3.75 (m, 1H), 3.88-3.97 (m, 3H), 4.46 (m, 1H), 5.58 (dd, J=15.3, 7.7 Hz, 1H), 5.74 (dd, J=15.4, 5.9 Hz, 1H), 6.90-6.94 (m, 3H), 7.15 (d, J=8.4 Hz, 2H), 7.23-7.28 (m, 2H) 7.84 (d, J=8.4 Hz, 2H); MS (m/z) 396 (M+1).

EXAMPLE 74

Synthesis of 4-(2-{(2R)-2-[(1E)-3-hydroxy-3-methyloct-1-enyl]-5-oxopyrrolidin-1-yl}ethyl)benzoic acid

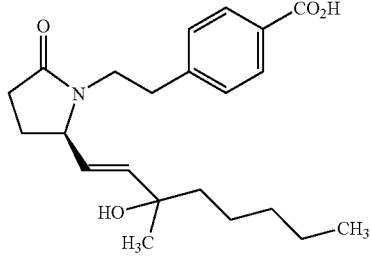

Intermediate 74.1: methyl 4-(2-{(2R)-2-[(1E)-3-hydroxy-3-methyloct-1-enyl-5-oxopyrrolidin-1-yl}ethyl)benzoate To a solution of intermediate 1.5 (0.5 g, 1.34 mmol) in toluene (40 mL) was added dropwise a toluene solution of trimethyl aluminum (1.34 mL, 2M, 2.69 mmol). The resulting clear solution was stirred at RT for 1 h then quenched with MeOH (1 mL) and water (2 mL). The mixture was stirred vigorously for 30 min. then filtered through celite. The clear solution was concentrated in vacuo to afford the title intermediate that was used in the next step without further purification. R$_f$ 0.5 (EtOAc).

EXAMPLE 74

4-(2-{(2R)-2-[(1E)-3-hydroxy-3-methyloct-1-enyl]-5-oxopyrrolidin-1-yl}ethyl) benzoic acid To a solution of intermediate 73.1 (0.5 g, 1.3 mmol) in water (2 mL), MeOH (6 mL), and THF (6 mL) was added NaOH (0.26 g, 6.4 mmol). The resulting solution was stirred at RT for 5 h then was concentrated under reduced pressure. The crude mixture was purified by RP-HPLC using ACN/H$_2$O 0.1% TFA to afford the desired compounds as an inseparable mixture of diastereisomers. MS (m/z) 374.5 (M+1).

EXAMPLES 75 AND 76

Synthesis of 4-(2-{(2R)-2-[(1E)-3-hydroxy-5-methoxypent-1-enyl]-5-oxopyrrolidin-1-yl}ethyl)benzoic acid

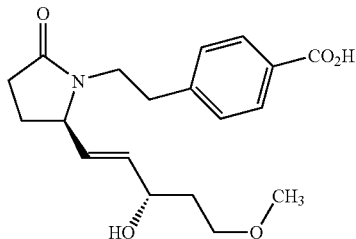

The title compounds were obtained as described for example 14 and 15 starting from intermediate 1.4, methyl-3-methoxypropionate, and dimethyl methylphosphonate.

EXAMPLE 75

(first isomer in RP-HPLC; ACN/H2O 0.1% TFA): $^1$H-NMR (CD$_3$OD) δ 1.60-1.85-(m, 3H), 2.08-2.20 (m, 1H), 2.26-2.42 (m, 2H), 2.80-2.93 (m, 2H), 3.10-3.21 (m, 1H), 3.42-3.55 (m, 2H), 3.65-3.75 (m, 1H), 3.90-4.00 (m, 1H), 4.15-4.22 (m, 1H), 5.37 (dd, 1H), 5.54 (dd, 1H), 7.28 (d, 2H), 7.80 (d, 2H); MS (m/z) 348 (M+1).

EXAMPLE 76

(second isomer in RP-HPLC; ACN/H2O 0.1% TFA): $^1$H-NMR (CD$_3$OD) δ 1.60-1.85 (m, 3H), 2.05-2.20 (m, 1H), 2.22-2.42 (m, 2H), 2.80-2.93 (m, 2H), 3.16-3.27 (m, 1H), 3.42-3.58 (m, 2H), 3.60-3.75 (m, 1H), 3.88-3.97 (m, 1H), 4.15-4.22 (m, 1H), 5.33 (dd, 1H), 5.57 (dd, 1H), 7.28 (d, 2H), 7.82 (d, 2H); MS (m/z) 348 (M+1).

EXAMPLE 77

Synthesis of 4-(2-{(2R)-2-[(1E,3S)-3-hydroxyhepta-1,6-dienyl]-5-oxopyrrolidin-1-yl}ethyl)benzoic acid

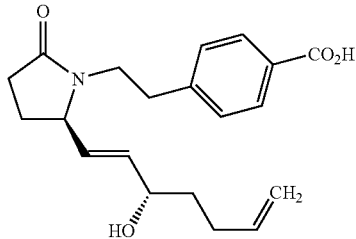

The title compound was obtained as described for example 9 starting from intermediate 1.4, ethyl-4-pentenoate, and dimethyl methylphosphonate. $^1$H-NMR (CD$_3$OD) δ 1.50-1.80 (3H), 2.10-2.21 (m, 3H), 2.22-2.43 (m, 2H), 2.73-2.97 (m, 2H), 3.10-3.20 (m, 1H), 3.65-3.80 (m, 1H), 3.88-3.98 (m, 1H), 4.05-4.12 (m, 1H), 4.90-5.08 (m, 2H), 5.38-5.48 (dd, 1H), 5.60-5.70 (dd, 1H), 5.79-5.92 (m, 1H), 7.19 (d, 2H), 7.87 (d, 2H); MS (m/z) 344 (M+1).

EXAMPLE 78

Synthesis of 4-(2-{(2R)-2-[(1E)-3-hydroxy-5-morpholin-4-ylpent-1-enyl]-5-oxopyrrolidin-1-yl}ethyl) benzoic acid

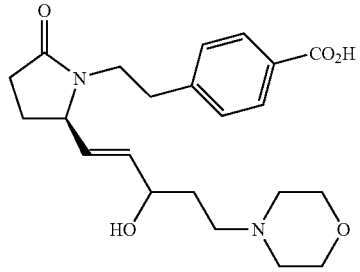

The title compound was obtained as described for example 14 and 15 as a mixture of diastereoisomers starting from intermediate 1.4, ethyl 3-(4-morpholino)propionate, and dimethyl methylphosphonate. $^1$H-NMR (D2O) δ 1.64-1.78 (m, 1H), 1.82-2.00 (m, 2H), 2.10-2.20 (m, 1H), 2.25-2.45 (m, 2H), 2.85-2.95 (m, 2H), 3.05-3.35 (m, 5H), 3.42-3.52 (m, 2H), 3.65-3.85 (m, 3H), 3.95-4.15 (m, 3H), 4.20-4.30 (m, 1H), 5.40-5.52 (m, 1H), 5.58-5.70 (m, 1H), 7.35 (d, 2H), 7.94 (d, 2H); MS (m/z) 403 (M+1).

EXAMPLE 79

4-{2-[(2R)-2((1E,3R)-5-cyclopentyl-3-hydroxypentyl-1-enyl)-5-oxopyrrolidin-1-yl}ethyl}benzoic acid

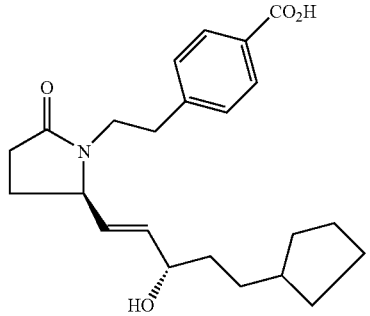

Intermediate 79.1. Dimethyl 4-cyclopentyl-2-oxobutylphosphonate

To a solution of dimethyl methylphosphonate (2.17 ml, 20 mmol) in anhydrous THF (20 mL), cooled at −78° C. was added n-BuLi (1.6 M in hexane, 13.7 mL, 22 mmol). The mixture was stirred for 30 minutes at this temperature under nitrogen. Methyl 3-cyclopentylpropanoate (1.56 g, 10 mmol), prepared from 3-cyclopentylpropionic acid (Aldrich) and methanol at the presence of the catalytic amount of the concentrated sulfuric acid (the procedure described in Intermediate 17.1), was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc:Hexanes=1:1) to give the product (1.80 g) with colorless oil in 82% yield. $^1$HNMR (CD$_3$OD, ppm) δ 1.03 (m, 2H), 1.51 (m, 1H), 1.61 (m, 6H), 1.73 (m, 2H), 2.63 (t, J=7.4 Hz, 2H), 3.09 (d, J=22.7 Hz, 2H), 3.76 (s, 3H), 3.87 (s, 3H)

Intermediate 79.2. Methyl 4-{2-{(2R)-2[(1E)-5-cyclopentyl-3-oxopenty-1-enyl]-5-oxopyrrolidin-1-yl}ethyl)benzoate To a solution of intermediate 79.1 (200 mg, 0.908 mmol) in anhydrous THF (10 mL) at 0° C. was added 60% NaH (43.6 mg, 1.09 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$. The residue was purified through silica gel to afford the compound (200 mg) in 55% yield. $^1$HNMR (CD$_3$Cl, ppm) δ 1.07 (m, 2H), 1.49 (m, 1H), 1.51 (m, 4H), 1.72 (m, 4H), 2.06 (m, 1H), 2.35 (m, 3H), 2.52 (t, J=7.6 Hz, 2H), 2.87 (m, 2H), 3.05 (m, 1H), 3.89 (m, 1H), 3.90 (s, 3H), 6.07 (d, J=15.7 Hz, 1H), 6.44 (dd, J=8.1 and 15.7 Hz, 1H), 7.25 (d, J=8.1 Hz, 2H), 7.95 (d, J=8.1 Hz, 2H).

Intermediate 79.3. Methyl 4-{2-{(2R)-2[(1E,3R)-5-cyclopentyl-3-hydroxypent-1-enyl]-5-oxopyrrolidin-1-yl}ethyl)benzoate To a solution of (R)-2-methyl-CBS-oxazaborolidine (1.0 M in to toluene, 0.39 mL, 0.39 mmol) in anhydrous THF (10 mL) at 0° C. was added Borane-THF complex (1.0 M, 0.39 mL, 0.39 mmol) dropwise. The mixture was stirred for 15 minutes. Intermediate 79.2 (140 mg, 0.35 mmol) in THF (1 mL) was added dropwise. The mixture was stirred for 3 hours. The mixture was quenched with addition of 1 mL of the saturated ammonia chloride and was dilute with EtOAc (20 mL). The organic layer was washed with brine (3×5 mL), dried over MgSO4. The residue was used for the next reaction without purification.

Intermediate 79.4. 4-{2-{(2R)-2[(1E,3R)-5-cyclopentyl-3-hydroxypent-1-enyl]-5-oxo pyrrolidin-1-yl}ethyl)benzoate Intermediate 79.3 (80 mg, 0.20 mmol) was dissolved in MeOH/THF/H$_2$O (1/1/1 mL) and added NaOH (1.0 M, 0.50 mL, 0.50 mmoL). The mixture was stirred for overnight. The residue was purified through RP-HPLC using ACN and H$_2$O/0.1% TFA to afford product (52 mg) as a white solid. $^1$HNMR (CD$_3$OD, ppm) δ 1.08 (m, 2H), 1.30-1.49 (m, 2H), 1.53 (m, 4H), 1.76 (m, 4H), 2.06 (m, 1H), 2.35 (m, 2H), 2.89 (m, 1H), 2.87 (m, 1H), 3.15 (m, 1H), 3.71 (m, 1H), 3.91 (m, 1H), 4.03 (m, 1H), 5.41 (dd, J=8.8 and 15.4 Hz, 1H), 5.62 (dd, J=6.6 and 15.4 Hz, 1H), 7.21 (d, J=8.0 Hz, 2H), 7.88 (d, J=8.0 Hz, 2H). (m/z): 408.4 (M+Na$^+$).

EXAMPLE 80

4-{2-[(2R)-2((1E,3R)-3-hydroxy-7-methyloct-1-enyl)-5-oxopyrrolidin-1-yl}ethyl}benzoic acid

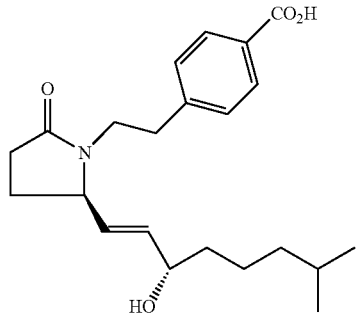

Intermediate 80.1. Dimethyl 6-methyl-2-oxoheptylphosphonate

To a solution of dimethyl methylphosphonate (2.17 ml, 20 mmol) in anhydrous THF (20 mL), cooled at −78° C. was added n-BuLi (1.6 M in hexane, 13.7 mL, 22 mmol). The mixture was stirred for 30 minutes at this temperature under nitrogen. Methyl 5-methylhexanoate (1.44 g, 10 mmol), prepared from 5-methylhexanoic acid (from Avocado) and methanol at the presence of the catalytic amount of the concentrated sulfuric acid (the procedure described in Intermediate 17.1), was added dropwise for 10 minutes. The mixture was stirred for 2 hours at −78° C., gradually was warm to room temperature. The mixture was quenched with addition of 1N HCl to pH 4-5. The organic layer was separated, washed with brine and dried over MgSO$_4$. The residue was purified through flash chromatography on silica gel (EtOAc:Hexanes=1:1) to give the product (1.80 g) with colorless oil in 76% yield. $^1$HNMR (CD$_3$OD, ppm) δ 0.866 (d, J=6.5 Hz, 6H), 1.16 (m, 2H), 1.56 (m, 3H), 2.58 (t, J=7.3 Hz, 2H), 3.10 (d, J=22.7 Hz, 2H), 3.70 (s, 3H), 3.79 (s, 3H)

Intermediate 80.2. Methyl 4-{2-{(2R)-2[(1E)-7-methyl-3-oxooct-1-enyl]-5-oxo pyrrolidin-1-yl}ethyl)benzoate To a solution of intermediate 80.1 (236 mg, 1.0 mmol) in anhydrous THF (10 mL) at 0° C. was added 60% NaH (43.6 mg, 1.1 mmol) in mineral oil. The mixture was stirred for 10 minutes. Intermediate 1.4 (250 mg, 0.908 mmol) in THF (1 mL) was added dropwise. The mixture was stirred for overnight. The mixture was quenched with addition of the saturated ammonia chloride. The mixture was dilute with Ethyl acetate (15 mL). The organic layer was washed with brine (3×5 mL), dried over MgSO$_4$. The residue was purified through silica gel to afford the compound (110 mg). $^1$HNMR (CD$_3$Cl, ppm) δ 0.877 (d, J=6.6 Hz, 6H), 1.18 (m, 3H), 1.56 (m, 9H), 1.73 (m, 1H), 2.10 (m, 2H), 2.39 (m, 2H), 2.50 (t, J=7.4 Hz, 2H), 2.58 (t, J=7.3 Hz, 2H), 3.87 (m, 1H), 3.90 (s, 3H), 6.09 (d, J=15.8 Hz, 1H), 6.45 (dd, J=8.0 and 15.8 Hz, 1H), 7.23 (d, J=8.1 Hz, 2H), 7.97 (d, J=8.1 Hz, 2H).

Intermediate 80.3. Methyl 4-{2-{(2R)-2[(1E,3R)-3-hydroxy-7-methyloct-1-enyl]-5-oxopyrrolidin-1-yl}ethyl)benzoate To a solution of (R)-2-methyl-CBS-oxazaborolidine (1.0 M in to toluene, 0.28 mL, 0.28 mmol) in anhydrous THF (10 mL) at 0° C. was added Borane-THF complex (1.0 M, 0.28 mL, 0.28 mmol) dropwise. The mixture was stirred for 15 minutes. Intermediate 80.2 (90 mg, 0.23 mmol) in THF (1 mL) was added dropwise. The mixture was stirred for 3 hours. The mixture was quenched with addition of 1 mL of the saturated ammonia chloride and was dilute with EtOAc (10 mL). The organic layer was washed with brine (3×3 mL), dried over MgSO4. The residue was used for the next reaction without purification.

Intermediate 80.4. 4-{2-{(2R)-2[(1E,3R)-3-hydroxy-7-methyloct-1-enyl]-5-oxopyrrolidin-1-yl}ethyl)benzoate Intermediate 80.3 (80 mg, 0.207 mmol) was dissolved in MeOH/THF/H$_2$O (1/1/1 mL) and added NaOH (1.0 M, 0.50 mL, 0.50 mmoL). The mixture was stirred for overnight. The residue was purified through RP-HPLC using ACN and H$_2$O/0.1% TFA to afford product (52 mg) as a white solid. $^1$HNMR (CD$_3$OD, ppm) δ 0.874 (d, J=6.6 Hz, 6H), 1.21 (m, 2 H), 1.34 (m, 1H), 1.51 (m, 4H), 1.73 (m, 1H), 2.19 (m, 1H), 2.32 (m, 2H), 2.79 (m, 1H), 2.86 (m, 1H), 3.14 (m, 1H), 3.73 (m, 1H), 3.92 (m, 1H), 4.03 (m, 1H), 5.42 (dd, J=8.8 and 15.8 Hz, 1H), 5.60 (dd, J=6.6 and 15.8 Hz, 1H), 7.22 (d, J=8.5 Hz, 2H), 7.88 (d, J=8.5 Hz, 2H). (m/z): 374.2 (M+H$^+$).

EXAMPLE 81

Prostaglandin EP2 Binding Assay

Compounds of the invention were tested in an EP2 receptor binding assay of the following protocol. As referred to herein, the term an "EP2 receptor binding assay" designates the following protocol.

A mixture containing 20 µg of EP2 receptor membranes, 0.5 mg of wheat germ agglutinin coated PVT-SPA beads, plus or minus a 1,2-substituted 5-pyrrolidinone compound of the invention (25 µl per well) or 10 µM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad® prism program. EP2 Ki values are set forth in the Table 1 which follows Example 84 below.

EXAMPLE 82

EP2 cAMP Assay

Compounds of the invention were tested in a total cAMP assay as follows. HEK293-EBNA cells transfected with pCEP4-hEP2 receptors were seeded in 96 well opaque plate (Costar #3917) at 4×10$^4$ cells per well in 100 µl of culture medium (D-MEM/F12 supplemented with 10% FBS, 2 nM L-glutamine, and 250 µg/ml of hygromycin; all from Gibco-BRL) and incubated at 37° C. After overnight incubation, the medium was removed from each well and replaced with 45 µl of assay medium consisted of phenol red free D-MEM/F-12, 0.1% BSA (GibcoBRL) and 0.1 mM3-isobutyl-1-methylxanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extracellular) was measured by using a cAMP-screen ELISA System (Tropix, #CS1000). Results (EP2 EC$_{50}$ (µM)) are shown in Table 1 which follows Example 84 below.

EXAMPLE 83

EP4 Binding Assay

Compounds of the invention were tested in an EP4 receptor binding assay of the following protocol.

A mixture containing 20 µg of EP4 receptor membranes, 0.5 mg of wheat germ agglutinin coated PVT-SPA beads, plus or minus a 1,2-substituted 5-pyrrolidinone compound of the invention (25 µl per well) or 10 µM of cold PGE2 at 1% DMSO and 20 nM $^3$H-PGE2 in assay buffer containing 25 mM MES, 10 mM MgCl$_2$, 1 mM EDTA, pH 6.0 are incubated in Corning 3600 plates on a plate shaker for 2 hrs at room temperature. $^3$H-PGE2 binding is evaluated by counting the plates on the top count using the $^3$H SPA dpm2 program. % Binding and Ki value for inhibitors are calculated based on the one site competition parameter using the Graphpad® prism program. EP4 Ki values are set forth in the Table 1 which follows Example 84 below.

EXAMPLE 84

EP4 cAMP Assay

Compounds of the invention were tested in a total cAMP assay as follows. HEK293-EBNA cells transfected with pCEP4-hEP4 receptors were seeded in 96 well opaque plate (Costar #3917) at 4×10$^4$ cells per well in 100 µl of culture medium (D-MEM/F12 supplemented with 10% FBS, 2 nM L-glutamine, and 250 µg/ml of hygromycin; all from Gibco-BRL) and incubated at 37° C. After overnight incubation, the medium was removed from each well and replaced with 45 µl of assay medium consisted of phenol red free D-MEM/F-12, 0.1% BSA (GibcoBRL) and 0.1 mM3-isobutyl-1-methylxanthine (Sigma). After 15 minutes of incubation at 37° C., 16-16-dimethyl PGE-2 or compounds at desired concentrations in 20 µl of assay medium were added to cells and further incubated at 37° C. for 1 hour. Total cAMP (intra- and extracellular) was measured by using a cAMP-screen ELISA System (Tropix, #CS1000). Results (EP4 EC$_{50}$ (µM)) are shown in the Table 1 immediately below.

Results of the assays of Examples 81, 82, 83 and 84 are set forth in the following Table 1 wherein the tested compound is identified both by the corresponding synthetic Example number above as well as structure of the tested compound.

TABLE 1

| Example No. | Structure | h-EP2 Ki (nM) | h-EP4 Ki (nM) | h-EP2 EC$_{50}$ (nM) | h-EP4 EC$_{50}$ (nM) |
|---|---|---|---|---|---|
| 6 | 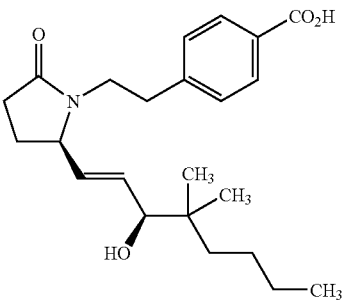 | 2100 | 20 | | |

TABLE 1-continued

| Example No. | Structure | h-EP2 Ki (nM) | h-EP4 Ki (nM) | h-EP2 EC$_{50}$ (nM) | h-EP4 EC$_{50}$ (nM) |
|---|---|---|---|---|---|
| 5 | 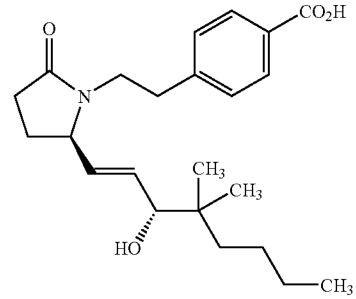 | 1237 | 0.732 | | |
| 8 | 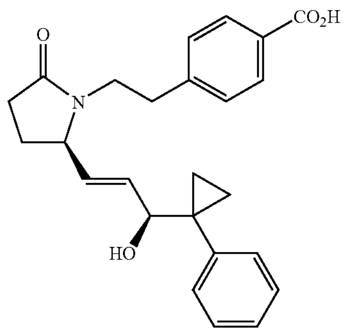 | 1930 | 25 | | |
| 7 | 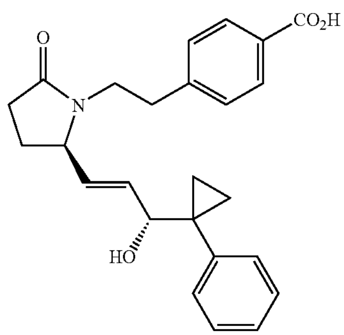 | 220 | 16 | | |
| 1 | 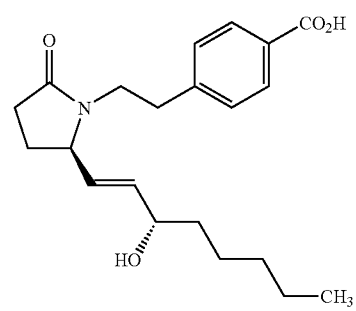 | 120 | 2 | 15 | 0.002 |

TABLE 1-continued

| Example No. | Structure | h-EP2 Ki (nM) | h-EP4 Ki (nM) | h-EP2 EC$_{50}$ (nM) | h-EP4 EC$_{50}$ (nM) |
|---|---|---|---|---|---|
| 3 | (structure) | | N.C. | | 4.0 |
| 4 | (structure) | | N.C. | | |

N.C. = not complete

Further data obtained from the assays 83 and 84 for compounds of the invention are listed in Table 2, together with reference compounds, sulprostone and butaprost.

TABLE 2

| Example Number | h-EP4 Ki (nM) | h-EP4 EC$_{50}$ (nM) |
|---|---|---|
| 5 | 9 | 0.014 |
| 7 | 2 | n.a. |
| 9 | 0.5 | 30 |
| 10 | 1 | n.a. |
| 31 | 0.05 | 0.03 |
| 45 | 2 | 0.3 |
| Butaprost | >10 000 | n.a. |
| Sulprostone | 7740 | n.a. |

EXAMPLE 85

In Vivo Ovulation Assay

Ovulation triggering activity of compounds of the invention are tested in a mature mouse ovulation induction model.

Mature 10-week-old CD-mice are used. Reagents are prepared as follows: PMSG (pregnant mare serum gonadotropin) (Calbiochem, cat #367222) and hCG (Serono) are diluted in PBS. PGE2 (Cayman, Ann Arbor Mich.) is dissolved in ethanol and diluted with 0.154 M NaHCO$_2$ Buffer (pH 8.0) to final concentration of ethanol of less than 3 percent. A test compound (based on solubility) is pre-dissolved in ethanol, DMSO or other reagents. Test compound is then diluted with saline or other diluents such as PBS or NP3S (5% N-methyl-pyrrolidinone/30% PEG-400/25% PEG-200/20% Propylene Glycol in saline). PMSG serves to stimulate follicule growth and maturation. Mature follicules will ovulate when an ovulation triggering dose of hCG or an hCG replacement is administered.

The following test protocol was employed for the test animals (typically 5 animals per test group).

Day 1: Inject 5 IU PMSG in 200 UL PBS (i.p. 15:00 PM)
Day 2: No administration
Day 3: Inject an ovulation triggering dose of hCG (i.p.) or hCG replacement (PGE2 or compound of the invention, s.c., i.v. or oral route), 15:00 PM
Day 4: Eighteen hours after injections of ovulation triggers, animals were sacrificed by CO$_2$ asphyxiation and abdominal cavities were opened using fine scissors and forceps. Uterus, oviducts and ovaries were collected and placed in pre-labeled dishes containing phosphate buffered saline (PBS). The collected tissues were transferred to the laboratory and intact oviduct carefully dissected out from uterus and ovary under the dissection microscope. The dissected oviducts were placed on the glass microscopic slide and covered with another slide. Two slides were taped on two edges. The numbers of ovulated ova in the oviducts were counted using upright microscope with 4× objective and recorded.

For evaluating the oral activity of this compound, two experiments were conducted, the first experiment was conducted with non-fasted animals and the second experiment was conducted in 24 h fasted animals (water provided). The compounds of the invention, according to their solubility are pre-dissolved in ethanol, DMSO or other reagents. The compounds of the invention are then diluted with saline or other diluents such as PBS or NP3S before oral administration.

A) Compound 1:

Compound of example 1 is submitted to different testing in the in vivo ovulation induction model as described above in order to assess its ability to trigger ovulation via subcutaneous (sc), oral (po) and intravenous (iv) routes of administration.

Experimental Groups:

| Groups | N/Group | Priming | Treatments |
| --- | --- | --- | --- |
| Group 1 | n = 5 | 5IU PMSG | Control Vehicle |
| Group 2 | n = 5 | 5IU PMSG | HCG (0.12 mg/kg i.p.) |
| Group 3 | n = 5 | 5IU PMSG | PGE2 (13.5 mg/kg) |
| Group 4 | n = 5 | 5IU PMSG | Test compound* (10 mg/kg) |
| Group 5 | n = 5 | 5IU PMSG | Test compound* (30 mg/kg) |
| Group 6 | n = 5 | 5IU PMSG | Test compound* (90 mg/kg) |

The following results were obtained:
An average of 27.2 ova were obtained with Group 2;
an average of 19.4 ova were obtained for Group 3;
an average of 25 ova were obtained for Group 4;
an average of 22.4 ova were obtained for Group 5;
and an average of 25.2 ova were obtained for Group 6.
*The test compound used by s.c. injection with Groups 4, 5 and 6 was 4-(2-{(2R)-2-[(1E)-3-hydroxyoct-1-enyl]-5-oxopyrrolidin-1-yl}ethyl)benzoic acid (compound of Example 1 above).

Compound of example 1 was found active in the mice ovulation induction model via subcutaneous (sc), oral (po) and intravenous (iv) routes of administration.

Figure 2:
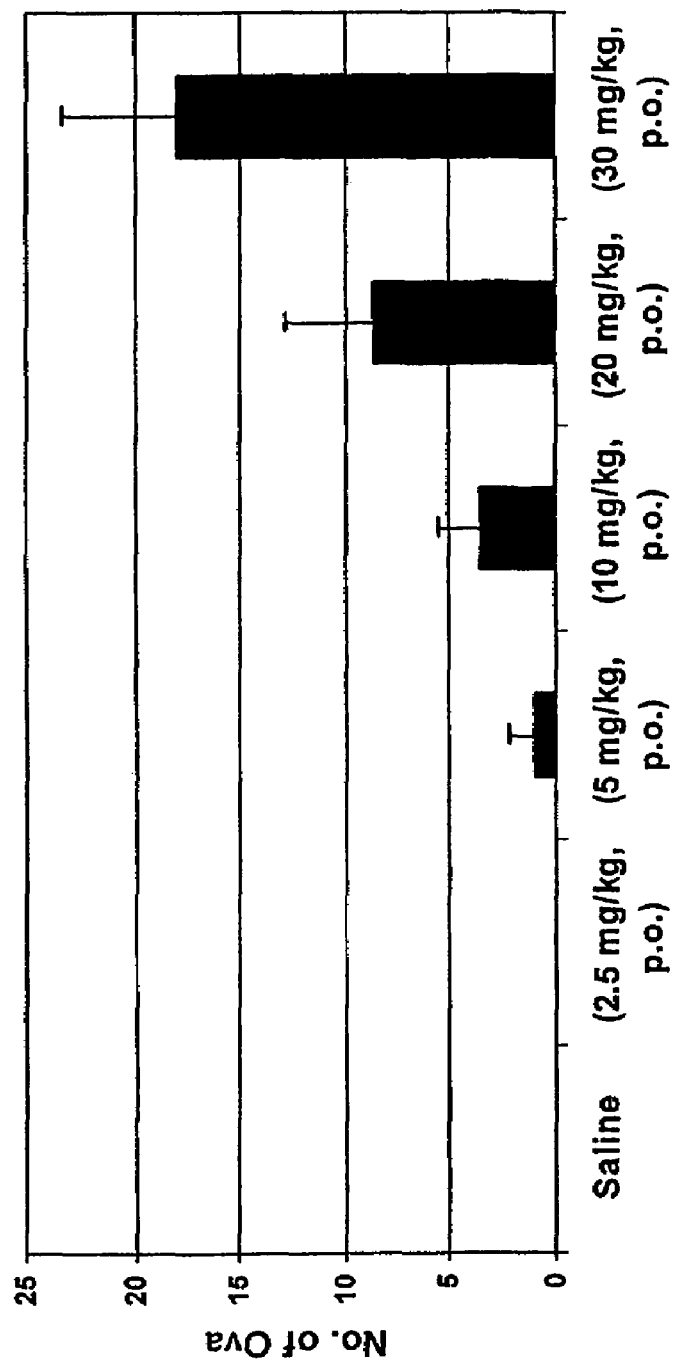
FIG. 2 reports the number of ova released after oral administration of compound of Example 1 in mature 10-week CD-1 mice, 48 hours after an injection of 5IU PMSG (i.p.). The number of ova released is shown for different doses of oral administration of compound of Example 1.

As described in FIG. 2, the calculated $ED_{50}$ (dose of drug which produces 50% of its minimum response or effect) for compound 1 by s.c. route is 3.9 mg/kg (FIG. 1). The calculated $ED_{50}$ for compound 1 in non-fasted animals is 21.97 mg/kg (FIG. 2). The results with fasted animals were similar to the non-fasted experiment and calculated $ED_{50}$ is 21.1 mg/kg.

B) EP4 Agonists:

EP4 agonists are selected as described in Examples 83 and/or 84 on the basis of their Ki and/or $EC_{50}$ values.

The compounds of the invention are then tested in the in vivo ovulation induction model as described above in order to calculated the $ED_{50}$ for subcutaneous (s.c.) and oral (po) routes of administration. Data for reference compounds (sulprostone and butaprost) that do not fulfill the selection criteria for EP4 agonists are also given (Table 3 below).

TABLE 3

| Example number | Ovulation Induction ($ED_{50}$, mg/kg) | |
| --- | --- | --- |
| | s.c. | p.o. |
| 1 | 3.8 | 22 |
| 5 | 3 | 18 |
| 7 | 0.73 | n.a. |
| 9 | n.a. | 1 |
| 31 | 0.32 | 1 |
| 45 | n.a. | 1 |
| Butaprost | No activity up to 30 mg/kg | n.a. |
| Sulprostone | No activity up to 27 mg/kg | n.a. |

Figure 3:
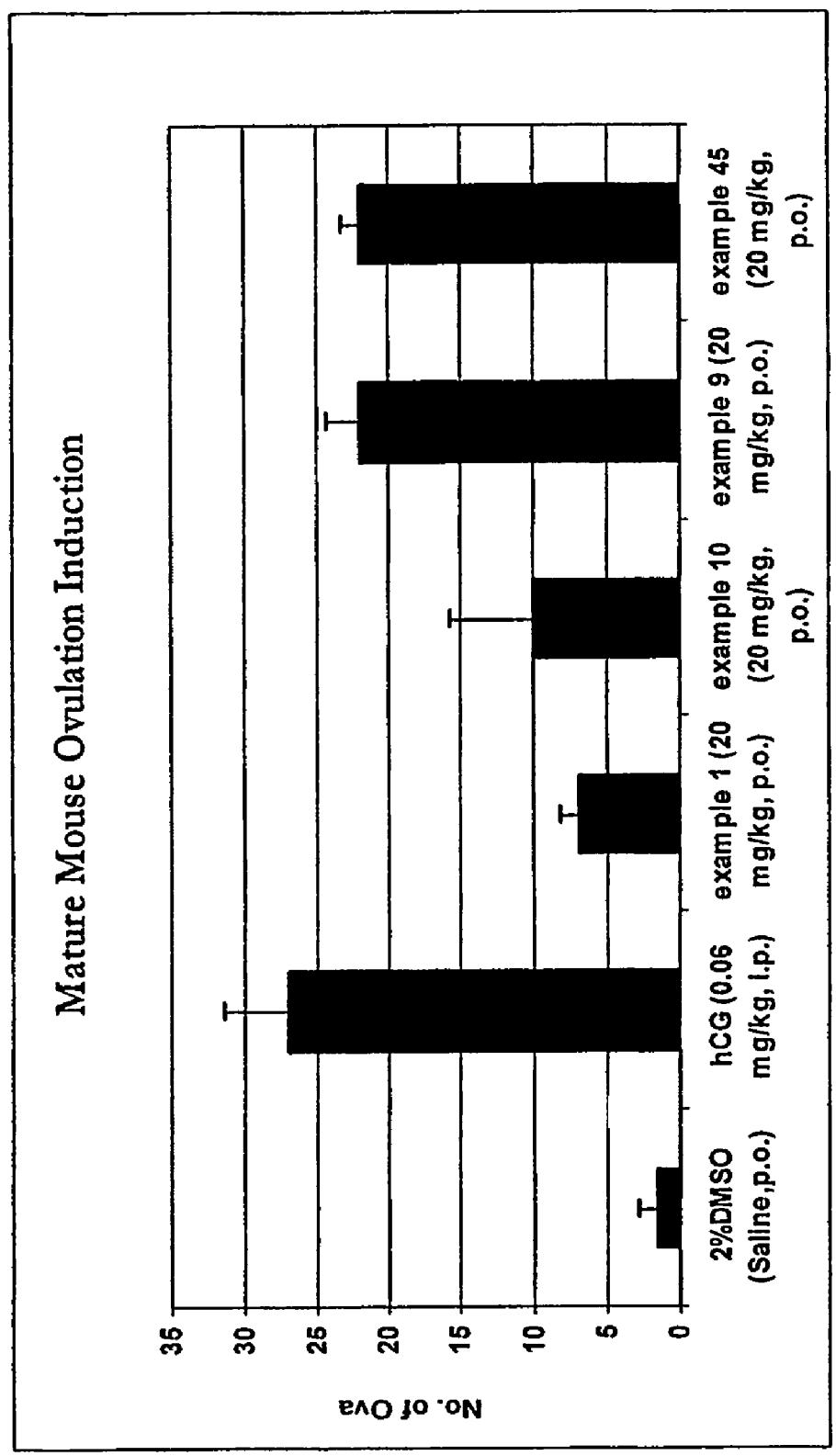
FIG. 3 reports the number of ova released after oral administration of compounds of the invention at the single dose of 20 mg/kg.

Oral activity in the in vivo model of ovulation induction is evaluated for other compounds of the invention at the single dose of 20 mg/kg. Data are shown on FIG. 3.

Other examples of EP4 selective agonists are the following:
4-(2-{2-.[4-(3-iodophenyl)-3-hydroxybutyl]-5-oxopyrazolidin-1-yl}ethyl)benzoic acid whose Ki value was measured as described in Example 83 is 14 nM (Ki on EP2 being 4450 nM) induces the release of 10±3 ova when administered orally at the single dose of 20 mg/kg in the ovulation induction model decribed above.

4-[2-(2-{3-hydroxy-4-[3-(trifluoromethyl)phenyl]butyl}-5-oxopyrazolidin-1-yl)ethyl]benzoic acid whose Ki and/or $EC_{50}$ values were measured as described in Examples 83 and 84 are respectively 23 nM and 0.2 nM presents an $ED_{50}$ of 5 mg/kg by sc route in the ovulation induction model decribed above.

The results show that EP4 agonists are able to stimulate ovulation induction in mature mice in all three routes of administration (sc, iv, and po).

EXAMPLE 86

In Vivo Inhibition of Guinea Pig Broncho-constriction

Guinea pig pulmonary-cholinergic in vivo model is generally used to test the materials for the treatments of asthma in human (Fleisch at al. 1985, *K. Pharmacol. Exp. Ther*. 233: 148-157). Compounds of the invention are tested in this model.

Groups of 3 Duncan Hartley derived male or female guinea pigs weighing 250±50 g are anesthetized with pentobarbital sodium (50 mg/kg i.p., plus an additional 15 mg/kg i.p. if required) and succinylcholine chloride (2 mg/animal i.p.) is subsequently administered to prevent spontaneous respiration. Body temperature is maintained at 37° to 38° C.

The trachea is cannulated and the guinea pig is ventilated with a Harvard rodent respirator in a closed system. Tracheal pressure is recorded through a side-arm of the cannula connected to a P23ID Statham transducer. Respiratory rate is set at 50 strokes/minute with a stroke volume (approximately 1 ml/100 g) sufficient to produce a baseline tracheal pressure of 6 cm $H_2O$. Mean arterial pressure (BP) is monitored from a cannulated carotid artery, and heart-rate (HR) is obtained from chest electrodes arranged for lead II. The jugular vein is cannulated for i.v. vehicle or drug administration in a volume of 1 ml/kg.

Cholinergic-induced bronchoconstrictor responses, reflected as increases in tracheal pressure (cm $H_2O$), are elicited by administration of methacholine hydrochloride (10 µg/kg base weight i.v.). In vehicle-treated control animals, methacholine-induced bronchoconstriction ranges from 70 to 90 percent of its own maximum response (about 40 to 65 percent of maximum possible bronchoconstriction obtained by tracheal occlusion).

Compounds of the invention are also tested via intratracheal (IT) route of administration. In this other experiment, compound of the invention, reference compound or vehicle is administered IT 10 (5 min for experiment 1 and 2) minutes before methacholine chloride (10 µg/kg i.v.) induced bronchoconstriction. Tracheal pressure (ITP), blood pressure and heart rate are measured immediately as indicated in the material and methods sections.

MED (medium effective dose) is measured. A 50 percent or greater ($\geq 50\%$) inhibition of the induced bronchoconstriction relative to vehicle treated control animals is considered significant.

Compounds of the invention are administered i.v. (10 mg/kg) 5 minutes before subministration of the methacoline hydrochloride challenge in 3 guinea pigs. A 50 percent or more ($\geq 50$) inhibition of the induced bronchoconstriction relative to vehicle treated control animals is considered significant.

Compound of example 1 was injected i.v. to different concentrations from $3 \times 10^{-5}$ mg/kg up to 0.3 mg/kg. Significant methacholine-induced bronchoconstriction (>50%) inhibitions were observed at the doses $>3 \times 10^{-3}$ mg/kg. The calculated effective dose ($ED_{50}$) was about 1.7 µg/kg, while not altering neither blood pressure nor heart beat.

Compound of example 1 was tested at 4 doses (0.04, 0.4, 4.0 and 40 μg/guinea pig (GP)). One dose of reference compound (salbutamol) (40 μg/GP) and vehicle control were also tested. The calculated $ED_{50}$ was 0.72 μg/GP or 2.4 μg/kg via IT route of administration. BP and HR were measured in the experiment.

Compounds of the invention show an activity in dilation of bronchiolar muscles, which resulted in inhibition of methacholine-induced bronchomuscle constriction.

EXAMPLE 87

In Vivo Inhibition of LPS-induced TNFa Release in Mice

Prostaglandin E2 is suggested to be an endogenous inhibitor of inflammation through the EP4 receptor. Therefore EP2 and/or EP4 agonists are suppoed to have an anti-inflammatory activity.

Endotoxins are the lipopolysaccharides (LPS) constituents of the outer membrane of Gram negative bacteria Response to LPS has been shown to involve the activation of different cell populations and to lead to the expression of various inflammatory cytokines that include tumor necrosis factor-alpha (TNFα) and interferon gamma (IFN-γ).

The anti-inflammatory activity of compounds of the invention may be assessed after a LPS challenge using the following protocol:

Eight weeks old C3H/HEN mice (IFFA-CREDO, L'arbresle, France) receive an oral treatment with compounds of the invention 6 different doses (0.001, 0.01, 0.1, 1 or 3 and 10 mg/kg in 0.5% CMC/0.25% tween-20). Six mice are used by group. Fifteen minutes later, endotoxins (O111:B4 Sigma, 0.3 mg/kg) are intraperitoneally injected. Heparinized whole blood is collected by decapitation. TNFα level is determined in plasma by ELISA (R & D Systems, Abdingdon, UK). Control animals receive 0.5% CMC/0.25% tween-20 (10 ml/kg) as vehicle. Data obtained from experiments are expressed as the mean±SEM and analysed using one-way analysis of variance (ANOVA) followed by Dunnett's t-test.

The activity of the compounds of the invention is expressed as a percentage of inhibition of TNF release and the Inhibitory Dose at 50% of the maximum effect (ID50) is calculated in mg/kg. Data are presented in Table 4 below:

TABLE 4

| Example number | Dose (mg/kg) | % of Inhibition of TNF Release Mean ± SEM | $ID_{50}$ (mg/kg) |
| --- | --- | --- | --- |
| 45 | 0.001 | 87 ± 1 | 0.010 |
|  | 0.01 | 80 ± 1 |  |
|  | 0.1 | 69 ± 2.6 |  |
|  | 1 | 62 ± 2.2 |  |
|  | 10 | 49 ± 1 |  |
| 31 | 0.01 | 92 ± 1 | 0.003 |
|  | 0.1 | 88 ± 1 |  |
|  | 1 | 78 ± 2.6 |  |
|  | 3 | 61 ± 2.2 |  |
|  | 10 | 47 ± 1 |  |

The data show that the compounds of the invention are able to inhibit the release of TNF alpha in a LPS-challenge model.

EXAMPLE 88

In Vivo Effect on Penile Corpus Cavernosum Tissue Relaxation

Penile erection is based on three main physiological events: an increase in the arterial blood flow, a relaxation of the expansive tissue of the corpora carvernosa abd the corpus spongiosum, and an obstruction of the venous return by mechanicak compression of the veins caused by the expansive tissue.

PGE1 is used in the treatment of erectile dysfunction to relax smooth muscle and therefore to promote the development of erection. The administration of PGE1 is performed by local injection into the cavernous tissue of the penis. However, PGE1 has a low selectivity for prostanoid receptors and has irritant effects. Selective agonists EP2 and/or EP4 have been developed for the treatment of erectile dysfunction (WO 9902164)

The effect of compounds of the invention on the relaxation of penile corpus cavernosal tissue strips may be assayed for example in an assay on human or rabbit tissue as described below:

Human tissue procurement. Cavernosal tissue is obtained from patients undergoing penile prosthesis implantation surgery for treatment of erectile dysfunction. In the operating room, biopsies of the corpora cavernosa are immediately placed in chilled (4° C.) physiologic salt solution and transported to the laboratory. Tissue strips, measuring approximately 3 mm×3 mm×10 mm, are cut and prepared for organ bath studies.

Rabbit tissue procurement. Adult male New Zealand White rabbits (4.5-5.0 kg) are sedated with ketamine (35 mg/kg) and xylazine (5 mg/kg) and euthanized with sodium pentobarbital (60 mg/kg body weight). Following exsanguination, the penis is excised and cleaned by removing the corpus spongiosum and urethra Corpus cavernosum tissue strips are dissected away from the surrounding tunica albuginea and prepared for organ bath studies.

Preparation of compound stock solutions and dose responses. $PGE_1$ (Cayman Chemical Co., Ann Arbor, Mich.) is stored at −20° C. in solid form until the day of use. Stock solutions are made by adding 1 ml of 70% DMSO to a vial containing 1 mg of $PGE_1$. Compounds of the inention are dissolved in 1 ml of 70% DMSO, divided into 100 μl aliquots and stored at −20° C. until use. For dose responses in organ baths, stock solutions of $PGE_1$ and compounds of the invention are diluted with 70% DMSO to make the highest concentration and then serially diluted with 2% DMSO for all other doses. In a typical dose response curve, the concentration of DMSO is checked to remain below 0.1% in the 25 ml bath and to not exceed 0.5% at the highest dose.

Organ bath studies. Human or rabbit cavernosal tissue strips are mounted onto a fixed support with silk ties and attached to a tension transducer (model FT03; Grass-Telefactor, Astro-Med, Inc. West Warwick, R.I.) with a rigid metal wire. After mounting, tissue strips are immersed in 25 ml baths of physiologic salt solution (PSS; 118.3 mM. NaCl, 4.7 mM KCl, 0.6 mM $MgSO_4$, 1.2 mM $KH_2PO_4$, 2.5 mM $CaCl_2$, 25 mM $NaHCO_3$, 0.026 mM $CaNa_2EDTA$, 11.1 mM glucose). The solution is gassed with 95% air/5% $CO_2$ to attain a pH of 7.4 and the temperature is maintained at 37° C. All tissue strips are treated with 3 μM indomethacin to inhibit endogenous prostanoid production and minimize spontaneous contractile activity. The corpus cavernosum tissue is stretched incrementally and the optimal resting isometric tension for contraction is determined. After every 3-4 stretches (1 g tension/stretch), the tissue is contracted with 1 μM phenylephrine. When the amplitude of the phenylephrine-induced contraction is within 10% of the previous contraction, that tension is considered optimal for isometric contraction. All tissue strips are extensively washed with fresh PSS. Tissue strips are then contracted with 1 μM phenylephrine. After stable tone is achieved, tissue strips are exposed to increasing concentrations of PGE$_1$ or compounds of the invention.

Data analysis. At the end of each experiment, all tissue strips are treated with 10 μM papaverine and 10 μM nitroprusside to induce maximal relaxation (100%). The total amount of relaxatory response over the range of drug concentrations tested is determined by the area under the plotted curves. EC$_{50}$ values are calculated using Prism software (Graph-Pad, San Diego, Calif.). For final analysis of data, relaxation parameters are compared using ANOVA. If the ANOVA p-value is less than 0.05, paired post-test comparisons is carried out using the Tukey-Kramer test.

EXAMPLE 89

In Vivo Effect on Bone Loss Prevention

The activity of compounds of the invention as a bone anabolic agent can be tested for example in a rat ovariectomy model such as follows.

Virgin female Sprague Dawley rats are randomized into treatment groups based on pre-dose body weight measurements. The aim iss to achieve approximately the same average body weight for every treatment group.

Surgery:

Animals are sedated with Ketamine and Xylazine (SOP ST-AEP007). The hair on the dorsal abdominal surface is shaved and prepped for aseptic surgery. A single incision is made along the midline, starting just anterior to the lumbar region of the spine. The underlying musculature on both sides of the dorso-lateral region of the abdomen is exposed. An incision is made through the musculature to gain access to the abdominal cavity.

For a group of animals ("Ovx"), the ovary is located and cut at the junction of the uterine horn and removed. The uterus is replaced and the muscles sutured. Repeat on the contra-lateral side.

For a control group of animals ("Sham"), the ovaries are located and exteriorized, but not removed. The uterus and ovaries are replaced into the abdominal cavity and the muscles sutured.

The muscle layers are closed with suture and the skin incision closed using wound clips.

Dosing

Dosing is commenced one day after the surgery is performed. The animals receive daily subcutaneous injections for 6 weeks following surgery. The doses of 0.1, 1.0, 10.0 mg/kg of compounds of the invention are used. A control group receives daily subcutaneous injections of 17βestradiol (Sigma Chemicals) of 30 μg/kg for 6 weeks following surgery. Control groups of animal (the "sham" group and an "Ovx" group) are injected s.c. vehicle (saline).

Fluorochrome Labels

To enable the performance of dynamic histomorphometry, two injections of calcein (10 mg/kg, i.p.) are given 6 and 2 days prior to the necropsy.

Body Weights and Clinical Observations

Body weights are recorded weekly, beginning one week prior to the commencement of treatment and continuing until the conclusion of the treatment period. In addition, the rats are observed daily for signs of ill health or reaction to treatment.

Blood and Urine Biochemistry

An eighteen-hour urine specimen is collected from each animal prior to the sacrifice using metabolic cages. At sacrifice, blood samples are collected from each rat, under inhalation anesthesia (ether) from the retro-orbital sinus. Following parameters are measured in urine and serum.

Parameter Method

Urinary deoxypyridinoline is measured by Immuno-assay (Pyrilinks-D Quidel, Mt. View, Calif.); Urinary creatinine is measured by COBAS chemistry instrument (Creatinine Reagent Roche Diagnostics, Indianapolis, Ind.); Serum osteocalcin is measured by Immuno-assay (Rat OSU IRMA, Immunotopics San Clemente, Calif.)

Necropsy:

Upon completion of dosing and urine/blood collection, animals are euthanized using carbon dioxide asphyxiation.

All animals are subjected to the following procedure. Terminal body weights are recorded. A gross examination is performed and a check for abnormalities is performed. The following investigation are performed, as detailed:

Bone Mineral Density Scans:

L2-L4 lumbar vertebrae is subjected to DXA (Dual-energy X-ray absorptiometry) scan using a PIXImus instrument (Lunar Corp. Madison, Wis.). Bone mineral content, area and density are determined from the PIXI scan. Bone mineral density measurements by DXA are described in Formica et al. 1998, *Osteoporosis International*, 8 (5), 460-467.

Right femur is subject to pQCT (peripheral quantitative computed tomography) scan using a Stratec XCT RM and associated software (Stratec Medizintechnik Gmbh, Pforzheim, Germany. Software version 5.40 C). The femur is scanned at two sites, 20% of the distal femur and 50% of the mid-femur. The position is verified using scout views and scan results from one 0.5 mm slice perpendicular to the long axis of the femur shaft is recorded. Total bone mineral content, total bone area, total bone mineral density, trabecular bone mineral content, trabecular bone area and trabecular bone mineral density are analyzed from the scan of the distal femur. For the midshaft femur, total bone mineral content, total bone area, total bone mineral density, cortical bone mineral content, cortical bone area, cortical bone mineral density, periosteal perimeter and endosteal perimeter are analyzed.

Bone mineral density measurements by pQCT are described in Formica et al. 1998, *Osteoporosis International*, 8 (5), 460-467 *and in Tsugeno* 2002, *Osteoporosis International* 13(8), 650-656.

Biomechanical Testing of Lumbar Vertebrae and Femurs:

L5 Lumbar vertebra is isolated from L5-L6 and prepared for mechanical testing by removing the vertebral arch and pedicle using a low-speed diamond saw. The cranial and caudal ends of each vertebral body are also removed to produce a vertebral body specimen with two parallel surfaces and a height of approximately 4 mm. The width of the vertebral body in the medial-lateral and anterior-posterior directions is measured using electronic digital calipers. These values are recorded and used in the calculation of cross-sectional area. The height of the vertebral body specimen is also taken with an electronic caliper and recorded. The specimens are then placed between two platens and load applied at a displacement rate of 6 mm/min until failure in an Instron Mechanical Testing Instrument (Instron 4465, retrofitted to 5500).

The load and displacement are recorded by Instron Instrument Software (Merlin II, Instron) and the locations for maximum load at failure, stiffness and energy absorbed are selected manually from the load and displacement curve. The intrinsic properties, stress, elastic modulus and toughness are then calculated from maximum load, stiffness, energy absorbed, cross-sectional area, and height according to the following equations:

After the pQCT scan, the anterior to posterior diameter at the midpoint of the femoral shaft is taken with an electronic caliper and recorded. Femur is then placed on the lower supports of a three point bending fixture with anterior side facing downward in an Instron Mechanical Testing Instrument (Instron 4465, retrofitted to 5500). The span between the two lower supports is set at 14 mm. The upper loading device aligned to the center of the femoral shaft. The load is applied at a constant displacement rate of 6 mm/min until the femur breaks. The locations of maximal load, stiffness and energy absorbed are selected manually and values calculated by instrument's software (Merlin II, Instron). The intrinsic properties, stress, elastic modulus and toughness are calculated from maximum load, stiffness, energy absorbed, anterior-posterior diameter, and moment of inertia.

After the three point bending test, a 3-mm segment of the distal femoral metaphysis is cut directly proximal to the femoral condyle with a low-speed diamond saw. The load is applied with a cylindrical indenter (with a flat testing face of 1.6 mm diameter (d)) to the center of marrow cavity on the distal face of the segment. The indenter is allowed to penetrate the cavity at a constant displacement rate of 6 mm/min to a depth of 2 mm before load reversal. The locations of maximum load, stiffness and energy absorbed is selected manually from load displacement curve and then calculated by the instrument's software Merlin II, Instron). Stress is calculated by dividing the maximum load by the indenter area.

Bone Histology and Dynamic Histomorphometry:

Dehydration, Embedding and Sectioning

Formalin-fixed samples of proximal tibia are dehydrated in a series of ascending ethanol concentration. Following dehydration, bone samples are infiltrated and embedded in methyl methacrylate-based plastic. Embedded samples of the proximal tibia are sectioned longitudinally using a Leitz motorized rotary microtome equipped with a tungsten-carbide microtome knife. Once the blocks are trimmed, 4 µm sections are stained with Goldner's trichrome stain for microscopy. The 8 µm sections are left unstained for epifluorescence microscopy.

Histomorphometric Determinations

Static and dynamic histomorphometry of the proximal tibia is performed. The measurement includes the secondary spongiosa (area that is 1.05 from the lowest point of the growth plate).

Bone histomorphometry is performed using an OsteoMeasure software program (OsteoMetrics, Inc. Atlanta, Ga.) interfaced with a Nikon Eclipse E400 light/epifluorescent microscope and video subsystem. Histomorphometry is read in a blinded manner. Total tissue area, trabecular bone area, trabecular bone perimeter, and osteoclast perimeter is measured on 4 µm thick Goldner's trichrome stained sections. Percent trabecular bone area, trabecular number, trabecular thickness, trabecular separation and osteoclast perimeter as a percentage of bone surfaces are then calculated according to standardized formulae. For dynamic parameters, single-labeled calcein perimeter, double-labeled calcein perimeter, and interlabel width (label thickness) is measured on 8 µm thick unstained sections, and the mineralizing surface, mineral apposition rate, bone formation rate-surface referent is calculated.

Statistics

Results are analyzed using analysis of variance (group) using SAS software (SAS Institute, Cory, N.C.). Group comparison is performed using Dunnett's procedure using "Ovx"+vehicle group as reference group. All results are expressed as mean+/−SD.

The invention has been described in detail with reference to preferred embodiments thereof. However, it will be appreciated that those skilled in the art, upon consideration of this disclosure, may make modifications and improvements within the spirit and scope of the invention.

The invention claimed is:

1. A compound of the following Formula I:

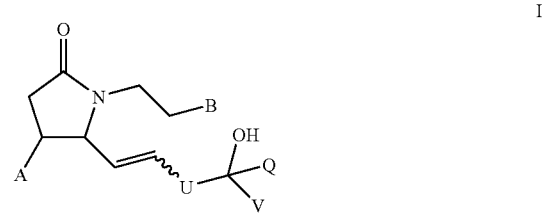

I wherein
A is hydrogen or hydroxy;
B is selected from optionally substituted carbocyclic aryl and optionally substituted heteroalicyclic having from 3 to 8 ring atoms and at least 1 N, O or S ring atom or a heteroaromatic group having a single ring with 5 or 6 ring atoms and at least one N, O or S ring atom;
U is $(CH_2)_p$ wherein p is selected from 0, 1 and 2;
V and Q are each independently hydrogen, optionally substituted alkenyl, optionally substituted alkynyl, and —$CR^1R^2$—W, wherein $R^1$ and $R^2$ are $C_1$-$C_6$ alkyl; or $R^1$ and $R^2$ can form an $C_3$-$C_6$ cycloalkyl with the carbon they are attached to;
W is selected from hydrogen, $C_1$-$C_6$ alkyl, $C_3$-$C_6$ cycloalkyl, $C_3$-$C_6$ cycloalkyl $C_1$-$C_6$ alkyl, aryl and heteroaryl; with at least one of V and Q being other than hydrogen; and pharmaceutically acceptable salts thereof.

2. A compound of claim 1 wherein A is hydrogen.

3. A compound of claim 1 wherein B is optionally substituted carbocyclic aryl.

4. A compound of claim 1 wherein B is optionally substituted phenyl.

5. A compound of Formula II:

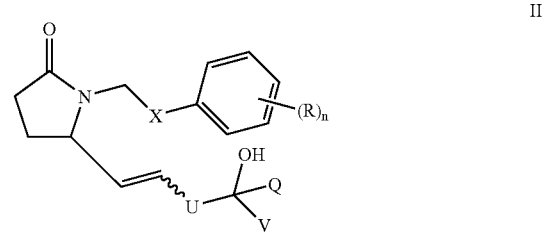

II wherein R is C(=O)Z where Z is selected from hydrogen, hydroxy, optionally substituted alkoxy and optionally substituted alkyl; or R is amino or optionally substituted alkylamine;
X is selected from oxygen and carbon;
n is an integer selected from 0, 1, 2, 3, 4 and 5;
U is $(CH_2)_p$ wherein p is selected from 0, 1 and 2;
V and Q are each independently selected from hydrogen, optionally substituted alkenyl, optionally substituted alkynyl, and —CR$^1$R$^2$—W, wherein R$^1$ and R$^2$ are C$_1$-C$_6$ alkyl; or R$^1$ and R$^2$ can form an C$_3$-C$_6$ cycloalkyl with the carbon they are attached to;

W is selected from hydrogen, C$_1$-C$_6$ alkyl, C$_3$-C$_6$ cycloalkyl, C$_3$-C$_6$ cycloalkyl C$_1$-C$_6$ alkyl, aryl and heteroaryl; with at least one of V and Q being other than hydrogen; and pharmaceutically acceptable salts thereof.

6. A compound of claim 5 wherein n is 1 or 2.

7. A compound of claim 1 having the following Formula III:

III wherein R is C(=O)Z where Z is selected from hydrogen, hydroxy, optionally substituted alkoxy and optionally substituted alkyl; or R is amino or optionally substituted alkylamine;

U is (CH$_2$)$_p$ wherein p is selected from 0, 1 and 2;

V and Q are each independently selected from hydrogen, optionally substituted alkenyl, optionally substituted alkynyl, and —CR$^1$R$^2$—W, wherein R$^1$ and R$^2$ are C$_1$-C$_6$ alkyl; or R$^1$ and R$^2$ can form an C$_3$-C$_6$ cycloalkyl with the carbon they are attached to;

W is selected from hydrogen, C$_1$-C$_6$ alkyl, C$_3$-C$_6$ cycloalkyl, C$_3$-C$_6$ cycloalkyl C$_1$-C$_6$ alkyl, aryl and heteroaryl; with at least one of V and Q being other than hydrogen; and pharmaceutically acceptable salts thereof.

8. A compound according to claims 1, 5, or 7 wherein p is zero.

9. A compound of claim 5 wherein n is 1 and R is a para-substituent.

10. A compound of claim 5 wherein R is —C(O)OH.

11. A compound of claim 5 wherein R is —C(O)OH being in a "para" position whereby n is 1; Q is CR$^1$R$^2$—W, wherein R$^1$ and R$^2$ are C$_1$-C$_6$ alkyl; or R$^1$ and R$^2$ can form an C$_3$-C$_6$ cycloalkyl with the carbon they are attached to; W is selected from hydrogen, C$_1$-C$_6$ alkyl, C$_2$-C$_6$ alkenyl, C$_3$-C$_6$ cycloalkyl, C$_3$-C$_6$ cycloalkyl C$_1$-C$_6$ alkyl, aryl, heteroaryl and aryl C$_1$-C$_6$ alkyl; and pharmaceutically acceptable salts thereof.

12. A compound of claim 5 wherein R is —C(O)OH is in a "para" position; n is 1; Q is CR$^1$R$^2$—W, wherein R$^1$ and R$^2$ are independently selected from C$_1$-C$_6$ alkyl; or R$^1$ and R$^2$ can form a C$_3$-C$_6$ cycloalkyl with the carbon they are attached to; W is selected from hydrogen, C$_1$-C$_6$ alkyl, C$_3$-C$_6$ cycloalkyl C$_1$-C$_6$ alkyl, and aryl; and pharmaceutically acceptable salts thereof.

13. A compound of claim 1 that is selected from the group consisting of:

4-(2-{(2R)-2-[(1E,4R)-4-hydroxy-4-(1-propylcyclobutyl)but-1-enyl]-5-oxopyrrolidin-1-yl}ethyl)benzoic acid;

4-[2-((2R)-2-{(1E,4R)-4-[1-(cyclopropylmethyl)cyclobutyl]-4-hydroxybut-1-enyl}-5-oxopyrrolidin-1-yl)ethyl]benzoic acid;

4-(2-{(2R)-2-[(1E,4R)-4-(1-ethylcyclobutyl)-4-hydroxybut-1-enyl]-5-oxopyrrolidin-1-yl}ethyl)benzoic acid;

4-(2-{(2R)-2-[(1E,3S)-3-hydroxy-4,4-dimethyloct-1-enyl]-5-oxopyrrolidin-1-yl}ethyl)benzoic acid;

4-[2-((2R)-2-{(1E,3S)-3-[1-(cyclopropylmethyl)cyclobutyl]-3-hydroxyprop-1-enyl}-5-oxopyrrolidin-1-yl)ethyl]benzoic acid;

4-[2-((2R)-2-{(1E,3R)-3-[1-(cyclopropylmethyl)cyclobutyl]-3-hydroxyprop-1-enyl}-5-oxopyrrolidin-1-yl)ethyl]benzoic acid;

4-(2-{(2S)-2-[(3S)-3-(1-butylcyclobutyl)-3-hydroxypropyl]-5-oxopyrrolidin-1-yl}ethyl)benzoic acid;

4-(2-{(2S)-2-[(3R)-3-(1-butylcyclobutyl)-3-hydroxypropyl]-5-oxopyrrolidin-1-yl}ethyl)benzoic acid;

4-(2-{(2R)-2-[(1E,3R)-3-hydroxy-3-(1-phenylcyclopentyl)prop-1-enyl]-5-oxopyrrolidin-1-yl}ethyl)benzoic acid;

4-(2-{(2R)-2-[(1E,3S)-3-hydroxy-3-(1-phenylcyclopentyl)prop-1-enyl]-5-oxopyrrolidin-1-yl}ethyl)benzoic acid;

4-[2-((2R)-2-{(1E,3R)-3-[1-(4-chlorophenyl)cyclopropyl]-3-hydroxyprop-1-enyl}-5-oxopyrrolidin-1-yl)ethyl]benzoic acid;

4-[2-((2R)-2-{(1E,3S)-3-[1-(4-chlorophenyl)cyclobutyl]-3-hydroxyprop-1-enyl}-5-oxopyrrolidin-1-yl)ethyl]benzoic acid 4-[2-((2R)-2-{(1E,3R)-3-[1-(4-chlorophenyl)cyclobutyl]-3-hydroxyprop-1enyl}-5-oxopyrrolidin-1-yl)ethyl]benzoic acid;

4-[2-((2R)-2-{(1E,3S)-3-[1-(4-chlorophenyl)cyclopropyl]-3-hydroxyprop-1-enyl}-5-oxopyrrolidin-1-yl)ethyl]benzoic acid;

4-[2-((2R)-2-{(1E,3S)-3-hydroxy-3-[1-(4-methylphenyl)cyclopentyl]prop-1-enyl}-5-oxopyrrolidin-1-yl)ethyl]benzoic acid;

4-[2-((2R)-2-{(1E,3R)-3-hydroxy-3-[1-(4-methylphenyl)cyclopentyl]prop-1-enyl}-5-oxopyrrolidin-1-yl)ethyl]benzoic acid;

4-[2-((2R)-2-{(1E,3S)-3-[1-(4-fluorophenyl)cyclopentyl]-3-hydroxyprop-1-enyl}-5-oxopyrrolidin-1-yl)ethyl]benzoic acid;

4-[2-((2R)-2-{(1E,3R)-3-[1-(4-fluorophenyl)cyclopentyl]-3-hydroxyprop-1-enyl}-5-oxopyrrolidin-1-yl)ethyl]benzoic acid;

4-[2-((2R)-2-{(1E,3R)-3-[1-(2-fluorophenyl)cyclopentyl]-3-hydroxyprop-1-enyl}-5-oxopyrrolidin-1-yl)ethyl]benzoic acid;

4-[2-((2R)-2-{(1E,3S)-3-[1-(2-fluorophenyl)cyclopentyl]-3-hydroxyprop-1-enyl}-5-oxopyrrolidin-1-yl)ethyl]benzoic acid;

4-[2-((2R)-2-{(1E,3S)-3-[1-(4-chlorophenyl)cyclopentyl]-3-hydroxyprop-1-enyl}-5-oxopyrrolidin-1-yl)ethyl]benzoic acid;

4-[2-((2R)-2-{(1E,3R)-3-[1-(4-chlorophenyl)cyclopentyl]-3-hydroxyprop-1-enyl}-5-oxopyrrolidin-1-yl)ethyl]benzoic acid;

4-[2-((2R)-2-{(1E,3S)-3-[1-(3-fluorophenyl)cyclopentyl]-3-hydroxyprop-1-enyl}-5-oxopyrrolidin-1-yl)ethyl]benzoic acid;

4-[2-((2R)-2-{(1E,3R)-3-[1-(3-fluorophenyl)cyclopentyl]-3-hydroxyprop-1-enyl}-5-oxopyrrolidin-1-yl)ethyl]benzoic acid;

4-[2-((2R)-2-{(1E,3S)-3-hydroxy-3-[1-(2-phenylethyl)cyclobutyl]prop-1-enyl}-5-oxopyrrolidin-1-yl)ethyl]benzoic acid;

4-[2-((2R)-2-{(1E,3R)-3-hydroxy-3-[1-(2-phenylethyl)cyclobutyl]prop-1-enyl}-5-oxopyrrolidin-1-yl)ethyl]benzoic acid;

4-(2-{(2R)-2-[(1E,3S)-3-hydroxy-3-(1-propylcyclobutyl)prop-1-enyl]-5oxopyrrolidin-1-yl}ethyl)benzoic acid 4-(2-{(2R)-2-[(1E,3R)-3-hydroxy-3-(1-propylcyclobutyl)prop-1-enyl]-5oxopyrrolidin-1-yl}ethyl)benzoic acid 4-(2-{(2R)-2-[(1E,3R)-3-(1-benzylcyclobutyl)-3-hydroxyprop-1-enyl]-5oxopyrrolidin-1-yl}ethyl)benzoic acid;

4-(2-{(2R)-2-[(1E,3S)-3-(1-butylcyclobutyl)-3-hydroxyprop-1-enyl]-5oxopyrrolidin-1-yl}ethyl)benzoic acid;

4-(2-{(2R)-2-[(1E,3R)-3-(1-butylcyclobutyl)-3-hydroxyprop-1-enyl]-5oxopyrrolidin-1-yl}ethyl)benzoic acid;

4-(2-{(2R)-2-[(1E,3R)-3-hydroxy-4,4-dimethyloct-1-enyl]-5-oxopyrrolidin-1-yl}ethyl)benzoic acid;

4-(2-{(2R)-2-[(1E,3S)-3-hydroxy-3-(1-phenylcyclopropyl)prop-1-enyl]-5-oxopyrrolidin-1-yl}ethyl)benzoic acid; and 4-(2-{(2R)-2-[(1E,3R)-3-hydroxy-3-(1-phenylcyclopropyl)prop-1-enyl]-5-oxopyrrolidin-1-yl}ethyl)benzoic acid; and pharmaceutically acceptable salts thereof.

14. A method for treating asthma, comprising administering to a mammal suffering from asthma an effective amount of a compound of claim 1.

15. A method for treating dysmenorrhea, comprising administering to a mammal suffering from dysmenorrhea an effective amount of a compound of claim 1.

16. A method for treating gastric ulcers, comprising administering to a mammal suffering from gastric ulcers an effective amount of a compound of claim 1.

17. A method for treating erectile dysfunction, comprising administering to a mammal suffering from erectile dysfunction an effective amount of a compound of claim 1.

18. A method of any one of claims 14, 15, 16, or 17 wherein the mammal is a human.

19. A method of claim any one of claims 14, 15, or 16 wherein the mammal is a female.

20. A method for treating an ovulatory disorder, comprising administering to a female mammal suffering from an ovulatory disorder an effective amount of a compound of claim 1.

21. A method of any one of claims 14, 16, or 17 wherein the mammal is a male.

22. A pharmaceutical composition comprising a pharmaceutically acceptable carrier and one or more compounds of claim 1.

23. A pharmaceutical composition of claim 22 wherein the compound is packaged together with instructions for use of the compound to treat preterm labor, dysmenorrhea, asthma, hypertension, infertility or a fertility disorder, sexual dysfunction, undesired blood clotting, a destructive bone disease or disorder, preeclampsia or eclampsia, an eosinophil disorder, renal dysfunction an immune deficiency disorder, dry eye, ichthyosis, elevated intraocular pressure, sleep disorder, or gastric ulcer.

24. A method of treating a fertility condition in a female, comprising the administration to said female a prostaglandin EP4 receptor agonist, a pharmaceutical acceptable salt of said prostaglandin EP4 receptor agonist, or a diastereoisomeric mixture of said prostaglandin EP4 receptor agonist or salt, wherein the prostaglandin EP4 receptor agonist is selected among compounds of formula II:

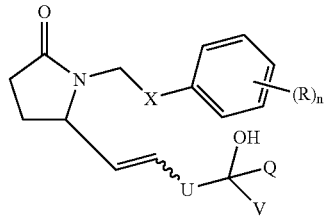

wherein:

X is selected from oxygen and carbon;

n is an integer selected from 0, 1, 2, 3, 4 and 5;

R is C(=O)Z wherein Z is selected from hydrogen, hydroxy, alkoxy, alkyl and aryl; or Z is selected from amino or alkylamine such as —$NR^4R^5$ wherein $R^4$ and $R^5$ are independently selected from hydrogen and alkyl, —$NHSO_2R^3$ and —$NHC(O)R^3$ wherein $R^3$ is selected among $C_1$-$C_6$ alkyl and aryl;

U is $(CH_2)_p$ wherein p is an integer selected from 0, 1 and 2:

Q is —$CR^1R^2$—W, wherein $R^1$ and $R^2$ are $C_1$-$C_6$ alkyl; or $R^1$ and $R^2$ can form a $C_3$-$C_6$ cycloalkyl with the carbon they are attached to;

W is selected from hydrogen, $C_1$-$C_6$ alkyl, $C_3$-$C_6$ cycloalkyl, $C_3$-$C_6$ cycloalkyl $C_1$-$C_6$ alkyl, aryl, and heteroaryl, with at least one of V and Q being other than hydrogen; and pharmaceutically acceptable salts thereof.

25. A method of claim 24 wherein the condition is infertility.

26. A method of claim 24 wherein the condition is an ovulatory disorder.

27. A method of claim 24 wherein the female is undergoing an ovulation induction or ART treatments.

28. A method of claim 24 wherein the prostaglandin EP4 receptor agonist is selected among compounds of formula II, wherein R is C(=O)Z wherein Z is selected from hydrogen, hydroxy, alkoxy such as —O-alkyl and alkyl; or Z is selected from amino or alkylamine such as —$NR^4R^5$ where $R^4$ and $R^5$ are independently hydrogen or alkyl, —$NHSO_2R^3$ and —$NHC(O)R^3$ wherein $R^3$ selected among $C_1$-$C_6$ alkyl and aryl; U is $(CH_2)_p$ wherein p is 0; Q is —$CR^1R^2$—W, wherein $R^1$ and $R^2$ are $C_1$-$C_6$ alkyl; W is selected from $C_3$-$C_6$ cycloalkyl, aryl and heteroaryl; and pharmaceutically acceptable salts thereof.

29. A method of claim 24 wherein the prostaglandin EP4 receptor agonist is selected among compounds of formula II, wherein R is C(=O)Z wherein Z is selected from hydrogen, hydroxy, alkoxy; U is $(CH_2)_p$ wherein p is 0; and pharmaceutically acceptable salts thereof.

30. A method of claim 24 wherein the prostaglandin EP4 receptor agonist is selected among compounds of formula II, wherein R is C(=O)Z wherein Z is selected from hydroxy and alkoxy; U is $(CH_2)_p$ wherein p is 0; and pharmaceutically acceptable salts thereof.

31. A method of claim 24 wherein the prostaglandin EP4 receptor agonist is selected among compounds of formula II wherein R is C(=O)Z wherein Z is hydroxy; U is $(CH_2)_p$ wherein p is 0; Q is —$CR^1R^2$—W, wherein $R^1$ and $R^2$ are $C_1$-$C_6$ alkyl; or $R^1$ and $R^2$ can form a $C_3$-$C_6$ cycloalkyl with the carbon they are attached to; W is selected from $C_1$-$C_6$ alkyl, $C_3$-$C_6$ cycloalkyl $C_1$-$C_6$ alkyl, $C_3$-$C_6$ cycloalkyl, and substituted phenyl; and pharmaceutically acceptable salts thereof.

32. A method of claim 24 wherein the prostaglandin EP4 receptor agonist is selected from the group consisting of:
- 4-(2-{(2R)-2-[(1E,3R)-3-hydroxy-3-(1-phenylcyclopropyl)prop-1-enyl]-5-oxopyrrolidin-1-yl}ethyl)benzoic acid;
- 4-(2-{(2R)-2-[(1E,3S)-3-(1-butylcyclobutyl)-3-hydroxyprop-1-enyl]-5-oxopyrrolidin-1-yl}ethyl)benzoic acid;
- 4-[2-((2R)-2-{(1E,3R)-3-[1-(cyclopropylmethyl)cyclobutyl]-3-hydroxyprop-1-enyl}-5-oxopyrrolidin-1-yl)ethyl]benzoic acid;
- 4-(2-{(2R)-2-[(1E,3R)-3-(1-butylcyclobutyl)-3-hydroxyprop-1-enyl]-5-oxopyrrolidin-1-yl}ethyl)benzoic acid; and
- 4-(2-{(2R)-2-[(1E,3R)-3-hydroxy-4,4-dimethyloct-1-enyl]-5-oxopyrrolidin-1-yl}ethyl)benzoic acid; and pharmaceutically acceptable salts thereof.

33. A method for treating asthma, comprising administering to a mammal suffering from asthma an effective amount of a compound of claim 5.

34. A method for treating dysmenorrhea, comprising administering to a mammal suffering from dysmenorrhea an effective amount of a compound of claim 5.

35. A method for treating gastric ulcers, comprising administering to a mammal suffering from gastric ulcers an effective amount of a compound of claim 5.

36. A method for treating erectile dysfunction, comprising administering to a mammal suffering from erectile dysfunction an effective amount of a compound of claim 5.

37. A method of any one of claims 33, 34, 35, or 36 wherein the mammal is a human.

38. A method of any one of claims 33, 34, or 35 wherein the mammal is a female.

39. A method for treating an ovulatory disorder, comprising administering to a female mammal suffering from an ovulatory disorder an effective amount of a compound of claim 5.

40. A method of any one of claims 33, 35, or 36 wherein the mammal is a male.

41. A pharmaceutical composition comprising a pharmaceutically acceptable carrier and one or more compounds of claim 5.

42. A pharmaceutical composition of claim 41 wherein the compound is packaged together with instructions for use of the compound to treat preterm labor, dysmenorrhea, asthma, hypertension, infertility or a fertility disorder, sexual dysfunction, undesired blood clotting, a destructive bone disease or disorder, preeclampsia or eclampsia, an eosinophil disorder, renal dysfunction, an immune deficiency disorder, dry eye, ichthyosis, elevated intraocular pressure, sleep disorder, or gastric ulcer.

* * * * *

UNITED STATES PATENT AND TRADEMARK OFFICE
CERTIFICATE OF CORRECTION

PATENT NO.       : 7,419,999 B2                                          Page 1 of 1
APPLICATION NO.  : 10/517626
DATED            : September 2, 2008
INVENTOR(S)      : Araldi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 291 days.

Signed and Sealed this

Second Day of November, 2010

David J. Kappos
*Director of the United States Patent and Trademark Office*